US012584191B2

(12) United States Patent
Yew et al.

(10) Patent No.: US 12,584,191 B2
(45) Date of Patent:        Mar. 24, 2026

(54) USING SYNTHETIC LIXIVIANT BIOLOGY FOR THE RECOVERY OF PRECIOUS AND TOXIC METALS FROM ANTHROPOGENIC SOURCES

(71) Applicant: NATIONAL UNIVERSITY OF SINGAPORE, Singapore (SG)

(72) Inventors: Wen Shan Yew, Singapore (SG); Maybelle Darlene Kho Go, Singapore (SG); Lu Ting Liow, Singapore (SG); Rashmi Rajasabhai, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 861 days.

(21) Appl. No.: 17/601,802

(22) PCT Filed: Apr. 8, 2020

(86) PCT No.: PCT/SG2020/050216
§ 371 (c)(1),
(2) Date: Oct. 6, 2021

(87) PCT Pub. No.: WO2020/209797
PCT Pub. Date: Oct. 15, 2020

(65) Prior Publication Data
US 2022/0205062 A1      Jun. 30, 2022

(30) Foreign Application Priority Data

Apr. 8, 2019     (SG) ............................ 10201903117U
May 24, 2019     (SG) ............................ 10201904705X

(51) Int. Cl.
| | |
|---|---|
| C22B 11/08 | (2006.01) |
| C12N 1/06 | (2006.01) |
| C12N 9/02 | (2006.01) |
| C12N 9/04 | (2006.01) |
| C12N 9/06 | (2006.01) |
| C12N 9/22 | (2006.01) |
| C12N 15/10 | (2006.01) |
| C12N 15/11 | (2006.01) |
| C12N 15/90 | (2006.01) |
| C12P 13/00 | (2006.01) |

(52) U.S. Cl.
CPC ................ C22B 11/08 (2013.01); C12N 1/06 (2013.01); C12N 9/0006 (2013.01); C12N 9/0014 (2013.01); C12N 9/0091 (2013.01); C12N 9/22 (2013.01); C12N 15/102 (2013.01); C12N 15/11 (2013.01); C12N 15/902 (2013.01); C12P 13/002 (2013.01); C12Y 101/01095 (2013.01); C12Y 104/99005 (2013.01); C12Y 116/01001 (2013.01); *C12N 2310/20* (2017.05); *C12N 2800/80* (2013.01)

(58) Field of Classification Search
CPC ......... C12B 11/08; C12N 1/06; C12N 9/0006; C12N 9/0014; C12N 9/0091; C12N 9/22; C12N 15/11; C12N 15/902; C12N 2310/20; C12N 2800/80; C12P 13/002; C12Y 101/01095; C12Y 104/99005; C12Y 116/01001
See application file for complete search history.

(56) References Cited

U.S. PATENT DOCUMENTS 5,965,796 A      10/1999   Meagher et al.

FOREIGN PATENT DOCUMENTS

| CN | 102796714 A | 11/2012 |
|---|---|---|
| JP | H0216782 A | 6/1990 |
| WO | 2015066411 A1 | 5/2015 |

OTHER PUBLICATIONS

International Search Report and Written Opinion received for PCT Application No. PCT/SG2020/050216, mailed on Sep. 21, 2020, 16 pages.
Rennex D. et al., "In vivo and in vitro effects of mutagenesis of active site tyrosine residues of mercuric reductase", FEBS Letters, Dec. 15, 1994, vol. 355, No. 3, pp. 220-222.

(Continued)

*Primary Examiner* — Suzanne M Noakes
*Assistant Examiner* — Ciara A McKnight
(74) *Attorney, Agent, or Firm* — Meunier Carlin & Curfman LLC

(57) ABSTRACT

The present invention generally relates to methods of biological reduction of metal-cyanide complexes after metal-cyanidation and methods of biologically hydrolysing cyanide. More particularly, the present invention allows the engineering of an integrated synthetic lixiviant biological system to be housed within a synthetic host (such as the cyanogenic *Chromobacterium violaceum*) for efficient precious metal recovery and toxic metal remediation of electronic waste; with up to four main components/modules in the design and engineering of the synthetic host: 1) synthetic cyanogenesis; 2) synthetic metal recovery; 3) synthetic cyanolysis; and 4) synthetic circuits for lixiviant biology. Bacteria capable of reducing ionic metal to ionic metal (such as gold or silver) as nanoparticles, comprising mercury(11) reductase (MerA) comprising a substitution mutation at position V317, Y441, C464, A323D, A414E, G415I, E416C, L417I, I418D, or A422N, are also disclosed. Processes of synthetic cyanide lixiviant production using genetically engineered bacterium transformed with a heterologous hydrogen cyanide synthase gene and a heterologous 3-phosphoglycerate dehydrogenase mutant gene are also disclosed. Processes of synthetic cyanolysis using a genetically engineered bacterium transformed with a heterologous nitrilase gene are also disclosed.

4 Claims, 22 Drawing Sheets

Specification includes a Sequence Listing.

(56) References Cited

OTHER PUBLICATIONS

Notice of Reasons for Refusal, issued in connection with JP Application No. 2021-559714, Feb. 27, 2024, 28 pages.

Office Action, issued in connection with CN Application No. 202080040580.0, Nov. 21, 2023, 13 pages.

Supplementary Search Report, issued in connection with EP Application No. 20786863.9, Feb. 27, 2023, 13 pages.

Office Action, issued in connection with MY Application No. PI2021006026, Sep. 12, 2024, 4 pages.

Office Action, issued in connection with SG Application No. 11202111208R, 8 pages.

Office Action, issued in connection with SG Application No. 11202111208R, May 30, 2025, 8 pages.

Bikard, et al. "Programmable repression and activation of bacterial gene expression using an engineered CRISPR-Cas system" Nucleic Acids Research, vol. 41, No. 15, 2013.

Brandl, et al. "Biomobilization of silver, gold and platinum from solid waste materials by HCN-forming microorganims" Hydrometallurgy 94, p. 14-17, 2008.

Brysk, et al. "β-Cyanoalanine Formation by Chromobacterium violaceum" Journal of Bacteriology, vol. 97, No. 1, p. 322-327, 1969.

Brysk, et al. "γ-Cyano-60 -L-aminobutyric Acid" The Journal of Biological Chemistry, vol. 245, No. 5, Issue of Mar. 10, p. 1156-1160, 1970.

Cerminatir, et al. "Selective Detection of Gold Using Genetically Engineered Bacterial Reporters" Biotechnology and Bioengineering, vol. 108, No. 11, 2011.

Checa, et al. "Bacterial sensing of and resistance to gold salts" Molecular Microbiology, p. 1307-1318, 2007.

Chi, et al. "Bioleaching of gold and copper from waste mobile phone PCBs by using acyanogenic bacterium" Minerals Engineering, p. 1219-1222, 2011.

Cho, et al. "Applications of CRISPR/Cas System to Bacterial Metabolic Engineering" International Journal of Molecular Sciences, 2018.

Cobb, et al. "High-Effciency Multiplex Genome Editing of *Streptomyces* Species Using an Engineered CRISPOR/Cas System" ACS Snyth. Biol., p. 723-728, 2014.

Dasari, et al. "Antibacterial Activity and Cytotoxicity of Gold (I) and (III) Ions and Gold Nanoparticles" Biochem Pharmacol., 2015.

Faramarzi, et al. "Metal solubilization from metal-containing solid materials by cyanogenic Chromobacterium violaceum" Journal of Biotechnology, p. 321-326, 2004.

Fields, et al. "the Earth: Gold Mining's Dirty Secret" Environmental Health Perspectives, vol. 109, No. 10, 2001.

Kang, et al. "Extracellular Saccharide-Mediated Reduction of Au3+ to Gold Nanoparticles: New Insights for Heavy Metals Biomineralization on Microbial Surfaces" Environmental Sci. Technol., p. 2776-2785, 2017.

Knowles "Microorganisms and Cyanide" Bacteriological Reviews, vol. 40, No. 3, p. 652-680, 1976.

Knowles, et al. "Microbial Cyanide Metabolism" Advances in Microbial Physiology, vol. 27, 1986.

Korte, et al. "The Cyanide Leaching Gold Recovery Process Is a Nonsustainable Technology with Unacceptable Impacts on Ecosystems and Humans: The Disaster in Romania" Ecotoxicology and Environmental Safety, p. 241-245, 2000.

Krebs, et al. "Microbial recovery of metals from solids" Microbiology Reviews, p. 605-617, 1997.

Liang, et al. "Novel strategies of bioleaching metals from printed circuit boards (PCBs) in mixed cultivation of two acidophiles" Enzyme and Microbial Technology, p. 322-326, 2010.

Liu, et al. "Toxicity Assessment of Cyanide and Tetramethylene Disulfotetramine (Tetramine) Using Luminescent Bacteria Vibrioqinghaiensis and PbO2 Electrochemical Sensor" Chinese Journal of Chemistry, p. 203-207, 2007.

Maged, et al. "Thermal Stability ofa Mercuric Reductase from the Red Sea Atlantis II Hot Brine Environment as Analyzed by Site-Directed Mutagenesis" Applied and Environmental Microbiology, vol. 85, Issue 3, 2019.

Moore, et al. "C-Terminal Cysteines of Tn501 Mercuric Ion Reductase" American Chemical Society, 1992.

Nigam, et al. "Bioengineering of Nitrilases Towards Its Use as Green Catalyst: Applications and Perspectives" Indian Journal of Microbiology, p. 131-138, 2017.

Arazoe, et al. "Targeted Nucleotide Editing Technologies for Microbial Metabolic Engineering" Biotechnology Journal, 2018.

Pham, et al. "Gold bioleaching of electronic waste by cyanogenic bacteria and its enhancement with bio-oxidation" Advanced Materials Research, vols. 71-73, p. 661-664, 2009.

Rawlings "Heavy Metal Mining Using Microbes" Annu. Rev. Microbiol., p. 65-91, 2002.

Reith, et al. "Mechanisms of gold biomineralization in the bacterium Cupriavidus metallidurans" PNAS, vol. 106, No. 42, p. 17757-17762, 2009.

Ressler, et al. "Purification and Characterization from Chromobacterium violaceum of an Enzyme Catalyzing the Synthesis of γ-Cyano-α-aminobutyric Acid and Thiocyanate" Biochemistry, vol. 12, No. 26, 1973.

Rugh, et al. "Mercuric ion reduction and resistance in transgenic *Arabidopsis thaliana* plants expressing a modified bacterial merA gene" Proc. Natl. Acad. Sci. USA, vol. 93, pp. 3182-3187, 1996.

Stanton, et al. "Genomic Mining of Prokawotic Repressors for Orthogonal Logic Gates" Nat Chem Biol., p. 99-105, 2014.

Swem, et al. "A Quorum-Sensing Antagonist Targets Both Membrane-Bound and Cytoplasmic Receptors and Controls Bacterial Pathogenicity" Mol Cell., p. 143-153, 2009.

Tay, et al. "Enhancing gold recovery from electronic waste via lixiviant metabolic engineering in chromobacterium violaceum" Scientific Reports, 2013.

Watling "The bioleaching of sulphide minerals with emphasis on copper sulphides—A review" Hydrometallurgy, p. 81-108, 2006.

Deep scanning mutagenesis library of templates for golS

Construction of library mutants

Transformation of library mutants into *C. violaceum*

Selection of *C. violaceum* for higher fluorescence output and re-clone mutants
- Transilluminator
- Microplate reader
- Flow cytometry

Figure 15

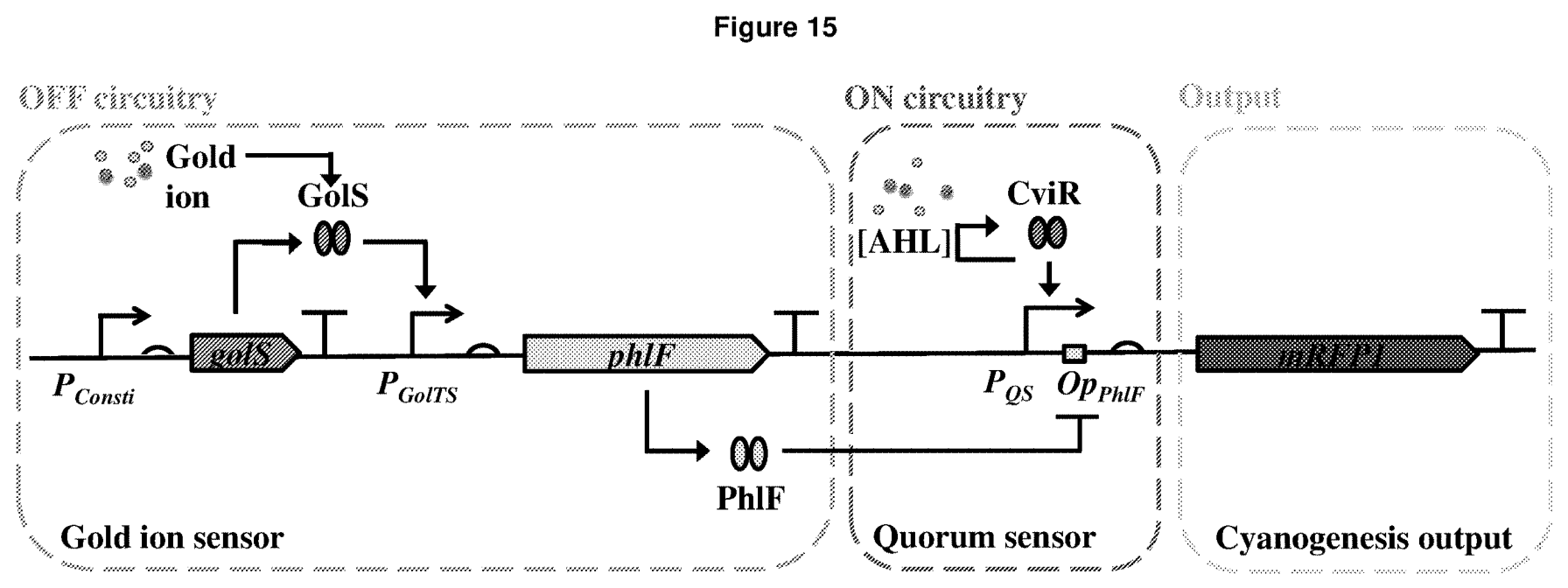

Output

Cyanogenesis output

ON circuitry

CviR

[AHL]

$P_{QS}$   $Op_{PhlF}$

Quorum sensor

OFF circuitry

Gold ion

GolS $P_{GolTS}$ phlF

PhlF $P_{Consti}$ golS

Gold ion sensor golTSB operon (A) Absence of gold reducing MerA        (B) Presence of gold reducing MerA

A

B

| AuCl$_3$ | Leachate |
| --- | --- |
| WT MerA | |

| AuCl$_3$ | Leachate |
| --- | --- |
| DM11 | |

A

B

Leached e-waste by co-culturing electronic scrap metal with *C. violaceum* for 6 days Filtered supernatant after centrifugation Gold and silver biosensor ICP analysis for gold and silver ions quantitation

SEQUENCE LISTING

<160> NUMBER OF SEQ ID NOS: 53

<210> SEQ ID NO 1
<211> LENGTH: 24
<212> TYPE: DNA
<213> ORGANISM: Artificial Sequence
<220> FEATURE:
<223> OTHER INFORMATION: Forward primer merA -continued

<400> SEQUENCE: 1
gtggtggtgg tggtgctcga gtta                                                                                24

<210> SEQ ID NO 2
<211> LENGTH: 30
<212> TYPE: DNA
<213> ORGANISM: Artificial Sequence
<220> FEATURE:
<223> OTHER INFORMATION: Reverse primer merA

<400> SEQUENCE: 2
gatatacata tgcaccacca tcaccatcat                                                                          30

<210> SEQ ID NO 3
<211> LENGTH: 20
<212> TYPE: DNA
<213> ORGANISM: Artificial Sequence
<220> FEATURE:
<223> OTHER INFORMATION: T7-fw

<400> SEQUENCE: 3
taatacgact cactataggg                                                                                     20

<210> SEQ ID NO 4
<211> LENGTH: 21
<212> TYPE: DNA
<213> ORGANISM: Artificial Sequence
<220> FEATURE:
<223> OTHER INFORMATION: T7-rv

<400> SEQUENCE: 4
gctagttatt gctcagcggt g                                                                                   21

<210> SEQ ID NO 5
<211> LENGTH: 33
<212> TYPE: DNA
<213> ORGANISM: Artificial Sequence
<220> FEATURE:
<223> OTHER INFORMATION: V317NNK-fw
<220> FEATURE:
<221> NAME/KEY: misc_feature
<222> LOCATION: (16)..(17)
<223> OTHER INFORMATION: n is a, c, g, or t

<400> SEQUENCE: 5
gatcaaccgc agttcnnkta tgttgcggct gcc                                                                      33

<210> SEQ ID NO 6
<211> LENGTH: 33
<212> TYPE: DNA
<213> ORGANISM: Artificial Sequence
<220> FEATURE:
<223> OTHER INFORMATION: V317NNK-rv
<220> FEATURE:
<221> NAME/KEY: misc_feature
<222> LOCATION: (17)..(18)
<223> OTHER INFORMATION: n is a, c, g, or t

<400> SEQUENCE: 6
ggcagccgca acatamnnga actgcggttg atc                                                                      33

<210> SEQ ID NO 7
<211> LENGTH: 36
<212> TYPE: DNA
<213> ORGANISM: Artificial Sequence
<220> FEATURE:
<223> OTHER INFORMATION: Y441NNK-fw

```
<220> FEATURE:
<221> NAME/KEY: misc_feature
<222> LOCATION: (18)..(19)
<223> OTHER INFORMATION: n is a, c, g, or t

<400> SEQUENCE: 7
cggatcagct gtttccgnnk ctgacaatgg tcgaag                              36

<210> SEQ ID NO 8
<211> LENGTH: 36
<212> TYPE: DNA
<213> ORGANISM: Artificial Sequence
<220> FEATURE:
<223> OTHER INFORMATION: Y441NNK-rv
<220> FEATURE:
<221> NAME/KEY: misc_feature
<222> LOCATION: (18)..(19)
<223> OTHER INFORMATION: n is a, c, g, or t

<400> SEQUENCE: 8
cttcgaccat tgtcagmnnc ggaaacagct gatccg                              36

<210> SEQ ID NO 9
<211> LENGTH: 43
<212> TYPE: DNA
<213> ORGANISM: Artificial Sequence
<220> FEATURE:
<223> OTHER INFORMATION: C464NNK-fw
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 9
gatgtcaaac aattgtcgnn knnkgcaggc taactcgagc acc                      43

<210> SEQ ID NO 10
<211> LENGTH: 43
<212> TYPE: DNA
<213> ORGANISM: Artificial Sequence
<220> FEATURE:
<223> OTHER INFORMATION: C464NNK-rv
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t

<400> SEQUENCE: 10
ggtgctcgag ttagcctgcm nnmnncgaca attgtttgac atc                      43

<210> SEQ ID NO 11
<211> LENGTH: 1515
<212> TYPE: DNA
<213> ORGANISM: Artificial Sequence
<220> FEATURE:
<223> OTHER INFORMATION: nit

<400> SEQUENCE: 11
atgccgagcg tcgatatcgc ccattacaag gacggcgact tcctggtcaa ctacgaagag     60
aaggttttcg aggacgtcaa ggccgagcca ggcgagaaag ccctcatcac cttccacacc    120
```

-continued

```
atcgctttcg agggttccat tggcctggtc aacatgctgc aggccaaacg cctgctgcgc      180
aaaggcttcg agaccaaggt gctgctctac gggccgggcg tgcagcttgg cgtgcagcgt      240
ggcttcccca ccctgggcaa tgaagccttc cccggccacc tggcggtcaa caaccagatc      300
aaggcgttca tcgaggaagg cggtgaggtc tatgcctgcc gtttcgccct gcaggccctg      360
tacgggcaga ccgagaaagc gctgatcgaa ggcatccgcg ccatcaaccc gctggacgtg      420
atggatctgc gtttgctgat gcgtcgcgaa ggcgcgctga tcatcgacac ctggactgcc      480
tgatccttcc cgcccctcct gcgggagggg ccacgttcgt acaaggaatt cgccatggcc      540
atcgtccgtg ccgctgccgt gcagctctcg cccgtgctct acagtcgcga gggtaccgtc      600
gagaagatcg tccagaccat cctgcgcctc ggccgcgagg gcgtgcagtt tgccgtcttc      660
ccggaaaccg tggtgcccta ctacccctat ttctccttcg tgcagcctcc gttcatgatg      720
ggcaaggagc atctgcgcct gctcgaggag tcggtgcagt gccgtcggc ggcgaccgcc      780 gcgattgccg aggcctgtcg cgaagctcgg atggtggtgt cgctgggcat caacgagcgt      840
gacggtggca cgatctacaa cgctcaactg ttgttcgatg ccgatggcag cctcattcag      900
catcggcgca agatcactcc gacctaccat gagcgtatgg tctgggggca gggcgatggc      960
tctggcctgc gtgctgtggc cagccaggtc gggcgtatcg gctcgctggc ctgctgggag     1020
cactataacc cgctggcgcg ctatgccctg atggccgatg gcgagcagat tcatgcggcg     1080
atgtttcccg gttcgctggt gggggagatc ttcgccgagc agatcgaggt cagcatccgc     1140
caccatgcgc tggagtccgg ctgcttcgtg gtcaacgcca ccgcctggct ggagccggaa     1200
cagcagcagc gcatcatggt cgataccggc tgtgggctgg ggccgatttc cggcggttgc     1260
ttcaccgcca tcgtcagccc cgaaggcaag ctgctggggg agccgctgcg cagtggcgag     1320
ggtgaggtga tcgccgatct cgacctgacg ctgatcgaca agcgcaagcg catgatggat     1380
tcggtcggcc actacagccg gccggaactg ctcagcctgc tgatcgaccg cacgcctacc     1440
gcccacctgc atgagcgcgt cacggcgctg ccggggcggc atgaagccga ggaggtcgag     1500
catgtcagcc tctga                                                      1515
```

```
<210> SEQ ID NO 12
<211> LENGTH: 346
<212> TYPE: PRT
<213> ORGANISM: Artificial Sequence
<220> FEATURE:
<223> OTHER INFORMATION: SC-nit

<400> SEQUENCE: 12

Met Leu Gly Lys Ile Met Leu Asn Tyr Thr Lys Asn Ile Arg Ala Ala
1               5                   10                  15

Ala Ala Gln Ile Ser Pro Val Leu Phe Ser Gln Gln Gly Thr Met Glu
            20                  25                  30

Lys Val Leu Asp Ala Ile Ala Asn Ala Ala Lys Lys Gly Val Glu Leu
        35                  40                  45

Ile Val Phe Pro Glu Thr Phe Val Pro Tyr Tyr Pro Tyr Phe Ser Phe
    50                  55                  60

Val Glu Pro Pro Val Leu Met Gly Lys Ser His Leu Lys Leu Tyr Gln
65                  70                  75                  80

Glu Ala Val Thr Val Pro Gly Lys Val Thr Gln Ala Ile Ala Gln Ala
                85                  90                  95

Ala Lys Thr His Gly Met Val Val Val Leu Gly Val Asn Glu Arg Glu
            100                 105                 110
```

```
Glu Gly Ser Leu Tyr Asn Thr Gln Leu Ile Phe Asp Ala Asp Gly Ala
        115                 120                 125

Leu Val Leu Lys Arg Arg Lys Ile Thr Pro Thr Tyr His Glu Arg Met
        130                 135                 140

Val Trp Gly Gln Gly Asp Gly Ala Gly Leu Arg Thr Val Asp Thr Thr
145                 150                 155                 160

Val Gly Arg Leu Gly Ala Leu Ala Cys Trp Glu His Tyr Asn Pro Leu
                165                 170                 175

Ala Arg Tyr Ala Leu Met Ala Gln His Glu Gln Ile His Cys Gly Gln
                180                 185                 190

Phe Pro Gly Ser Met Val Gly Gln Ile Phe Ala Asp Gln Met Glu Val
                195                 200                 205

Thr Met Arg His His Ala Leu Glu Ser Gly Cys Phe Val Ile Asn Ala
        210                 215                 220

Thr Gly Trp Leu Thr Ala Glu Gln Lys Leu Gln Ile Thr Thr Asp Glu
225                 230                 235                 240

Lys Met His Gln Ala Leu Ser Gly Gly Cys Tyr Thr Ala Ile Ile Ser
                245                 250                 255

Pro Glu Gly Lys His Leu Cys Glu Pro Ile Ala Glu Gly Glu Gly Leu
                260                 265                 270

Ala Ile Ala Asp Leu Asp Phe Ser Leu Ile Ala Lys Arg Lys Arg Met
                275                 280                 285

Met Asp Ser Val Gly His Tyr Ala Arg Pro Asp Leu Leu Gln Leu Thr
        290                 295                 300

Leu Asn Asn Gln Pro Trp Ser Ala Leu Glu Ala Asn Pro Val Thr Pro
305                 310                 315                 320

Asn Ala Ile Pro Ala Val Ser Asp Pro Glu Leu Thr Glu Thr Ile Glu
                325                 330                 335

Ala Leu Pro Asn Asn Pro Ile Phe Ser His
                340                 345
```

```
<210> SEQ ID NO 13
<211> LENGTH: 330
<212> TYPE: PRT
<213> ORGANISM: Artificial Sequence
<220> FEATURE:
<223> OTHER INFORMATION: BP-cynD

<400> SEQUENCE: 13
```

```
Met Thr Ser Ile Tyr Pro Lys Phe Arg Ala Ala Ala Val Gln Ala Ala
1                   5                   10                  15

Pro Ile Tyr Leu Asn Leu Glu Ala Ser Val Glu Lys Ser Cys Glu Leu
        20                  25                  30

Ile Asp Glu Ala Ala Ser Asn Gly Ala Lys Leu Val Ala Phe Pro Glu
        35                  40                  45

Ala Phe Leu Pro Gly Tyr Pro Trp Phe Ala Phe Ile Gly His Pro Glu
        50                  55                  60

Tyr Thr Arg Lys Phe Tyr His Glu Leu Tyr Lys Asn Ala Val Glu Ile
65                  70                  75                  80

Pro Ser Leu Ala Ile Arg Lys Ile Ser Glu Ala Ala Lys Arg Asn Gly
                85                  90                  95

Thr Tyr Val Cys Ile Ser Cys Ser Glu Lys Asp Gly Gly Ser Leu Tyr
                100                 105                 110

Leu Ala Gln Leu Trp Phe Asn Pro Asn Gly Asp Leu Ile Gly Lys His
        115                 120                 125
```

```
Arg Lys Met Arg Ala Ser Val Ala Glu Arg Leu Ile Trp Gly Asp Gly
    130             135             140

Ser Gly Ser Met Met Pro Val Phe Gln Thr Glu Ile Gly Asn Leu Gly
145             150             155             160

Gly Leu Met Cys Trp Glu His Gln Val Pro Leu Asp Leu Met Ala Met
            165             170             175

Asn Ala Gln Asn Glu Gln Val His Val Ala Ser Trp Pro Gly Tyr Phe
            180             185             190

Asp Asp Glu Ile Ser Ser Arg Tyr Tyr Ala Ile Ala Thr Gln Thr Phe
            195             200             205

Val Leu Met Thr Ser Ser Ile Tyr Thr Glu Glu Met Lys Glu Met Ile
    210             215             220

Cys Leu Thr Gln Glu Gln Arg Asp Tyr Phe Glu Thr Phe Lys Ser Gly
225             230             235             240

His Thr Cys Ile Tyr Gly Pro Asp Gly Glu Pro Ile Ser Glu Met Val
            245             250             255

Pro Ala Glu Thr Glu Gly Ile Ala Tyr Ala Glu Ile Asp Val Glu Arg
            260             265             270

Val Ile Asp Tyr Lys Tyr Tyr Ile Asp Pro Ala Gly His Tyr Ser Asn
    275             280             285

Gln Ser Leu Ser Met Asn Phe Asn Gln Gln Pro Thr Pro Val Val Lys
    290             295             300

His Leu Asn His Gln Lys Asn Glu Val Phe Thr Tyr Glu Asp Ile Gln
305             310             315             320

Tyr Gln His Gly Ile Leu Gly Glu Lys Val
            325             330
```

```
<210> SEQ ID NO 14
<211> LENGTH: 334
<212> TYPE: PRT
<213> ORGANISM: Artificial Sequence
<220> FEATURE:
<223> OTHER INFORMATION: PS-synD

<400> SEQUENCE: 14
```

```
Met Ala His Tyr Pro Lys Phe Lys Ala Ala Ala Val Gln Ala Ala Pro
1               5               10              15

Val Tyr Leu Asn Leu Asp Ala Thr Val Glu Lys Ser Val Lys Leu Ile
            20              25              30

Glu Glu Ala Ala Ser Asn Gly Ala Lys Leu Val Ala Phe Pro Glu Ala
        35              40              45

Phe Ile Pro Gly Tyr Pro Trp Phe Ala Phe Leu Gly His Pro Glu Tyr
    50              55              60

Thr Arg Arg Phe Tyr His Thr Leu Tyr Leu Asn Ala Val Glu Ile Pro
65              70              75              80

Ser Glu Ala Val Gln Lys Ile Ser Ala Ala Arg Lys Asn Lys Ile
            85              90              95

Tyr Val Cys Ile Ser Cys Ser Glu Lys Asp Gly Gly Ser Leu Tyr Leu
            100             105             110

Ala Gln Leu Trp Phe Asn Pro Glu Gly Asp Leu Ile Gly Lys His Arg
    115             120             125

Lys Met Arg Val Ser Val Ala Glu Arg Leu Cys Trp Gly Asp Gly Asn
    130             135             140

Gly Ser Met Met Pro Val Phe Glu Thr Glu Ile Gly Asn Leu Gly Gly
145             150             155             160
```

-continued

```
Leu Met Cys Trp Glu His Asn Val Pro Leu Asp Ile Ala Ala Met Asn
                165             170             175

Ser Gln Asn Glu Gln Val His Val Ala Ala Trp Pro Gly Phe Phe Asp
            180             185             190

Asp Glu Thr Ala Ser Ser His Tyr Ala Ile Cys Asn Gln Ala Phe Val
            195             200             205

Leu Met Thr Ser Ser Ile Tyr Ser Glu Glu Met Lys Asp Met Leu Cys
        210             215             220

Glu Thr Gln Glu Glu Arg Asp Tyr Phe Asn Thr Phe Lys Ser Gly His
225             230             235             240

Thr Arg Ile Tyr Gly Pro Asp Gly Glu Pro Ile Ser Asp Leu Val Pro
                245             250             255

Ala Glu Thr Glu Gly Ile Ala Tyr Ala Glu Ile Asp Ile Glu Lys Ile
            260             265             270

Ile Asp Phe Lys Tyr Tyr Ile Asp Pro Val Gly His Tyr Ser Asn Gln
            275             280             285

Ser Leu Ser Met Asn Phe Asn Gln Ser Pro Asn Pro Val Val Arg Lys
        290             295             300

Ile Gly Glu Arg Asp Ser Thr Val Phe Thr Tyr Asp Asp Leu Asn Leu
305             310             315             320

Ser Val Ser Asp Glu Glu Pro Val Val Arg Ser Leu Arg Lys
                325             330
```

```
<210> SEQ ID NO 15
<211> LENGTH: 160
<212> TYPE: PRT
<213> ORGANISM: Artificial Sequence
<220> FEATURE:
<223> OTHER INFORMATION: NitB

<400> SEQUENCE: 15

Met Pro Ser Val Asp Ile Ala His Tyr Lys Asp Gly Asp Phe Leu Val
1               5               10              15

Asn Tyr Glu Glu Lys Val Phe Glu Asp Val Lys Ala Glu Pro Gly Glu
                20              25              30

Lys Ala Leu Ile Thr Phe His Thr Ile Ala Phe Glu Gly Ser Ile Gly
            35              40              45

Leu Val Asn Met Leu Gln Ala Lys Arg Leu Leu Arg Lys Gly Phe Glu
        50              55              60

Thr Lys Val Leu Leu Tyr Gly Pro Gly Val Gln Leu Gly Val Gln Arg
65              70              75              80

Gly Phe Pro Thr Leu Gly Asn Glu Ala Phe Pro Gly His Leu Ala Val
                85              90              95

Asn Asn Gln Ile Lys Ala Phe Ile Glu Glu Gly Gly Glu Val Tyr Ala
            100             105             110

Cys Arg Phe Ala Leu Gln Ala Leu Tyr Gly Gln Thr Glu Lys Ala Leu
        115             120             125

Ile Glu Gly Ile Arg Ala Ile Asn Pro Leu Asp Val Met Asp Leu Arg
        130             135             140

Leu Leu Met Arg Arg Glu Gly Ala Leu Ile Ile Asp Thr Trp Thr Ala
145             150             155             160
```

```
<210> SEQ ID NO 16
<211> LENGTH: 326
<212> TYPE: PRT
<213> ORGANISM: Artificial Sequence
<220> FEATURE:
```

<223> OTHER INFORMATION: NitC

<400> SEQUENCE: 16

```
Met Ala Ile Val Arg Ala Ala Ala Val Gln Leu Ser Pro Val Leu Tyr
1               5                   10                  15

Ser Arg Glu Gly Thr Val Glu Lys Ile Val Gln Thr Ile Leu Arg Leu
                20                  25                  30

Gly Arg Glu Gly Val Gln Phe Ala Val Phe Pro Glu Thr Val Val Pro
            35                  40                  45

Tyr Tyr Pro Tyr Phe Ser Phe Val Gln Pro Pro Phe Met Met Gly Lys
    50                  55                  60

Glu His Leu Arg Leu Leu Glu Glu Ser Val Gln Val Pro Ser Ala Ala
65                  70                  75                  80

Thr Ala Ala Ile Ala Glu Ala Cys Arg Glu Ala Arg Met Val Val Ser
                85                  90                  95

Leu Gly Ile Asn Glu Arg Asp Gly Gly Thr Ile Tyr Asn Ala Gln Leu
            100                 105                 110

Leu Phe Asp Ala Asp Gly Ser Leu Ile Gln His Arg Arg Lys Ile Thr
        115                 120                 125

Pro Thr Tyr His Glu Arg Met Val Trp Gly Gln Gly Asp Gly Ser Gly
    130                 135                 140

Leu Arg Ala Val Ala Ser Gln Val Gly Arg Ile Gly Ser Leu Ala Cys
145                 150                 155                 160

Trp Glu His Tyr Asn Pro Leu Ala Arg Tyr Ala Leu Met Ala Asp Gly
                165                 170                 175

Glu Gln Ile His Ala Ala Met Phe Pro Gly Ser Leu Val Gly Glu Ile
            180                 185                 190

Phe Ala Glu Gln Ile Glu Val Ser Ile Arg His His Ala Leu Glu Ser
        195                 200                 205

Gly Cys Phe Val Val Asn Ala Thr Ala Trp Leu Glu Pro Glu Gln Gln
    210                 215                 220

Gln Arg Ile Met Val Asp Thr Gly Cys Gly Leu Gly Pro Ile Ser Gly
225                 230                 235                 240

Gly Cys Phe Thr Ala Ile Val Ser Pro Glu Gly Lys Leu Leu Gly Glu
                245                 250                 255

Pro Leu Arg Ser Gly Glu Gly Glu Val Ile Ala Asp Leu Asp Leu Thr
            260                 265                 270

Leu Ile Asp Lys Arg Lys Arg Met Met Asp Ser Val Gly His Tyr Ser
        275                 280                 285

Arg Pro Glu Leu Leu Ser Leu Leu Ile Asp Arg Thr Pro Thr Ala His
    290                 295                 300

Leu His Glu Arg Val Thr Ala Leu Pro Gly Arg His Glu Ala Glu Glu
305                 310                 315                 320

Val Glu His Val Ser Leu
                325
```

<210> SEQ ID NO 17
<211> LENGTH: 1368
<212> TYPE: PRT
<213> ORGANISM: Artificial Sequence
<220> FEATURE:
<223> OTHER INFORMATION: dCas9

<400> SEQUENCE: 17

```
Met Asp Lys Lys Tyr Ser Ile Gly Leu Ala Ile Gly Thr Asn Ser Val
1               5                   10                  15
```

```
Gly Trp Ala Val Ile Thr Asp Glu Tyr Lys Val Pro Ser Lys Lys Phe
         20                  25                  30

Lys Val Leu Gly Asn Thr Asp Arg His Ser Ile Lys Lys Asn Leu Ile
         35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
             100                 105                 110

His Glu Arg His Pro Ile Phe Gly Asn Ile Val Asp Glu Val Ala Tyr
         115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                 165                 170                 175

Asp Asn Ser Asp Val Asp Lys Leu Phe Ile Gln Leu Val Gln Thr Tyr
             180                 185                 190

Asn Gln Leu Phe Glu Glu Asn Pro Ile Asn Ala Ser Gly Val Asp Ala
         195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                 245                 250                 255

Asp Leu Ala Glu Asp Ala Lys Leu Gln Leu Ser Lys Asp Thr Tyr Asp
             260                 265                 270

Asp Asp Leu Asp Asn Leu Leu Ala Gln Ile Gly Asp Gln Tyr Ala Asp
         275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                 325                 330                 335

Ala Leu Val Arg Gln Gln Leu Pro Glu Lys Tyr Lys Glu Ile Phe Phe
             340                 345                 350

Asp Gln Ser Lys Asn Gly Tyr Ala Gly Tyr Ile Asp Gly Gly Ala Ser
         355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                 405                 410                 415

Gly Glu Leu His Ala Ile Leu Arg Arg Gln Glu Asp Phe Tyr Pro Phe
         420                 425                 430
```

-continued

```
Leu Lys Asp Asn Arg Glu Lys Ile Glu Lys Ile Leu Thr Phe Arg Ile
        435             440             445

Pro Tyr Tyr Val Gly Pro Leu Ala Arg Gly Asn Ser Arg Phe Ala Trp
        450             455             460

Met Thr Arg Lys Ser Glu Glu Thr Ile Thr Pro Trp Asn Phe Glu Glu
465             470             475             480

Val Val Asp Lys Gly Ala Ser Ala Gln Ser Phe Ile Glu Arg Met Thr
                485             490             495

Asn Phe Asp Lys Asn Leu Pro Asn Glu Lys Val Leu Pro Lys His Ser
            500             505             510

Leu Leu Tyr Glu Tyr Phe Thr Val Tyr Asn Glu Leu Thr Lys Val Lys
        515             520             525

Tyr Val Thr Glu Gly Met Arg Lys Pro Ala Phe Leu Ser Gly Glu Gln
        530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
                565             570             575

Ser Val Glu Ile Ser Gly Val Glu Asp Arg Phe Asn Ala Ser Leu Gly
            580             585             590

Thr Tyr His Asp Leu Leu Lys Ile Ile Lys Asp Lys Asp Phe Leu Asp
        595             600             605

Asn Glu Glu Asn Glu Asp Ile Leu Glu Asp Ile Val Leu Thr Leu Thr
        610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
                645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
        675             680             685

Ala Asn Arg Asn Phe Met Gln Leu Ile His Asp Asp Ser Leu Thr Phe
        690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
                725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
        755             760             765

Thr Thr Gln Lys Gly Gln Lys Asn Ser Arg Glu Arg Met Lys Arg Ile
        770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
                805             810             815

Gln Asn Gly Arg Asp Met Tyr Val Asp Gln Glu Leu Asp Ile Asn Arg
            820             825             830

Leu Ser Asp Tyr Asp Val Asp Ala Ile Val Pro Gln Ser Phe Leu Lys
        835             840             845

Asp Asp Ser Ile Asp Asn Lys Val Leu Thr Arg Ser Asp Lys Asn Arg
```

-continued

```
        850              855              860
Gly Lys Ser Asp Asn Val Pro Ser Glu Glu Val Val Lys Lys Met Lys
865                  870              875              880

Asn Tyr Trp Arg Gln Leu Leu Asn Ala Lys Leu Ile Thr Gln Arg Lys
                885              890              895

Phe Asp Asn Leu Thr Lys Ala Glu Arg Gly Gly Leu Ser Glu Leu Asp
            900              905              910

Lys Ala Gly Phe Ile Lys Arg Gln Leu Val Glu Thr Arg Gln Ile Thr
        915              920              925

Lys His Val Ala Gln Ile Leu Asp Ser Arg Met Asn Thr Lys Tyr Asp
    930              935              940

Glu Asn Asp Lys Leu Ile Arg Glu Val Lys Val Ile Thr Leu Lys Ser
945              950              955              960

Lys Leu Val Ser Asp Phe Arg Lys Asp Phe Gln Phe Tyr Lys Val Arg
                965              970              975

Glu Ile Asn Asn Tyr His His Ala His Asp Ala Tyr Leu Asn Ala Val
            980              985              990

Val Gly Thr Ala Leu Ile Lys Lys  Tyr Pro Lys Leu Glu  Ser Glu Phe
        995              1000              1005

Val Tyr  Gly Asp Tyr Lys Val  Tyr Asp Val Arg Lys  Met Ile Ala
    1010              1015              1020

Lys Ser  Glu Gln Glu Ile Gly  Lys Ala Thr Ala Lys  Tyr Phe Phe
    1025              1030              1035

Tyr Ser  Asn Ile Met Asn Phe  Phe Lys Thr Glu Ile  Thr Leu Ala
    1040              1045              1050

Asn Gly  Glu Ile Arg Lys Arg  Pro Leu Ile Glu Thr  Asn Gly Glu
    1055              1060              1065

Thr Gly  Glu Ile Val Trp Asp  Lys Gly Arg Asp Phe  Ala Thr Val
    1070              1075              1080

Arg Lys  Val Leu Ser Met Pro  Gln Val Asn Ile Val  Lys Lys Thr
    1085              1090              1095

Glu Val  Gln Thr Gly Gly Phe  Ser Lys Glu Ser Ile  Leu Pro Lys
    1100              1105              1110

Arg Asn  Ser Asp Lys Leu Ile  Ala Arg Lys Lys Asp  Trp Asp Pro
    1115              1120              1125

Lys Lys  Tyr Gly Gly Phe Asp  Ser Pro Thr Val Ala  Tyr Ser Val
    1130              1135              1140

Leu Val  Val Ala Lys Val Glu  Lys Gly Lys Ser Lys  Lys Leu Lys
    1145              1150              1155

Ser Val  Lys Glu Leu Leu Gly  Ile Thr Ile Met Glu  Arg Ser Ser
    1160              1165              1170

Phe Glu  Lys Asn Pro Ile Asp  Phe Leu Glu Ala Lys  Gly Tyr Lys
    1175              1180              1185

Glu Val  Lys Lys Asp Leu Ile  Ile Lys Leu Pro Lys  Tyr Ser Leu
    1190              1195              1200

Phe Glu  Leu Glu Asn Gly Arg  Lys Arg Met Leu Ala  Ser Ala Gly
    1205              1210              1215

Glu Leu  Gln Lys Gly Asn Glu  Leu Ala Leu Pro Ser  Lys Tyr Val
    1220              1225              1230

Asn Phe  Leu Tyr Leu Ala Ser  His Tyr Glu Lys Leu  Lys Gly Ser
    1235              1240              1245

Pro Glu  Asp Asn Glu Gln Lys  Gln Leu Phe Val Glu  Gln His Lys
    1250              1255              1260
```

-continued

```
His Tyr  Leu Asp Glu Ile Ile  Glu Gln Ile Ser Glu  Phe Ser Lys
    1265             1270             1275

Arg Val  Ile Leu Ala Asp Ala  Asn Leu Asp Lys Val  Leu Ser Ala
    1280             1285             1290

Tyr Asn  Lys His Arg Asp Lys  Pro Ile Arg Glu Gln  Ala Glu Asn
    1295             1300             1305

Ile Ile  His Leu Phe Thr Leu  Thr Asn Leu Gly Ala  Pro Ala Ala
    1310             1315             1320

Phe Lys  Tyr Phe Asp Thr Thr  Ile Asp Arg Lys Arg  Tyr Thr Ser
    1325             1330             1335

Thr Lys  Glu Val Leu Asp Ala  Thr Leu Ile His Gln  Ser Ile Thr
    1340             1345             1350

Gly Leu  Tyr Glu Thr Arg Ile  Asp Leu Ser Gln Leu  Gly Gly Asp
    1355             1360             1365
```

```
<210> SEQ ID NO 18
<211> LENGTH: 20
<212> TYPE: DNA
<213> ORGANISM: Artificial Sequence
<220> FEATURE:
<223> OTHER INFORMATION: vioA promoter targeted

<400> SEQUENCE: 18
cgtccgccgt tgccgcgcgg                                              20

<210> SEQ ID NO 19
<211> LENGTH: 20
<212> TYPE: DNA
<213> ORGANISM: Artificial Sequence
<220> FEATURE:
<223> OTHER INFORMATION: vioB promoter targeted

<400> SEQUENCE: 19
cgtcgccgcc cggttccggg                                              20

<210> SEQ ID NO 20
<211> LENGTH: 20
<212> TYPE: DNA
<213> ORGANISM: Artificial Sequence
<220> FEATURE:
<223> OTHER INFORMATION: vioC promoter targeted

<400> SEQUENCE: 20
agagcaatca tagtcggagg                                              20

<210> SEQ ID NO 21
<211> LENGTH: 1190
<212> TYPE: DNA
<213> ORGANISM: Artificial Sequence
<220> FEATURE:
<223> OTHER INFORMATION: ParaBAD

<400> SEQUENCE: 21
ttatgacaac ttgacggcta catcattcac tttttcttca caaccggcac ggaactcgct    60
cgggctggcc ccggtgcatt ttttaaatac ccgcgagaaa tagagttgat cgtcaaaacc   120
aacattgcga ccgacggtgg cgataggcat ccgggtggtg ctcaaaagca gcttcgcctg   180
gctgatacgt tggtcctcgc gccagcttaa gacgctaatc cctaactgct ggcggaaaag   240
atgtgacaga cgcgacggcg acaagcaaac atgctgtgcg acgctggcga tatcaaaatt   300
gctgtctgcc aggtgatcgc tgatgtactg acaagcctcg cgtacccgat tatccatcgg   360
```

-continued

```
tggatggagc gactcgttaa tcgcttccat gcgccgcagt aacaattgct caagcagatt    420
tatcgccagc agctccgaat agcgcccttc cccttgcccg gcgttaatga tttgcccaaa    480
caggtcgctg aaatgcggct ggtgcgcttc atccgggcga aagaacccccg tattggcaaa   540 tattgacggc cagttaagcc attcatgcca gtaggcgcgc ggacgaaagt aaacccactg    600
gtgataccat tcgcgagcct ccggatgacg accgtagtga tgaatctctc ctggcgggaa    660
cagcaaaata tcacccggtc ggcaaacaaa ttctcgtccc tgattttca ccaccccctg      720 accgcgaatg gtgagattga gaatataacc tttcattccc agcggtcggt cgataaaaaa    780
atcgagataa ccgttggcct caatcggcgt taaacccgcc accagatggg cattaaacga    840
gtatcccggc agcaggggat cattttgcgc ttcagccata cttttcatac tcccgccatt    900
cagagaagaa accaattgtc catattgcat cagacattgc cgtcactgcg tcttttactg    960
gctcttctcg ctaaccaaac cggtaacccc gcttattaaa agcattctgt aacaaagcgg   1020
gaccaaagcc atgacaaaaa cgcgtaacaa aagtgtctat aatcacggca gaaaagtcca   1080
cattgattat ttgcacggcg tcacactttg ctatgccata gcatttttat ccataagatt   1140
agcggattct acctgacgct ttttatcgca actctctact gtttctccat              1190
```

```
<210> SEQ ID NO 22
<211> LENGTH: 35
<212> TYPE: DNA
<213> ORGANISM: Artificial Sequence
<220> FEATURE:
<223> OTHER INFORMATION: J23119

<400> SEQUENCE: 22
ttgacagcta gctcagtcct aggtataatg ctagc                               35
```

```
<210> SEQ ID NO 23
<211> LENGTH: 3237
<212> TYPE: DNA
<213> ORGANISM: Artificial Sequence
<220> FEATURE:
<223> OTHER INFORMATION: golTSB operon

<400> SEQUENCE: 23
acaacgaagg aaaggtcaag cgttcctgac gggttttac ggggcgtggg tcggcatcgt      60
ggcgtaaatg tctcgcatca tcctctttta tgagccatct cacattctcg ccgaaccgtg    120
cagcctgaat acgcttgacc ttcccacaat ggcaagcttt aggctttctg ataccgaata    180
gtcaggatgg ggaagtcgtc atgagtcagt cagaaaatcg tcacgacacg ataagcttac    240
ttattgaagg tatgacctgc gcgtcgtgcg tcgctcgcgt tgaaaaaggt attaaggctg    300
tgcctggcgt aacggacgct acggtgaatc tggcgacgga gcgcgccacc gtccgcggga    360
cggcgtcggc ggaggcggtg atcgcggcga ttgaaaaaac ggggtataag gcgcgaccga    420
tagagacggc ggggcagggc gaagacgact ctgaagagaa aaaagaggcc gagcgcgtca    480
ggctgaagcg cgatctgatt ctcgccagcg tgctggcgct ccccgttttt gtgcttgaaa    540
tgggctcgca ccttattcct ggtatgcacg agtgggtgat aaaaacgatt ggcctgcaac    600
aaagctggta ctggcaattt gcactgaccc tgttggtgct gacgatcccc ggtcgccgtt    660
tttaccttaa agggttcccg gcgctggcgc gtctggcgcc ggacatgaac tcgctggtcg    720
ccgtgggaac cgcagcggca ttcggctact cgctggtggc gacctttacg cccgacctgt    780
tgcctgaagg gacggtaaac gtctattacg aggccgccgc agtgattgtc gcgcttattc    840
```

```
tgctggggcg ctttctggag gcaagggcga aggggcggac ttccgaagcg attaaacgtc      900
tggtggggct acaggcgcgg gtcgcgcatg tgttacgcga gggccgcatc gtggatatcc      960
ctgtcgacga ggttgtgctg ggcgactgtg tggaggttcg gccaggcgag cggatcccgg     1020
ttgacggcga agtgaccgaa ggccgcagct tcgttgacga gtcgatgatt accggcgaac     1080
cgataccggt tgagaaatcc gcaggaagcg cggtggtggg cggtaccgta aaccaaaaag     1140
gcgcgctcac gctgcgggcg accgccgtcg cggacagac catgctggcg caaatcattc      1200
gtctggtgga acaggcgcag ggttcaaaac tgccgattca ggccgtcgtg gataaagtga     1260
cgctgtggtt tgtcccgatg gtgatgctta ttgctgcgct gacctttgtg gtatggctgg     1320
cgtttgggcc gtcgccagcg ctgactttcg ctctgatcaa tggcgttgcg gttctgatta     1380
tcgcctgtcc ttgcgcgatg ggcctggcga cgccgacctc tattatggtg ggaaccggtc     1440
gtggggcgga aatgggcgtg ctgttccgta aggggggaggc gttacagcta ctcaaagacg     1500
ctaaggtggt ggccgtagac aaaaccggga cgcttaccga aggccgcccg gtactgaccg     1560
atctcgacgt ggccagcggc tttgaacgcc gtgaggtgct ggcgaaagtc gcggcggtag     1620
aatcgcgttc agagcatccg attgcccgtg cgattgtcgt gtcggcagaa gaggaaggga     1680
tcgcgctacc aggcatgagc ggcttcgaat cggtgaccgg gatgggcgta tacgctaccg     1740
ttgacggtac gcgtgttgac gtgggggctg atcgctatat gcgcgaaatt ggcgtggata     1800
ttagcggctt cgccaccacc gccgaacggt tagggcagga agggaaatcg ccgctctatg     1860
cggctattga cggtcaactg gcggcgatta tcgccgtggc cgatccgatc aaacccagta     1920
cgcccgccgc aattaacgct ttacatcagc tcggcattaa ggtcgccatg atcactggcg     1980
ataatgcccg cacggcacag gctatcgcca gacagttagg aattgatgat gtggttgccg     2040
aggtattgcc agaagggaaa gtcgaggcga tacggcgcct gaaagcggcg tatgggcagg     2100
tggcgtttgt cggcgatggc atcaacgatg cgccagcgct ggcggagtcc gacgtggggc     2160
tggcgattgg caccggcacc gatgtggcgg tggaatccgc cgacgtcgta ctaatgtccg     2220
gcaacctgca aggcgtgccg aatgctatcg cgctgtctaa agcgaccatc cgcaatatcc     2280
accagaatct gttctgggcc tttgcttaca atacggcgct gattcctgtc gcggcaggcg     2340
cgctatttcc ggtctggggc atattattgt caccggtatt cgccgcaggg gcgatggcga     2400
tgtcgagcgt gttcgtgctg ggcaacgctt tgcggctgcg ccgtttccgg gcgccgatgg     2460
caaccccatc cgacacatcc acgacatgag gaggagcgtc atgaacatcg gtaaagcagc     2520
taaagcatcg aaagtctcgg ccaaaatgat tcgctactat gaacagattg gtctgattcc     2580
cgcggcaagt cggacggatt ccggctatcg ggcctatacc caggctgatg ttaatcaatt     2640
gcattttata cgccgcgcgc gcgacctcgg tttttcagtt gctgaaatca gcgacttact     2700
gaatctttgg aataaccagt cgcggcaaag cgctgacgtc aaacgcctgg cgcagacgca     2760
cattgatgaa ctgacagac gtatccagaa catgcagcac atggcgcaaa ccctcaaagc     2820
gctgattcac tgctgcgccg gcgacgcgct gccagattgc cccattctgc atacgcttgg     2880
acaacctgac gatagcgagc cggaggcgcg taccggagcg gtattgcgac gtcctcgtcg     2940
ccacggactg gcaaagcgtc tgtaagtcct gagattacgt ttgaccttcc aacactggca     3000
aggtccagac tggcaacagt tcccacacaa aaggagttca ctatgcagtt ccatattgat     3060
gacatgacct cgcggcggctg cgccagtacg gtaaaaaaga cgattctgac tctcgatgct     3120
aatgcgacgg tgagaactga cccggcgacg cgtctggttg acgttgaaac gtcgctatcc     3180
gcggagcaga ttgccgccgc cctgcaaaag gccggtttcc cgccgcgcga gaggtaa       3237
```

<210> SEQ ID NO 24
<211> LENGTH: 154
<212> TYPE: PRT
<213> ORGANISM: Artificial Sequence
<220> FEATURE:
<223> OTHER INFORMATION: GolS

<400> SEQUENCE: 24

Met Asn Ile Gly Lys Ala Ala Lys Ala Ser Lys Val Ser Ala Lys Met
1               5                   10                  15

Ile Arg Tyr Tyr Glu Gln Ile Gly Leu Ile Pro Ala Ala Ser Arg Thr
                20                  25                  30

Asp Ser Gly Tyr Arg Ala Tyr Thr Gln Ala Asp Val Asn Gln Leu His
            35                  40                  45

Phe Ile Arg Arg Ala Arg Asp Leu Gly Phe Ser Val Ala Glu Ile Ser
    50                  55                  60

Asp Leu Leu Asn Leu Trp Asn Asn Gln Ser Arg Gln Ser Ala Asp Val
65                  70                  75                  80

Lys Arg Leu Ala Gln Thr His Ile Asp Glu Leu Asp Arg Arg Ile Gln
                85                  90                  95

Asn Met Gln His Met Ala Gln Thr Leu Lys Ala Leu Ile His Cys Cys
            100                 105                 110

Ala Gly Asp Ala Leu Pro Asp Cys Pro Ile Leu His Thr Leu Gly Gln
            115                 120                 125

Pro Asp Asp Ser Glu Pro Glu Ala Arg Thr Gly Ala Val Leu Arg Arg
    130                 135                 140

Pro Arg Arg His Gly Leu Ala Lys Arg Leu
145                 150

<210> SEQ ID NO 25
<211> LENGTH: 200
<212> TYPE: DNA
<213> ORGANISM: Artificial Sequence
<220> FEATURE:
<223> OTHER INFORMATION: PgolTS

<400> SEQUENCE: 25
acaacgaagg aaaggtcaag cgttcctgac gggttttttac ggggcgtggg tcggcatcgt      60
ggcgtaaatg tctcgcatca tcctcttttta tgagccatct cacattctcg ccgaaccgtg     120
cagcctgaat acgcttgacc ttcccacaat ggcaagcttt aggctttctg ataccgaata     180
gtcaggatgg ggaagtcgtc                                                  200

<210> SEQ ID NO 26
<211> LENGTH: 77
<212> TYPE: DNA
<213> ORGANISM: Artificial Sequence
<220> FEATURE:
<223> OTHER INFORMATION: PgolB

<400> SEQUENCE: 26
gtcctgagat tacgcttgac cttccaacac tggcaaggtc cagactggca acagttccca      60
cacaaaagga gttcact                                                     77

<210> SEQ ID NO 27
<211> LENGTH: 154
<212> TYPE: PRT
<213> ORGANISM: Artificial Sequence
<220> FEATURE:

<223> OTHER INFORMATION: GolS-mt1 A38I

<400> SEQUENCE: 27

```
Met Asn Ile Gly Lys Ala Ala Lys Ala Ser Lys Val Ser Ala Lys Met
1               5                   10                  15

Ile Arg Tyr Tyr Glu Gln Ile Gly Leu Ile Pro Ala Ala Ser Arg Thr
            20                  25                  30

Asp Ser Gly Tyr Arg Ile Tyr Thr Gln Ala Asp Val Asn Gln Leu His
            35                  40                  45

Phe Ile Arg Arg Ala Arg Asp Leu Gly Phe Ser Val Ala Glu Ile Ser
        50                  55                  60

Asp Leu Leu Asn Leu Trp Asn Asn Gln Ser Arg Gln Ser Ala Asp Val
65                  70                  75                  80

Lys Arg Leu Ala Gln Thr His Ile Asp Glu Leu Asp Arg Arg Ile Gln
                85                  90                  95

Asn Met Gln His Met Ala Gln Thr Leu Lys Ala Leu Ile His Cys Cys
                100                 105                 110

Ala Gly Asp Ala Leu Pro Asp Cys Pro Ile Leu His Thr Leu Gly Gln
                115                 120                 125

Pro Asp Asp Ser Glu Pro Glu Ala Arg Thr Gly Ala Val Leu Arg Arg
        130                 135                 140

Pro Arg Arg His Gly Leu Ala Lys Arg Leu
145                 150
```

<210> SEQ ID NO 28
<211> LENGTH: 154
<212> TYPE: PRT
<213> ORGANISM: Artificial Sequence
<220> FEATURE:
<223> OTHER INFORMATION: GolS-mt2 A38Q N97D

<400> SEQUENCE: 28

```
Met Asn Ile Gly Lys Ala Ala Lys Ala Ser Lys Val Ser Ala Lys Met
1               5                   10                  15

Ile Arg Tyr Tyr Glu Gln Ile Gly Leu Ile Pro Ala Ala Ser Arg Thr
            20                  25                  30

Asp Ser Gly Tyr Arg Gln Tyr Thr Gln Ala Asp Val Asn Gln Leu His
            35                  40                  45

Phe Ile Arg Arg Ala Arg Asp Leu Gly Phe Ser Val Ala Glu Ile Ser
        50                  55                  60

Asp Leu Leu Asn Leu Trp Asn Asn Gln Ser Arg Gln Ser Ala Asp Val
65                  70                  75                  80

Lys Arg Leu Ala Gln Thr His Ile Asp Glu Leu Asp Arg Arg Ile Gln
                85                  90                  95

Asp Met Gln His Met Ala Gln Thr Leu Lys Ala Leu Ile His Cys Cys
                100                 105                 110

Ala Gly Asp Ala Leu Pro Asp Cys Pro Ile Leu His Thr Leu Gly Gln
                115                 120                 125

Pro Asp Asp Ser Glu Pro Glu Ala Arg Thr Gly Ala Val Leu Arg Arg
        130                 135                 140

Pro Arg Arg His Gly Leu Ala Lys Arg Leu
145                 150
```

<210> SEQ ID NO 29
<211> LENGTH: 154
<212> TYPE: PRT
<213> ORGANISM: Artificial Sequence

```
<220> FEATURE:
<223> OTHER INFORMATION: GolS-mt3-A38K V60L

<400> SEQUENCE: 29

Met Asn Ile Gly Lys Ala Ala Lys Ala Ser Lys Val Ser Ala Lys Met
1               5                   10                  15

Ile Arg Tyr Tyr Glu Gln Ile Gly Leu Ile Pro Ala Ala Ser Arg Thr
            20                  25                  30

Asp Ser Gly Tyr Arg Lys Tyr Thr Gln Ala Asp Val Asn Gln Leu His
        35                  40                  45

Phe Ile Arg Arg Ala Arg Asp Leu Gly Phe Ser Leu Ala Glu Ile Ser
    50                  55                  60

Asp Leu Leu Asn Leu Trp Asn Asn Gln Ser Arg Gln Ser Ala Asp Val
65                  70                  75                  80

Lys Arg Leu Ala Gln Thr His Ile Asp Glu Leu Asp Arg Arg Ile Gln
                85                  90                  95

Asn Met Gln His Met Ala Gln Thr Leu Lys Ala Leu Ile His Cys Cys
            100                 105                 110

Ala Gly Asp Ala Leu Pro Asp Cys Pro Ile Leu His Thr Leu Gly Gln
        115                 120                 125

Pro Asp Asp Ser Glu Pro Glu Ala Arg Thr Gly Ala Val Leu Arg Arg
    130                 135                 140

Pro Arg Arg His Gly Leu Ala Lys Arg Leu
145                 150

<210> SEQ ID NO 30
<211> LENGTH: 154
<212> TYPE: PRT
<213> ORGANISM: Artificial Sequence
<220> FEATURE:
<223> OTHER INFORMATION: GolS-mt4-D33P

<400> SEQUENCE: 30

Met Asn Ile Gly Lys Ala Ala Lys Ala Ser Lys Val Ser Ala Lys Met
1               5                   10                  15

Ile Arg Tyr Tyr Glu Gln Ile Gly Leu Ile Pro Ala Ala Ser Arg Thr
            20                  25                  30

Pro Ser Gly Tyr Arg Ala Tyr Thr Gln Ala Asp Val Asn Gln Leu His
        35                  40                  45

Phe Ile Arg Arg Ala Arg Asp Leu Gly Phe Ser Val Ala Glu Ile Ser
    50                  55                  60

Asp Leu Leu Asn Leu Trp Asn Asn Gln Ser Arg Gln Ser Ala Asp Val
65                  70                  75                  80

Lys Arg Leu Ala Gln Thr His Ile Asp Glu Leu Asp Arg Arg Ile Gln
                85                  90                  95

Asn Met Gln His Met Ala Gln Thr Leu Lys Ala Leu Ile His Cys Cys
            100                 105                 110

Ala Gly Asp Ala Leu Pro Asp Cys Pro Ile Leu His Thr Leu Gly Gln
        115                 120                 125

Pro Asp Asp Ser Glu Pro Glu Ala Arg Thr Gly Ala Val Leu Arg Arg
    130                 135                 140

Pro Arg Arg His Gly Leu Ala Lys Arg Leu
145                 150

<210> SEQ ID NO 31
<211> LENGTH: 200
<212> TYPE: PRT
```

-continued

```
<213> ORGANISM: Artificial Sequence
<220> FEATURE:
<223> OTHER INFORMATION: PhlF

<400> SEQUENCE: 31

Met Ala Arg Thr Pro Ser Arg Ser Ser Ile Gly Ser Leu Arg Ser Pro
1               5                   10                  15

His Thr His Lys Ala Ile Leu Thr Ser Thr Ile Glu Ile Leu Lys Glu
            20                  25                  30

Cys Gly Tyr Ser Gly Leu Ser Ile Glu Ser Val Ala Arg Arg Ala Gly
        35                  40                  45

Ala Ser Lys Pro Thr Ile Tyr Arg Trp Trp Thr Asn Lys Ala Ala Leu
    50                  55                  60

Ile Ala Glu Val Tyr Glu Asn Glu Ser Glu Gln Val Arg Lys Phe Pro
65                  70                  75                  80

Asp Leu Gly Ser Phe Lys Ala Asp Leu Asp Phe Leu Leu Arg Asn Leu
                85                  90                  95

Trp Lys Val Trp Arg Glu Thr Ile Cys Gly Glu Ala Phe Arg Cys Val
            100                 105                 110

Ile Ala Glu Ala Gln Leu Asp Pro Ala Thr Leu Thr Gln Leu Lys Asp
            115                 120                 125

Gln Phe Met Glu Arg Arg Arg Glu Met Pro Lys Lys Leu Val Glu Asn
    130                 135                 140

Ala Ile Ser Asn Gly Glu Leu Pro Lys Asp Thr Asn Arg Glu Leu Leu
145                 150                 155                 160

Leu Asp Met Ile Phe Gly Phe Cys Trp Tyr Arg Leu Leu Thr Glu Gln
                165                 170                 175

Leu Thr Val Glu Gln Asp Ile Glu Glu Phe Thr Phe Leu Leu Ile Asn
            180                 185                 190

Gly Val Cys Pro Gly Thr Gln Arg
            195                 200

<210> SEQ ID NO 32
<211> LENGTH: 51
<212> TYPE: DNA
<213> ORGANISM: Artificial Sequence
<220> FEATURE:
<223> OTHER INFORMATION: phlF operator

<400> SEQUENCE: 32
tctgattcgt taccaattga catgatacga aacgtaccgt atcgttaagg t          51

<210> SEQ ID NO 33
<211> LENGTH: 1404
<212> TYPE: DNA
<213> ORGANISM: Artificial Sequence
<220> FEATURE:
<223> OTHER INFORMATION: merA nucleic acid sequence

<400> SEQUENCE: 33
atggaaccgc cggttcaggt agccgtgatt ggctccggtg gggctgccat ggcagccgca     60
ctgaaagccg tggaacaggg ggctcaggtt acgctgatcg agcgtggcac gattggcgga    120
acctgcgtta acgttggctg tgtgccgagt aaaatcatga ttcgcgcggc gcacattgca    180
catttgcgtc gtgagtcccc gttcgatggc ggtattgcgg ccactgtacc gacgattgac    240
cgcagcaaac tgttagcgca gcaacaggcc cgcgtcgatg aactgcgtca tgccaaatac    300
gagggtatcc tgggcgggaa cccggccatt accgtagtac atggagaggc ccgtttaa     360
```

```
gatgatcaat ctctgacggt gcgcttgaat gaaggcggtg aacgcgtggt aatgtttgac      420
cgctgcttag ttgccacagg cgcgtcaccg gcggttccgc cgatcccagg actgaaggaa      480
agcccctact ggaccagcac cgaagcactg gcatcggata cgatcccgga acgtttggca      540
gtgatcgggt cttcggtagt ggcactggag ttagcccagg cgttcgcgcg tctgggggtct    600 aaagttaccg tcttagcacg taacacgctg tttttccgcg aagatccggc cattggtgag      660
gcagttacag cagcgttccg cgctgaaggt attgaggttc ttgaacatac tcaggcaagc      720
caagtggcgc atatggatgg cgaatttgta ctgacaacaa cccacgggga actgcgtgcg      780
gataaactgc tggtggcgac aggccgcacg cccaacacac gcagtctggc gctggatgcg      840
gctggtgtca ccgtcaatgc gcagggtgca attgtgatcg accagggtat gcgcacgtct      900
aatccgaaca tttatgcagc cggtgattgt acagatcaac cgcagttcgt gtatgttgcg      960
gctgccgcag gaacgcgtgc ggccattaat atgaccggtg gtgatgccgc gttagatctg     1020
acagctatgc cggccgtggt attcactgat ccgcaggttg ccaccgtcgg ttattccgaa     1080
gccgaagctc accatgatgg tatcgaaacc gattcacgta ctcttacgct cgacaatgta     1140
ccccgtgctc ttgcgaactt tgatacccgc gggtttatta agctcgtgat tgaggagggg     1200
tcgcatcgct taattggtgt ccaggcagtg gccccggagg cggggggagct gattcagacc     1260 gccgcgttgg cgattcgcaa ccgcatgaca gtccaagaac tcgcggatca gctgtttccg     1320
tacctgacaa tggtcgaagg actgaaactg gccgcgcaaa cgtttaataa agatgtcaaa     1380
caattgtcgt gctgtgcagg ctaa                                           1404
```

<210> SEQ ID NO 34
<211> LENGTH: 467
<212> TYPE: PRT
<213> ORGANISM: Artificial Sequence
<220> FEATURE:
<223> OTHER INFORMATION: MerA amino acid sequence

<400> SEQUENCE: 34

```
Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
            20                  25                  30

Ile Glu Arg Gly Thr Ile Gly Gly Thr Cys Val Asn Val Gly Cys Val
        35                  40                  45

Pro Ser Lys Ile Met Ile Arg Ala Ala His Ile Ala His Leu Arg Arg
    50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
        115                 120                 125

Leu Asn Glu Gly Gly Glu Arg Val Val Met Phe Asp Arg Cys Leu Val
    130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175
```

```
Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
            195                 200                 205

Thr Leu Phe Phe Arg Glu Asp Pro Ala Ile Gly Glu Ala Val Thr Ala
            210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
            275                 280                 285

Gly Ala Ile Val Ile Asp Gln Gly Met Arg Thr Ser Asn Pro Asn Ile
            290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
                325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
            355                 360                 365

Glu Thr Asp Ser Arg Thr Leu Thr Leu Asp Asn Val Pro Arg Ala Leu
            370                 375                 380

Ala Asn Phe Asp Thr Arg Gly Phe Ile Lys Leu Val Ile Glu Glu Gly
385                 390                 395                 400

Ser His Arg Leu Ile Gly Val Gln Ala Val Ala Pro Glu Ala Gly Glu
                405                 410                 415

Leu Ile Gln Thr Ala Ala Leu Ala Ile Arg Asn Arg Met Thr Val Gln
            420                 425                 430

Glu Leu Ala Asp Gln Leu Phe Pro Tyr Leu Thr Met Val Glu Gly Leu
            435                 440                 445

Lys Leu Ala Ala Gln Thr Phe Asn Lys Asp Val Lys Gln Leu Ser Cys
    450                 455                 460

Cys Ala Gly
465

<210> SEQ ID NO 35
<211> LENGTH: 2976
<212> TYPE: DNA
<213> ORGANISM: Artificial Sequence
<220> FEATURE:
<223> OTHER INFORMATION: hcnABC

<400> SEQUENCE: 35
atgtccttac atcgcagtca cgatatccag gcattgcagg gccagaccct gacgatacac      60
atcaatgatc aaccggtcgc cgcggcaagc ggcgaaaccg tgctcagcgt cctcaacgcc     120
gtcggcctgc ccagctcag ccgcaacgac aaccagcaga tcgccggctc ctattgcggg      180
atgggggtct gccactgctg cctggtcaag atagacggcc gccacaagcg ccgcgcctgc     240
cagaccgtgg tccgccccgg catgaaggtg gaaaccgcca gcaaccgtct gaatacggag     300
ggtttgcaat gagcgccaaa cccgtcatcg taggcggcgg cccggccggc atgtcggccg     360
```

```
ccatggagct ggcgcgccac ggcgtggagt gcgtgctgct ggacgaggcc tcccgcgtgg      420
gcggcgtggt ctatcgcggc ccgctgcggg aaggcgtggt gctggactac ctgggcgagc      480
gctatcgcga aaacatgcag gcgctgcacc gcgaattcga acaagtccgc gaccgcatcg      540
acatccggct gaacacccgc gtcgtcggcg gcggagaggg cgaactgttc gcgctgacgc      600
cggacgagcg agtcgaggcc gtccccttt cccagctgct gctggccgcc ggctgccatg      660
agcgcagcgt gcccttcccc ggctggaccc tgcccggcgt gatcatgctg ggcggcctgc      720
agcttcagat caagagcggc gtggtcaagc cgctggggcg caccgtgctg gtcggcaccg      780
gcccgctgtt gccgctggtg gcgtgccagc tgcaccgcgc cggcgtggaa gtggccggcg      840
tttacgaagc cagcgccttc ggccggctgg ccaaggaaac gatcgccctg ctcaaccaac      900
cgcagctgtt cctggacggc ctgagcatgg tggcctacct gaagcgccac ggcatcccgc      960
tgcactacgg ctggggcgtg gtcgaggccc acggcgacgc cgagctgggc gaagtgaccg     1020
tcgcgcccta cgacgcggaa tggcgcgccg acctgacgcg cagccgccgc ctgccggcgc     1080
agacgctggc cgtcggctac ggcttcatcc cgcgcaccca gctgacccag cagatgggcc     1140
tggagcaccg ctacgccgac gacggctacc tgaagccggt caacgacgaa tggcagcgca     1200
gcagccgcgc caacatccac ctggccggcg acatcggcgg cctgcgcggc ggcgaagcgg     1260
cgatgatcag cggccgcatc gccgcgctgt ccatgctgct gcagctgggc aagctggacg     1320
agcaacaggc gctgcgccaa cgccaggcat gcctggacca gatggcgtcc atcctgcgct     1380
tccgcaaggg catagacagc ttcacccgcc gcggccgcgg ccagttggcg ctgccggcgc     1440
gcgacaccgt gatctgccgc tgcgagcacg ccacccgcca ggacatcgac accgcgctgg     1500
aacagggcgt caacgacctg atcagcctga agatgcgcac ccgggtcagc atgggcgact     1560
gccagggcaa gatgtgcgtc ggctattgca gcgaccgcct gcgcgagcac accggcaagc     1620
gcgacgtggg ctggatacgc ccgcgcttcc cgctggaccc gctgccgttc tcggccttct     1680
ccgccatcga cgcccaacag actgaagaga tttgacatga gcaagcaata cgacatcgtg     1740
atcgccggcg gcggcgtgat cggcgcctcc tgcgcctacc agctgtccaa gcgccgcgat     1800
ctgaaaatcg cgctgatcga cagcaagcgt cccggcaacg cgtcgcgcgc gtcggccggc     1860
ggcctgtggg cgataggcga gtcggtgggc ctgggctgcg gcgtgatctt cttccgcatg     1920
acctcggcca agcgcaagcg cgaggcggcc ggcgcggcgg tggcggtgga cgccagcacg     1980
ccgcacatcc tgccgcagag cttcttcgac ttcgcgctgg cctccaacgc gctgtacccg     2040
gccctgcacc aggaactgat ggaaaaccac ggcatggact tcaagttcga gcgcaccggg     2100
ctcaagtaca tcatttacga tgaagaagac cagctgtacg ccgagcacat cgccgcccag     2160
attccgcacc tggccagcga ggtgagctgg ctggaccgcg cccagctgcg cgagagcgag     2220
ccctatgtca gcggcgaggc gcaaggcgcg ctggaattcc tgtgcgacca tcaggtcagc     2280
ccgttccgcc tgaccgacgc ctacaccgag gcggcgcggc aaaacggcgt cgacgtgttc     2340
ttcaacgtca acgtcaccgg cgtcacccgc cagggcagcc gcgtgaccgg cgtgcgcacc     2400
gccgaggccg gcgatttctc ttgcaatacg ctgatcaacg ccggcggctc ctgggcggcc     2460
gagctgtcgc gctgggccac cggccgcacc atcccggtca gccggtcaa gggccagatc     2520 gtgctgtcgg agaagatgcc caagctcttg cgcggctgca tcaccaccag cgactgctac     2580
atcgcgcaga aggacaacgg cgagatcctg atcggcagca ccaccgagga caagggctac     2640
gacaccgcca tcacctatcc ggaaatcaac ggactggtgc agggcgcgat acgctgcgtg     2700
ccggagctcg ccaacgtcaa catcaagcgt tgctgggcag gcctgcgccc cggcacgccc     2760
```

-continued

```
gacgagctgc ctatcctggg gccggaagac ggcgtcgagg ggtatctgaa cgcctgcggc    2820
cacttccgca ccggcatcct cacctcggcc atcaccgggg tgctgctgaa cgggctggtg    2880
cgcggcgagc cgctgccgct ggacatcgcg cccttcctgg ccggccgctt ccctaaccgc    2940
accgaaaaag aaatggattt cgcgctgcac gcctga                             2976
```

```
<210> SEQ ID NO 36
<211> LENGTH: 1233
<212> TYPE: DNA
<213> ORGANISM: Artificial Sequence
<220> FEATURE:
<223> OTHER INFORMATION: serA

<400> SEQUENCE: 36
atggcaaagg tatcgctgga gaaagacaag attaagtttc tgctggtaga aggcgtgcac      60
caaaaggcgc tggaaagcct tcgtgcagct ggttacacca acatcgaatt tcacaaaggc     120
gcgctggatg atgaacaatt aaaagaatcc atccgcgatg cccacttcat cggcctgcga     180
tcccgtaccc atctgactga agacgtgatc aacgccgcag aaaaactggt cgctattggc     240
tgtttctgta tcggaacaaa ccaggttgat ctggatgcgg cggcaaagcg cgggatcccg     300
gtatttaacg caccgttctc aaatacgcgc tctgttgcgg agctggtgat tggcgaactg     360
ctgctgctat tgcgcggcgt gccggaagcc aatgctaaag cgcaccgtgg cgtgtggaac     420
aaactggcgg cgggttcttt tgaagcgcgc ggcaaaaagc tgggtatcat cggctacggt     480
catattggta cgcaattggg cattctggct gaatcgctgg gaatgtatgt ttacttttat     540
gatattgaaa ataaactgcc gctgggcaac gccactcagg tacagcatct ttctgacctg     600
ctgaatatga gcgatgtggt gagtctgcat gtaccagaga atccgtccac caaaaatatg     660
atgggcgcga agaaatttc actaatgaag cccggctcgc tgctgattaa tgcttcgcgc     720
ggtactgtgg tggatattcc ggcgctgtgt gatgcgctgg cgagcaaaca tctggcgggg     780
gcggcaatcg acgtattccc gacggaaccg gcgaccaata gcgatccatt tacctctccg     840
ctgtgtgaat tcgacaacgt ccttctgacg ccacacattg gcggttcgac tcaggaagcg     900
caggagaata tcggcctgga agttgcgggt aaattgatca gtattctga caatggctca     960 acgctctctg cggtgaactt cccggaagtc tcgctgccac tgcacggtgg gcgtcgtctg    1020
atgcacatcg ccgaagcccg tccgggcgtg ctaactgcgc tgaacaaaat cttcgccgag    1080
cagggcgtca acatcgccgc gcaatatctg caaacttccg cccagatggg ttatgtggtt    1140
attgatattg aagccgacga agacgttgcc gaaaaagcgc tgcaggcaat gaaagctatt    1200
ccgggtacca ttcgcgcccg tctgctgtac taa                               1233
```

```
<210> SEQ ID NO 37
<211> LENGTH: 35
<212> TYPE: DNA
<213> ORGANISM: Artificial Sequence
<220> FEATURE:
<223> OTHER INFORMATION: PCon6

<400> SEQUENCE: 37
ctgatggcta gctcagtcct aggattatg ctagc                                 35
```

```
<210> SEQ ID NO 38
<211> LENGTH: 467
<212> TYPE: PRT
<213> ORGANISM: Artificial Sequence
<220> FEATURE:
```

<223> OTHER INFORMATION: DM1 P49I

<400> SEQUENCE: 38

```
Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
            20                  25                  30

Ile Glu Arg Gly Thr Ile Gly Gly Thr Cys Val Asn Val Gly Cys Val
            35                  40                  45

Ile Ser Lys Ile Met Ile Arg Ala Ala His Ile Ala His Leu Arg Arg
        50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
        115                 120                 125

Leu Asn Glu Gly Gly Glu Arg Val Val Met Phe Asp Arg Cys Leu Val
        130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
        195                 200                 205

Thr Leu Phe Phe Arg Glu Asp Pro Ala Ile Gly Glu Ala Val Thr Ala
        210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
        275                 280                 285

Gly Ala Ile Val Ile Asp Gln Gly Met Arg Thr Ser Asn Pro Asn Ile
        290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
            325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
        355                 360                 365

Glu Thr Asp Ser Arg Thr Leu Thr Leu Asp Asn Val Pro Arg Ala Leu
        370                 375                 380

Ala Asn Phe Asp Thr Arg Gly Phe Ile Lys Leu Val Ile Glu Glu Gly
385                 390                 395                 400
```

-continued

```
Ser His Arg Leu Ile Gly Val Gln Ala Val Ala Pro Glu Ala Gly Glu
            405                 410                 415

Leu Ile Gln Thr Ala Ala Leu Ala Ile Arg Asn Arg Met Thr Val Gln
            420                 425                 430

Glu Leu Ala Asp Gln Leu Phe Pro Tyr Leu Thr Met Val Glu Gly Leu
            435                 440                 445

Lys Leu Ala Ala Gln Thr Phe Asn Lys Asp Val Lys Gln Leu Ser Cys
        450                 455                 460

Cys Ala Gly
465

<210> SEQ ID NO 39
<211> LENGTH: 467
<212> TYPE: PRT
<213> ORGANISM: Artificial Sequence
<220> FEATURE:
<223> OTHER INFORMATION: DM2 I293F

<400> SEQUENCE: 39

Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
            20                  25                  30

Ile Glu Arg Gly Thr Ile Gly Gly Thr Cys Val Asn Val Gly Cys Val
            35                  40                  45

Pro Ser Lys Ile Met Ile Arg Ala Ala His Ile Ala His Leu Arg Arg
        50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
            115                 120                 125

Leu Asn Glu Gly Gly Glu Arg Val Val Met Phe Asp Arg Cys Leu Val
            130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
            195                 200                 205

Thr Leu Phe Phe Arg Glu Asp Pro Ala Ile Gly Glu Ala Val Thr Ala
            210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
            275                 280                 285
```

```
Gly Ala Ile Val Phe Asp Gln Gly Met Arg Thr Ser Asn Pro Asn Ile
    290             295             300

Tyr Ala Ala Gly Asp Cys Thr Asp Gln Pro Gln Phe Val Tyr Val Ala
305             310             315             320

Ala Ala Ala Gly Thr Arg Ala Ala Ile Asn Met Thr Gly Gly Asp Ala
            325             330             335

Ala Leu Asp Leu Thr Ala Met Pro Ala Val Val Phe Thr Asp Pro Gln
            340             345             350

Val Ala Thr Val Gly Tyr Ser Glu Ala Glu Ala His His Asp Gly Ile
            355             360             365

Glu Thr Asp Ser Arg Thr Leu Thr Leu Asp Asn Val Pro Arg Ala Leu
    370             375             380

Ala Asn Phe Asp Thr Arg Gly Phe Ile Lys Leu Val Ile Glu Glu Gly
385             390             395             400

Ser His Arg Leu Ile Gly Val Gln Ala Val Ala Pro Glu Ala Gly Glu
            405             410             415

Leu Ile Gln Thr Ala Ala Leu Ala Ile Arg Asn Arg Met Thr Val Gln
            420             425             430

Glu Leu Ala Asp Gln Leu Phe Pro Tyr Leu Thr Met Val Glu Gly Leu
            435             440             445

Lys Leu Ala Ala Gln Thr Phe Asn Lys Asp Val Lys Gln Leu Ser Cys
    450             455             460

Cys Ala Gly
465
```

```
<210> SEQ ID NO 40
<211> LENGTH: 467
<212> TYPE: PRT
<213> ORGANISM: Artificial Sequence
<220> FEATURE:
<223> OTHER INFORMATION: DM3 T299R

<400> SEQUENCE: 40
```

```
Met Glu Pro Pro Val Gln Val Ala Val Ile Gly Ser Gly Gly Ala Ala
1               5               10              15

Met Ala Ala Ala Leu Lys Ala Val Glu Gln Gly Ala Gln Val Thr Leu
            20              25              30

Ile Glu Arg Gly Thr Ile Gly Gly Thr Cys Val Asn Val Gly Cys Val
            35              40              45

Pro Ser Lys Ile Met Ile Arg Ala Ala His Ile Ala His Leu Arg Arg
    50              55              60

Glu Ser Pro Phe Asp Gly Gly Ile Ala Ala Thr Val Pro Thr Ile Asp
65              70              75              80

Arg Ser Lys Leu Leu Ala Gln Gln Ala Arg Val Asp Glu Leu Arg
            85              90              95

His Ala Lys Tyr Glu Gly Ile Leu Gly Gly Asn Pro Ala Ile Thr Val
            100             105             110

Val His Gly Glu Ala Arg Phe Lys Asp Asp Gln Ser Leu Thr Val Arg
            115             120             125

Leu Asn Glu Gly Gly Glu Arg Val Val Met Phe Asp Arg Cys Leu Val
            130             135             140

Ala Thr Gly Ala Ser Pro Ala Val Pro Pro Ile Pro Gly Leu Lys Glu
145             150             155             160

Ser Pro Tyr Trp Thr Ser Thr Glu Ala Leu Ala Ser Asp Thr Ile Pro
                165             170             175
```

-continued

```
Glu Arg Leu Ala Val Ile Gly Ser Ser Val Val Ala Leu Glu Leu Ala
            180             185             190

Gln Ala Phe Ala Arg Leu Gly Ser Lys Val Thr Val Leu Ala Arg Asn
            195             200             205

Thr Leu Phe Phe Arg Glu Asp Pro Ala Ile Gly Glu Ala Val Thr Ala
        210             215             220

Ala Phe Arg Ala Glu Gly Ile Glu Val Leu Glu His Thr Gln Ala Ser
225             230             235             240

Gln Val Ala His Met Asp Gly Glu Phe Val Leu Thr Thr Thr His Gly
            245             250             255

Glu Leu Arg Ala Asp Lys Leu Leu Val Ala Thr Gly Arg Thr Pro Asn
            260             265             270

Thr Arg Ser Leu Ala Leu Asp Ala Ala Gly Val Thr Val Asn Ala Gln
            275             280             285

Gly Ala Ile Val Ile Asp Gln Gly Met Arg Arg Ser Asn Pro Asn Ile
            290             295             300

Tyr Ala Ala Gly Asp Cys Thr Asp Gln Pro Gln Phe Val Tyr Val Ala
305             310             315             320

Ala Ala Ala Gly Thr Arg Ala Ala Ile Asn Met Thr Gly Gly Asp Ala
            325             330             335

Ala Leu Asp Leu Thr Ala Met Pro Ala Val Val Phe Thr Asp Pro Gln
            340             345             350

Val Ala Thr Val Gly Tyr Ser Glu Ala Glu Ala His His Asp Gly Ile
            355             360             365

Glu Thr Asp Ser Arg Thr Leu Thr Leu Asp Asn Val Pro Arg Ala Leu
            370             375             380

Ala Asn Phe Asp Thr Arg Gly Phe Ile Lys Leu Val Ile Glu Glu Gly
385             390             395             400

Ser His Arg Leu Ile Gly Val Gln Ala Val Ala Pro Glu Ala Gly Glu
            405             410             415

Leu Ile Gln Thr Ala Ala Leu Ala Ile Arg Asn Arg Met Thr Val Gln
            420             425             430

Glu Leu Ala Asp Gln Leu Phe Pro Tyr Leu Thr Met Val Glu Gly Leu
            435             440             445

Lys Leu Ala Ala Gln Thr Phe Asn Lys Asp Val Lys Gln Leu Ser Cys
    450             455             460

Cys Ala Gly
465
```

```
<210> SEQ ID NO 41
<211> LENGTH: 467
<212> TYPE: PRT
<213> ORGANISM: Artificial Sequence
<220> FEATURE:
<223> OTHER INFORMATION: DM4 A323D

<400> SEQUENCE: 41

Met Glu Pro Pro Val Gln Val Ala Val Ile Gly Ser Gly Gly Ala Ala
1               5               10              15

Met Ala Ala Ala Leu Lys Ala Val Glu Gln Gly Ala Gln Val Thr Leu
            20              25              30

Ile Glu Arg Gly Thr Ile Gly Gly Thr Cys Val Asn Val Gly Cys Val
            35              40              45

Pro Ser Lys Ile Met Ile Arg Ala Ala His Ile Ala His Leu Arg Arg
    50              55              60
```

```
Glu Ser Pro Phe Asp Gly Gly Ile Ala Ala Thr Val Pro Thr Ile Asp
65              70              75              80

Arg Ser Lys Leu Leu Ala Gln Gln Gln Ala Arg Val Asp Glu Leu Arg
            85              90              95

His Ala Lys Tyr Glu Gly Ile Leu Gly Gly Asn Pro Ala Ile Thr Val
            100             105             110

Val His Gly Glu Ala Arg Phe Lys Asp Asp Gln Ser Leu Thr Val Arg
        115             120             125

Leu Asn Glu Gly Gly Glu Arg Val Val Met Phe Asp Arg Cys Leu Val
        130             135             140

Ala Thr Gly Ala Ser Pro Ala Val Pro Pro Ile Pro Gly Leu Lys Glu
145             150             155             160

Ser Pro Tyr Trp Thr Ser Thr Glu Ala Leu Ala Ser Asp Thr Ile Pro
                165             170             175

Glu Arg Leu Ala Val Ile Gly Ser Ser Val Val Ala Leu Glu Leu Ala
            180             185             190

Gln Ala Phe Ala Arg Leu Gly Ser Lys Val Thr Val Leu Ala Arg Asn
            195             200             205

Thr Leu Phe Phe Arg Glu Asp Pro Ala Ile Gly Glu Ala Val Thr Ala
    210             215             220

Ala Phe Arg Ala Glu Gly Ile Glu Val Leu Glu His Thr Gln Ala Ser
225             230             235             240

Gln Val Ala His Met Asp Gly Glu Phe Val Leu Thr Thr Thr His Gly
            245             250             255

Glu Leu Arg Ala Asp Lys Leu Leu Val Ala Thr Gly Arg Thr Pro Asn
            260             265             270

Thr Arg Ser Leu Ala Leu Asp Ala Ala Gly Val Thr Val Asn Ala Gln
            275             280             285

Gly Ala Ile Val Ile Asp Gln Gly Met Arg Thr Ser Asn Pro Asn Ile
            290             295             300

Tyr Ala Ala Gly Asp Cys Thr Asp Gln Pro Gln Phe Val Tyr Val Ala
305             310             315             320

Ala Ala Asp Gly Thr Arg Ala Ala Ile Asn Met Thr Gly Gly Asp Ala
            325             330             335

Ala Leu Asp Leu Thr Ala Met Pro Ala Val Val Phe Thr Asp Pro Gln
            340             345             350

Val Ala Thr Val Gly Tyr Ser Glu Ala Glu Ala His His Asp Gly Ile
            355             360             365

Glu Thr Asp Ser Arg Thr Leu Thr Leu Asp Asn Val Pro Arg Ala Leu
    370             375             380

Ala Asn Phe Asp Thr Arg Gly Phe Ile Lys Leu Val Ile Glu Glu Gly
385             390             395             400

Ser His Arg Leu Ile Gly Val Gln Ala Val Ala Pro Glu Ala Gly Glu
            405             410             415

Leu Ile Gln Thr Ala Ala Leu Ala Ile Arg Asn Arg Met Thr Val Gln
            420             425             430

Glu Leu Ala Asp Gln Leu Phe Pro Tyr Leu Thr Met Val Glu Gly Leu
            435             440             445

Lys Leu Ala Ala Gln Thr Phe Asn Lys Asp Val Lys Gln Leu Ser Cys
    450             455             460

Cys Ala Gly
465
```

```
<210> SEQ ID NO 42
<211> LENGTH: 425
<212> TYPE: PRT
<213> ORGANISM: Artificial Sequence
<220> FEATURE:
<223> OTHER INFORMATION: DM5 A323D (del324 - 365)

<400> SEQUENCE: 42

Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
                20                  25                  30

Ile Glu Arg Gly Thr Ile Gly Gly Thr Cys Val Asn Val Gly Cys Val
            35                  40                  45

Pro Ser Lys Ile Met Ile Arg Ala Ala His Ile Ala His Leu Arg Arg
        50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
        115                 120                 125

Leu Asn Glu Gly Gly Glu Arg Val Val Met Phe Asp Arg Cys Leu Val
        130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
        195                 200                 205

Thr Leu Phe Phe Arg Glu Asp Pro Ala Ile Gly Glu Ala Val Thr Ala
        210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
        275                 280                 285

Gly Ala Ile Val Ile Asp Gln Gly Met Arg Thr Ser Asn Pro Asn Ile
        290                 295                 300

Tyr Ala Ala Gly Asp Cys Thr Asp Gln Pro Gln Phe Val Tyr Val Ala
305                 310                 315                 320

Ala Ala Asp Asp Gly Ile Glu Thr Asp Ser Arg Thr Leu Thr Leu Asp
                325                 330                 335

Asn Val Pro Arg Ala Leu Ala Asn Phe Asp Thr Arg Gly Phe Ile Lys
            340                 345                 350

Leu Val Ile Glu Glu Gly Ser His Arg Leu Ile Gly Val Gln Ala Val
        355                 360                 365

Ala Pro Glu Ala Gly Glu Leu Ile Gln Thr Ala Ala Leu Ala Ile Arg
```

-continued

```
        370              375              380

Asn Arg Met Thr Val Gln Glu Leu Ala Asp Gln Leu Phe Pro Tyr Leu
385                  390                  395                  400

Thr Met Val Glu Gly Leu Lys Leu Ala Ala Gln Thr Phe Asn Lys Asp
                    405                  410                  415

Val Lys Gln Leu Ser Cys Cys Ala Gly
                420                  425

<210> SEQ ID NO 43
<211> LENGTH: 467
<212> TYPE: PRT
<213> ORGANISM: Artificial Sequence
<220> FEATURE:
<223> OTHER INFORMATION: DM6 L395D

<400> SEQUENCE: 43

Met Glu Pro Pro Val Gln Val Ala Val Ile Gly Ser Gly Gly Ala Ala
1               5                  10                  15

Met Ala Ala Ala Leu Lys Ala Val Glu Gln Gly Ala Gln Val Thr Leu
                20                  25                  30

Ile Glu Arg Gly Thr Ile Gly Gly Thr Cys Val Asn Val Gly Cys Val
            35                  40                  45

Pro Ser Lys Ile Met Ile Arg Ala Ala His Ile Ala His Leu Arg Arg
        50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
                100                 105                 110

Val His Gly Glu Ala Arg Phe Lys Asp Asp Gln Ser Leu Thr Val Arg
            115                 120                 125

Leu Asn Glu Gly Gly Glu Arg Val Val Met Phe Asp Arg Cys Leu Val
        130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
                180                 185                 190

Gln Ala Phe Ala Arg Leu Gly Ser Lys Val Thr Val Leu Ala Arg Asn
            195                 200                 205

Thr Leu Phe Phe Arg Glu Asp Pro Ala Ile Gly Glu Ala Val Thr Ala
        210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
                260                 265                 270

Thr Arg Ser Leu Ala Leu Asp Ala Ala Gly Val Thr Val Asn Ala Gln
            275                 280                 285

Gly Ala Ile Val Ile Asp Gln Gly Met Arg Thr Ser Asn Pro Asn Ile
        290                 295                 300

Tyr Ala Ala Gly Asp Cys Thr Asp Gln Pro Gln Phe Val Tyr Val Ala
```

-continued

```
305                310                315                320

Ala Ala Ala Gly Thr Arg Ala Ala Ile Asn Met Thr Gly Gly Asp Ala
              325            330            335

Ala Leu Asp Leu Thr Ala Met Pro Ala Val Val Phe Thr Asp Pro Gln
              340            345            350

Val Ala Thr Val Gly Tyr Ser Glu Ala Glu Ala His His Asp Gly Ile
              355            360            365

Glu Thr Asp Ser Arg Thr Leu Thr Leu Asp Asn Val Pro Arg Ala Leu
              370            375            380

Ala Asn Phe Asp Thr Arg Gly Phe Ile Lys Asp Val Ile Glu Glu Gly
385            390            395            400

Ser His Arg Leu Ile Gly Val Gln Ala Val Ala Pro Glu Ala Gly Glu
              405            410            415

Leu Ile Gln Thr Ala Ala Leu Ala Ile Arg Asn Arg Met Thr Val Gln
              420            425            430

Glu Leu Ala Asp Gln Leu Phe Pro Tyr Leu Thr Met Val Glu Gly Leu
              435            440            445

Lys Leu Ala Ala Gln Thr Phe Asn Lys Asp Val Lys Gln Leu Ser Cys
     450            455            460

Cys Ala Gly
465

<210> SEQ ID NO 44
<211> LENGTH: 467
<212> TYPE: PRT
<213> ORGANISM: Artificial Sequence
<220> FEATURE:
<223> OTHER INFORMATION: DM7 G406D

<400> SEQUENCE: 44

Met Glu Pro Pro Val Gln Val Ala Val Ile Gly Ser Gly Gly Ala Ala
1               5               10              15

Met Ala Ala Ala Leu Lys Ala Val Glu Gln Gly Ala Gln Val Thr Leu
              20              25              30

Ile Glu Arg Gly Thr Ile Gly Gly Thr Cys Val Asn Val Gly Cys Val
         35              40              45

Pro Ser Lys Ile Met Ile Arg Ala Ala His Ile Ala His Leu Arg Arg
     50              55              60

Glu Ser Pro Phe Asp Gly Gly Ile Ala Ala Thr Val Pro Thr Ile Asp
65              70              75              80

Arg Ser Lys Leu Leu Ala Gln Gln Ala Arg Val Asp Glu Leu Arg
              85              90              95

His Ala Lys Tyr Glu Gly Ile Leu Gly Gly Asn Pro Ala Ile Thr Val
              100             105             110

Val His Gly Glu Ala Arg Phe Lys Asp Asp Gln Ser Leu Thr Val Arg
         115             120             125

Leu Asn Glu Gly Gly Glu Arg Val Val Met Phe Asp Arg Cys Leu Val
     130             135             140

Ala Thr Gly Ala Ser Pro Ala Val Pro Pro Ile Pro Gly Leu Lys Glu
145             150             155             160

Ser Pro Tyr Trp Thr Ser Thr Glu Ala Leu Ala Ser Asp Thr Ile Pro
              165             170             175

Glu Arg Leu Ala Val Ile Gly Ser Ser Val Val Ala Leu Glu Leu Ala
         180             185             190

Gln Ala Phe Ala Arg Leu Gly Ser Lys Val Thr Val Leu Ala Arg Asn
```

```
                195                 200                 205

Thr Leu Phe Phe Arg Glu Asp Pro Ala Ile Gly Glu Ala Val Thr Ala
    210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
            275                 280                 285

Gly Ala Ile Val Ile Asp Gln Gly Met Arg Thr Ser Asn Pro Asn Ile
        290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
                325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
            355                 360                 365

Glu Thr Asp Ser Arg Thr Leu Thr Leu Asp Asn Val Pro Arg Ala Leu
        370                 375                 380

Ala Asn Phe Asp Thr Arg Gly Phe Ile Lys Leu Val Ile Glu Glu Gly
385                 390                 395                 400

Ser His Arg Leu Ile Asp Val Gln Ala Val Ala Pro Glu Ala Gly Glu
                405                 410                 415

Leu Ile Gln Thr Ala Ala Leu Ala Ile Arg Asn Arg Met Thr Val Gln
            420                 425                 430

Glu Leu Ala Asp Gln Leu Phe Pro Tyr Leu Thr Met Val Glu Gly Leu
            435                 440                 445

Lys Leu Ala Ala Gln Thr Phe Asn Lys Asp Val Lys Gln Leu Ser Cys
    450                 455                 460

Cys Ala Gly
465
```

```
<210> SEQ ID NO 45
<211> LENGTH: 467
<212> TYPE: PRT
<213> ORGANISM: Artificial Sequence
<220> FEATURE:
<223> OTHER INFORMATION: DM8 A411Q

<400> SEQUENCE: 45

Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
            20                  25                  30

Ile Glu Arg Gly Thr Ile Gly Gly Thr Cys Val Asn Val Gly Cys Val
        35                  40                  45

Pro Ser Lys Ile Met Ile Arg Ala Ala His Ile Ala His Leu Arg Arg
    50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
```

```
                    85              90              95
His Ala Lys Tyr Glu Gly Ile Leu Gly Gly Asn Pro Ala Ile Thr Val
            100             105             110

Val His Gly Glu Ala Arg Phe Lys Asp Asp Gln Ser Leu Thr Val Arg
            115             120             125

Leu Asn Glu Gly Gly Glu Arg Val Val Met Phe Asp Arg Cys Leu Val
            130             135             140

Ala Thr Gly Ala Ser Pro Ala Val Pro Pro Ile Pro Gly Leu Lys Glu
145             150             155             160

Ser Pro Tyr Trp Thr Ser Thr Glu Ala Leu Ala Ser Asp Thr Ile Pro
                165             170             175

Glu Arg Leu Ala Val Ile Gly Ser Ser Val Val Ala Leu Glu Leu Ala
            180             185             190

Gln Ala Phe Ala Arg Leu Gly Ser Lys Val Thr Val Leu Ala Arg Asn
            195             200             205

Thr Leu Phe Phe Arg Glu Asp Pro Ala Ile Gly Glu Ala Val Thr Ala
            210             215             220

Ala Phe Arg Ala Glu Gly Ile Glu Val Leu Glu His Thr Gln Ala Ser
225             230             235             240

Gln Val Ala His Met Asp Gly Glu Phe Val Leu Thr Thr Thr His Gly
                245             250             255

Glu Leu Arg Ala Asp Lys Leu Leu Val Ala Thr Gly Arg Thr Pro Asn
            260             265             270

Thr Arg Ser Leu Ala Leu Asp Ala Ala Gly Val Thr Val Asn Ala Gln
            275             280             285

Gly Ala Ile Val Ile Asp Gln Gly Met Arg Thr Ser Asn Pro Asn Ile
            290             295             300

Tyr Ala Ala Gly Asp Cys Thr Asp Gln Pro Gln Phe Val Tyr Val Ala
305             310             315             320

Ala Ala Ala Gly Thr Arg Ala Ala Ile Asn Met Thr Gly Gly Asp Ala
                325             330             335

Ala Leu Asp Leu Thr Ala Met Pro Ala Val Val Phe Thr Asp Pro Gln
            340             345             350

Val Ala Thr Val Gly Tyr Ser Glu Ala Glu Ala His His Asp Gly Ile
            355             360             365

Glu Thr Asp Ser Arg Thr Leu Thr Leu Asp Asn Val Pro Arg Ala Leu
            370             375             380

Ala Asn Phe Asp Thr Arg Gly Phe Ile Lys Leu Val Ile Glu Glu Gly
385             390             395             400

Ser His Arg Leu Ile Gly Val Gln Ala Val Gln Pro Glu Ala Gly Glu
                405             410             415

Leu Ile Gln Thr Ala Ala Leu Ala Ile Arg Asn Arg Met Thr Val Gln
            420             425             430

Glu Leu Ala Asp Gln Leu Phe Pro Tyr Leu Thr Met Val Glu Gly Leu
            435             440             445

Lys Leu Ala Ala Gln Thr Phe Asn Lys Asp Val Lys Gln Leu Ser Cys
    450             455             460

Cys Ala Gly
465
```

<210> SEQ ID NO 46
<211> LENGTH: 467
<212> TYPE: PRT
<213> ORGANISM: Artificial Sequence -continued

```
<220> FEATURE:
<223> OTHER INFORMATION: DM9 A411C

<400> SEQUENCE: 46

Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
            20                  25                  30

Ile Glu Arg Gly Thr Ile Gly Gly Thr Cys Val Asn Val Gly Cys Val
        35                  40                  45

Pro Ser Lys Ile Met Ile Arg Ala Ala His Ile Ala His Leu Arg Arg
    50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
        115                 120                 125

Leu Asn Glu Gly Gly Glu Arg Val Val Met Phe Asp Arg Cys Leu Val
    130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
        195                 200                 205

Thr Leu Phe Phe Arg Glu Asp Pro Ala Ile Gly Glu Ala Val Thr Ala
    210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
        275                 280                 285

Gly Ala Ile Val Ile Asp Gln Gly Met Arg Thr Ser Asn Pro Asn Ile
    290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
                325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
        355                 360                 365

Glu Thr Asp Ser Arg Thr Leu Thr Leu Asp Asn Val Pro Arg Ala Leu
    370                 375                 380

Ala Asn Phe Asp Thr Arg Gly Phe Ile Lys Leu Val Ile Glu Glu Gly
385                 390                 395                 400
```

```
Ser His Arg Leu Ile Gly Val Gln Ala Val Cys Pro Glu Ala Gly Glu
              405                 410                 415

Leu Ile Gln Thr Ala Ala Leu Ala Ile Arg Asn Arg Met Thr Val Gln
              420                 425                 430

Glu Leu Ala Asp Gln Leu Phe Pro Tyr Leu Thr Met Val Glu Gly Leu
              435                 440                 445

Lys Leu Ala Ala Gln Thr Phe Asn Lys Asp Val Lys Gln Leu Ser Cys
      450                 455                 460

Cys Ala Gly
465

<210> SEQ ID NO 47
<211> LENGTH: 467
<212> TYPE: PRT
<213> ORGANISM: Artificial Sequence
<220> FEATURE:
<223> OTHER INFORMATION: DM10 A414E

<400> SEQUENCE: 47

Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
              20                  25                  30

Ile Glu Arg Gly Thr Ile Gly Gly Thr Cys Val Asn Val Gly Cys Val
              35                  40                  45

Pro Ser Lys Ile Met Ile Arg Ala Ala His Ile Ala His Leu Arg Arg
      50                  55                  60

Glu Ser Pro Phe Asp Gly Gly Ile Ala Ala Thr Val Pro Thr Ile Asp
65              70                  75                  80

Arg Ser Lys Leu Leu Ala Gln Gln Gln Ala Arg Val Asp Glu Leu Arg
                  85                  90                  95

His Ala Lys Tyr Glu Gly Ile Leu Gly Gly Asn Pro Ala Ile Thr Val
              100                 105                 110

Val His Gly Glu Ala Arg Phe Lys Asp Asp Gln Ser Leu Thr Val Arg
              115                 120                 125

Leu Asn Glu Gly Gly Glu Arg Val Val Met Phe Asp Arg Cys Leu Val
      130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                  165                 170                 175

Glu Arg Leu Ala Val Ile Gly Ser Ser Val Val Ala Leu Glu Leu Ala
              180                 185                 190

Gln Ala Phe Ala Arg Leu Gly Ser Lys Val Thr Val Leu Ala Arg Asn
              195                 200                 205

Thr Leu Phe Phe Arg Glu Asp Pro Ala Ile Gly Glu Ala Val Thr Ala
      210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                  245                 250                 255

Glu Leu Arg Ala Asp Lys Leu Leu Val Ala Thr Gly Arg Thr Pro Asn
              260                 265                 270

Thr Arg Ser Leu Ala Leu Asp Ala Ala Gly Val Thr Val Asn Ala Gln
      275                 280                 285
```

-continued

```
Gly Ala Ile Val Ile Asp Gln Gly Met Arg Thr Ser Asn Pro Asn Ile
    290             295             300

Tyr Ala Ala Gly Asp Cys Thr Asp Gln Pro Gln Phe Val Tyr Val Ala
305             310             315             320

Ala Ala Ala Gly Thr Arg Ala Ala Ile Asn Met Thr Gly Gly Asp Ala
            325             330             335

Ala Leu Asp Leu Thr Ala Met Pro Ala Val Val Phe Thr Asp Pro Gln
            340             345             350

Val Ala Thr Val Gly Tyr Ser Glu Ala Glu Ala His His Asp Gly Ile
            355             360             365

Glu Thr Asp Ser Arg Thr Leu Thr Leu Asp Asn Val Pro Arg Ala Leu
    370             375             380

Ala Asn Phe Asp Thr Arg Gly Phe Ile Lys Leu Val Ile Glu Glu Gly
385             390             395             400

Ser His Arg Leu Ile Gly Val Gln Ala Val Ala Pro Glu Glu Gly Glu
            405             410             415

Leu Ile Gln Thr Ala Ala Leu Ala Ile Arg Asn Arg Met Thr Val Gln
            420             425             430

Glu Leu Ala Asp Gln Leu Phe Pro Tyr Leu Thr Met Val Glu Gly Leu
            435             440             445

Lys Leu Ala Ala Gln Thr Phe Asn Lys Asp Val Lys Gln Leu Ser Cys
    450             455             460

Cys Ala Gly
465
```

```
<210> SEQ ID NO 48
<211> LENGTH: 467
<212> TYPE: PRT
<213> ORGANISM: Artificial Sequence
<220> FEATURE:
<223> OTHER INFORMATION: DM11 G415I

<400> SEQUENCE: 48
```

```
Met Glu Pro Pro Val Gln Val Ala Val Ile Gly Ser Gly Gly Ala Ala
1               5               10              15

Met Ala Ala Ala Leu Lys Ala Val Glu Gln Gly Ala Gln Val Thr Leu
            20              25              30

Ile Glu Arg Gly Thr Ile Gly Gly Thr Cys Val Asn Val Gly Cys Val
        35              40              45

Pro Ser Lys Ile Met Ile Arg Ala Ala His Ile Ala His Leu Arg Arg
    50              55              60

Glu Ser Pro Phe Asp Gly Gly Ile Ala Ala Thr Val Pro Thr Ile Asp
65              70              75              80

Arg Ser Lys Leu Leu Ala Gln Gln Gln Ala Arg Val Asp Glu Leu Arg
            85              90              95

His Ala Lys Tyr Glu Gly Ile Leu Gly Gly Asn Pro Ala Ile Thr Val
            100             105             110

Val His Gly Glu Ala Arg Phe Lys Asp Asp Gln Ser Leu Thr Val Arg
        115             120             125

Leu Asn Glu Gly Gly Glu Arg Val Val Met Phe Asp Arg Cys Leu Val
    130             135             140

Ala Thr Gly Ala Ser Pro Ala Val Pro Pro Ile Pro Gly Leu Lys Glu
145             150             155             160

Ser Pro Tyr Trp Thr Ser Thr Glu Ala Leu Ala Ser Asp Thr Ile Pro
            165             170             175
```

-continued

```
Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
            195                 200                 205

Thr Leu Phe Phe Arg Glu Asp Pro Ala Ile Gly Glu Ala Val Thr Ala
            210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
            275                 280                 285

Gly Ala Ile Val Ile Asp Gln Gly Met Arg Thr Ser Asn Pro Asn Ile
            290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
                325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
            355                 360                 365

Glu Thr Asp Ser Arg Thr Leu Thr Leu Asp Asn Val Pro Arg Ala Leu
            370                 375                 380

Ala Asn Phe Asp Thr Arg Gly Phe Ile Lys Leu Val Ile Glu Glu Gly
385                 390                 395                 400

Ser His Arg Leu Ile Gly Val Gln Ala Val Ala Pro Glu Ala Ile Glu
                405                 410                 415

Leu Ile Gln Thr Ala Ala Leu Ala Ile Arg Asn Arg Met Thr Val Gln
            420                 425                 430

Glu Leu Ala Asp Gln Leu Phe Pro Tyr Leu Thr Met Val Glu Gly Leu
            435                 440                 445

Lys Leu Ala Ala Gln Thr Phe Asn Lys Asp Val Lys Gln Leu Ser Cys
    450                 455                 460

Cys Ala Gly
465
```

```
<210> SEQ ID NO 49
<211> LENGTH: 467
<212> TYPE: PRT
<213> ORGANISM: Artificial Sequence
<220> FEATURE:
<223> OTHER INFORMATION: DM12 E416C

<400> SEQUENCE: 49
```

```
Met Glu Pro Pro Val Gln Val Ala Val Ile Gly Ser Gly Gly Ala Ala
1                   5                   10                  15

Met Ala Ala Ala Leu Lys Ala Val Glu Gln Gly Ala Gln Val Thr Leu
            20                  25                  30

Ile Glu Arg Gly Thr Ile Gly Gly Thr Cys Val Asn Val Gly Cys Val
            35                  40                  45

Pro Ser Lys Ile Met Ile Arg Ala Ala His Ile Ala His Leu Arg Arg
    50                  55                  60
```

-continued

```
Glu Ser Pro Phe Asp Gly Gly Ile Ala Ala Thr Val Pro Thr Ile Asp
65              70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
            115                 120                 125

Leu Asn Glu Gly Gly Glu Arg Val Val Met Phe Asp Arg Cys Leu Val
    130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
            195                 200                 205

Thr Leu Phe Phe Arg Glu Asp Pro Ala Ile Gly Glu Ala Val Thr Ala
    210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
    275                 280                 285

Gly Ala Ile Val Ile Asp Gln Gly Met Arg Thr Ser Asn Pro Asn Ile
    290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
            325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
            355                 360                 365

Glu Thr Asp Ser Arg Thr Leu Thr Leu Asp Asn Val Pro Arg Ala Leu
    370                 375                 380

Ala Asn Phe Asp Thr Arg Gly Phe Ile Lys Leu Val Ile Glu Glu Gly
385                 390                 395                 400

Ser His Arg Leu Ile Gly Val Gln Ala Val Ala Pro Glu Ala Gly Cys
                405                 410                 415

Leu Ile Gln Thr Ala Ala Leu Ala Ile Arg Asn Arg Met Thr Val Gln
            420                 425                 430

Glu Leu Ala Asp Gln Leu Phe Pro Tyr Leu Thr Met Val Glu Gly Leu
            435                 440                 445

Lys Leu Ala Ala Gln Thr Phe Asn Lys Asp Val Lys Gln Leu Ser Cys
    450                 455                 460

Cys Ala Gly
465
```

-continued

<210> SEQ ID NO 50
<211> LENGTH: 467
<212> TYPE: PRT
<213> ORGANISM: Artificial Sequence
<220> FEATURE:
<223> OTHER INFORMATION: DM13 L417I

<400> SEQUENCE: 50

Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
            20                  25                  30

Ile Glu Arg Gly Thr Ile Gly Gly Thr Cys Val Asn Val Gly Cys Val
        35                  40                  45

Pro Ser Lys Ile Met Ile Arg Ala Ala His Ile Ala His Leu Arg Arg
    50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
            115                 120                 125

Leu Asn Glu Gly Gly Glu Arg Val Val Met Phe Asp Arg Cys Leu Val
        130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
        195                 200                 205

Thr Leu Phe Phe Arg Glu Asp Pro Ala Ile Gly Glu Ala Val Thr Ala
        210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
            245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
            275                 280                 285

Gly Ala Ile Val Ile Asp Gln Gly Met Arg Thr Ser Asn Pro Asn Ile
        290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
            325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
        355                 360                 365

-continued

```
Glu Thr Asp Ser Arg Thr Leu Thr Leu Asp Asn Val Pro Arg Ala Leu
    370             375             380

Ala Asn Phe Asp Thr Arg Gly Phe Ile Lys Leu Val Ile Glu Glu Gly
385             390             395             400

Ser His Arg Leu Ile Gly Val Gln Ala Val Ala Pro Glu Ala Gly Glu
            405             410             415

Ile Ile Gln Thr Ala Ala Leu Ala Ile Arg Asn Arg Met Thr Val Gln
            420             425             430

Glu Leu Ala Asp Gln Leu Phe Pro Tyr Leu Thr Met Val Glu Gly Leu
            435             440             445

Lys Leu Ala Ala Gln Thr Phe Asn Lys Asp Val Lys Gln Leu Ser Cys
    450             455             460

Cys Ala Gly
465
```

```
<210> SEQ ID NO 51
<211> LENGTH: 467
<212> TYPE: PRT
<213> ORGANISM: Artificial Sequence
<220> FEATURE:
<223> OTHER INFORMATION: DM14 I418D

<400> SEQUENCE: 51

Met Glu Pro Pro Val Gln Val Ala Val Ile Gly Ser Gly Gly Ala Ala
1               5               10              15

Met Ala Ala Ala Leu Lys Ala Val Glu Gln Gly Ala Gln Val Thr Leu
            20              25              30

Ile Glu Arg Gly Thr Ile Gly Gly Thr Cys Val Asn Val Gly Cys Val
            35              40              45

Pro Ser Lys Ile Met Ile Arg Ala Ala His Ile Ala His Leu Arg Arg
    50              55              60

Glu Ser Pro Phe Asp Gly Gly Ile Ala Ala Thr Val Pro Thr Ile Asp
65              70              75              80

Arg Ser Lys Leu Leu Ala Gln Gln Gln Ala Arg Val Asp Glu Leu Arg
            85              90              95

His Ala Lys Tyr Glu Gly Ile Leu Gly Gly Asn Pro Ala Ile Thr Val
            100             105             110

Val His Gly Glu Ala Arg Phe Lys Asp Asp Gln Ser Leu Thr Val Arg
            115             120             125

Leu Asn Glu Gly Gly Glu Arg Val Val Met Phe Asp Arg Cys Leu Val
            130             135             140

Ala Thr Gly Ala Ser Pro Ala Val Pro Pro Ile Pro Gly Leu Lys Glu
145             150             155             160

Ser Pro Tyr Trp Thr Ser Thr Glu Ala Leu Ala Ser Asp Thr Ile Pro
            165             170             175

Glu Arg Leu Ala Val Ile Gly Ser Ser Val Val Ala Leu Glu Leu Ala
            180             185             190

Gln Ala Phe Ala Arg Leu Gly Ser Lys Val Thr Val Leu Ala Arg Asn
            195             200             205

Thr Leu Phe Phe Arg Glu Asp Pro Ala Ile Gly Glu Ala Val Thr Ala
    210             215             220

Ala Phe Arg Ala Glu Gly Ile Glu Val Leu Glu His Thr Gln Ala Ser
225             230             235             240

Gln Val Ala His Met Asp Gly Glu Phe Val Leu Thr Thr Thr His Gly
            245             250             255
```

```
Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
            275                 280                 285

Gly Ala Ile Val Ile Asp Gln Gly Met Arg Thr Ser Asn Pro Asn Ile
    290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
                325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
            355                 360                 365

Glu Thr Asp Ser Arg Thr Leu Thr Leu Asp Asn Val Pro Arg Ala Leu
    370                 375                 380

Ala Asn Phe Asp Thr Arg Gly Phe Ile Lys Leu Val Ile Glu Glu Gly
385                 390                 395                 400

Ser His Arg Leu Ile Gly Val Gln Ala Val Ala Pro Glu Ala Gly Glu
                405                 410                 415

Leu Asp Gln Thr Ala Ala Leu Ala Ile Arg Asn Arg Met Thr Val Gln
            420                 425                 430

Glu Leu Ala Asp Gln Leu Phe Pro Tyr Leu Thr Met Val Glu Gly Leu
            435                 440                 445

Lys Leu Ala Ala Gln Thr Phe Asn Lys Asp Val Lys Gln Leu Ser Cys
    450                 455                 460

Cys Ala Gly
465

<210> SEQ ID NO 52
<211> LENGTH: 467
<212> TYPE: PRT
<213> ORGANISM: Artificial Sequence
<220> FEATURE:
<223> OTHER INFORMATION: DM15 A422N

<400> SEQUENCE: 52

Met Glu Pro Pro Val Gln Val Ala Val Ile Gly Ser Gly Gly Ala Ala
1               5                   10                  15

Met Ala Ala Ala Leu Lys Ala Val Glu Gln Gly Ala Gln Val Thr Leu
            20                  25                  30

Ile Glu Arg Gly Thr Ile Gly Gly Thr Cys Val Asn Val Gly Cys Val
            35                  40                  45

Pro Ser Lys Ile Met Ile Arg Ala Ala His Ile Ala His Leu Arg Arg
    50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
            115                 120                 125

Leu Asn Glu Gly Gly Glu Arg Val Val Met Phe Asp Arg Cys Leu Val
    130                 135                 140
```

-continued

```
Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
            195                 200                 205

Thr Leu Phe Phe Arg Glu Asp Pro Ala Ile Gly Glu Ala Val Thr Ala
        210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
            275                 280                 285

Gly Ala Ile Val Ile Asp Gln Gly Met Arg Thr Ser Asn Pro Asn Ile
        290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
                325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
            355                 360                 365

Glu Thr Asp Ser Arg Thr Leu Thr Leu Asp Asn Val Pro Arg Ala Leu
        370                 375                 380

Ala Asn Phe Asp Thr Arg Gly Phe Ile Lys Leu Val Ile Glu Glu Gly
385                 390                 395                 400

Ser His Arg Leu Ile Gly Val Gln Ala Val Ala Pro Glu Ala Gly Glu
                405                 410                 415

Leu Ile Gln Thr Ala Asn Leu Ala Ile Arg Asn Arg Met Thr Val Gln
            420                 425                 430

Glu Leu Ala Asp Gln Leu Phe Pro Tyr Leu Thr Met Val Glu Gly Leu
            435                 440                 445

Lys Leu Ala Ala Gln Thr Phe Asn Lys Asp Val Lys Gln Leu Ser Cys
    450                 455                 460

Cys Ala Gly
465

<210> SEQ ID NO 53
<211> LENGTH: 467
<212> TYPE: PRT
<213> ORGANISM: Artificial Sequence
<220> FEATURE:
<223> OTHER INFORMATION: DM16 L448T

<400> SEQUENCE: 53

Met Glu Pro Pro Val Gln Val Ala Val Ile Gly Ser Gly Gly Ala Ala
1                   5                   10                  15

Met Ala Ala Ala Leu Lys Ala Val Glu Gln Gly Ala Gln Val Thr Leu
                20                  25                  30
```

-continued

```
Ile Glu Arg Gly Thr Ile Gly Gly Thr Cys Val Asn Val Gly Cys Val
        35                  40                  45

Pro Ser Lys Ile Met Ile Arg Ala Ala His Ile Ala His Leu Arg Arg
    50                  55                  60

Glu Ser Pro Phe Asp Gly Gly Ile Ala Ala Thr Val Pro Thr Ile Asp
65                  70                  75                  80

Arg Ser Lys Leu Leu Ala Gln Gln Gln Ala Arg Val Asp Glu Leu Arg
                85                  90                  95

His Ala Lys Tyr Glu Gly Ile Leu Gly Gly Asn Pro Ala Ile Thr Val
            100                 105                 110

Val His Gly Glu Ala Arg Phe Lys Asp Asp Gln Ser Leu Thr Val Arg
            115                 120                 125

Leu Asn Glu Gly Gly Glu Arg Val Val Met Phe Asp Arg Cys Leu Val
    130                 135                 140

Ala Thr Gly Ala Ser Pro Ala Val Pro Pro Ile Pro Gly Leu Lys Glu
145                 150                 155                 160

Ser Pro Tyr Trp Thr Ser Thr Glu Ala Leu Ala Ser Asp Thr Ile Pro
                165                 170                 175

Glu Arg Leu Ala Val Ile Gly Ser Ser Val Val Ala Leu Glu Leu Ala
            180                 185                 190

Gln Ala Phe Ala Arg Leu Gly Ser Lys Val Thr Val Leu Ala Arg Asn
            195                 200                 205

Thr Leu Phe Phe Arg Glu Asp Pro Ala Ile Gly Glu Ala Val Thr Ala
    210                 215                 220

Ala Phe Arg Ala Glu Gly Ile Glu Val Leu Glu His Thr Gln Ala Ser
225                 230                 235                 240

Gln Val Ala His Met Asp Gly Glu Phe Val Leu Thr Thr Thr His Gly
                245                 250                 255

Glu Leu Arg Ala Asp Lys Leu Leu Val Ala Thr Gly Arg Thr Pro Asn
            260                 265                 270

Thr Arg Ser Leu Ala Leu Asp Ala Ala Gly Val Thr Val Asn Ala Gln
            275                 280                 285

Gly Ala Ile Val Ile Asp Gln Gly Met Arg Thr Ser Asn Pro Asn Ile
    290                 295                 300

Tyr Ala Ala Gly Asp Cys Thr Asp Gln Pro Gln Phe Val Tyr Val Ala
305                 310                 315                 320

Ala Ala Ala Gly Thr Arg Ala Ala Ile Asn Met Thr Gly Gly Asp Ala
            325                 330                 335

Ala Leu Asp Leu Thr Ala Met Pro Ala Val Val Phe Thr Asp Pro Gln
            340                 345                 350

Val Ala Thr Val Gly Tyr Ser Glu Ala Glu Ala His His Asp Gly Ile
            355                 360                 365

Glu Thr Asp Ser Arg Thr Leu Thr Leu Asp Asn Val Pro Arg Ala Leu
    370                 375                 380

Ala Asn Phe Asp Thr Arg Gly Phe Ile Lys Leu Val Ile Glu Glu Gly
385                 390                 395                 400

Ser His Arg Leu Ile Gly Val Gln Ala Val Ala Pro Glu Ala Gly Glu
                405                 410                 415

Leu Ile Gln Thr Ala Ala Leu Ala Ile Arg Asn Arg Met Thr Val Gln
            420                 425                 430
```

-continued

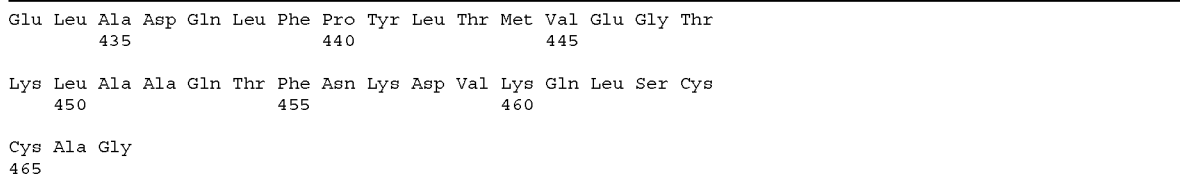

```
Glu Leu Ala Asp Gln Leu Phe Pro Tyr Leu Thr Met Val Glu Gly Thr
        435                 440                 445

Lys Leu Ala Ala Gln Thr Phe Asn Lys Asp Val Lys Gln Leu Ser Cys
        450                 455                 460

Cys Ala Gly
465
```

1

USING SYNTHETIC LIXIVIANT BIOLOGY FOR THE RECOVERY OF PRECIOUS AND TOXIC METALS FROM ANTHROPOGENIC SOURCES

CROSS-REFERENCES TO RELATED APPLICATIONS

This application is a U.S. National Phase Application of PCT International Application No. PCT/SG2020/050216, filed Apr. 8, 2020, which is an International Application of and claims the benefit of priority to SG Patent Application No. 10201903117U, filed on Apr. 8, 2019 and SG Patent Application No. 10201904705X, filed on May 25, 2019 the entire contents of which are herein incorporated by reference.

FIELD OF THE INVENTION

The present invention relates to a method of using enzymes to break down cyanide, and a method of synthetic metal recovery for synthetic lixiviant biology. More particularly, the invention relates to the use of engineered bacteria to be used in processes involving cyanogenesis, reduction of leached metal ions, cyanolysis and downstream recycling of cyanide. Further provided are tools for transcription control in *C. violaceum.*

BACKGROUND OF THE INVENTION

Cyanide readily combines with most major and trace metals to form cyanide complexes, a property which makes it useful in extracting metals from ores. Sodium cyanide is most commonly used in mining sites which readily dissolves in water, yielding sodium ion and cyanide ion, $CN^-$. Some $CN^-$ will convert into hydrogen cyanide, HCN and their relative amounts are determined by the water pH. At pH above 9.0, $CN^-$ is the predominant stable form. As pH drops, there will be increasing amount of $CN^-$ converting to HCN which readily forms a gas and release into the air. Hence, most mining solutions are maintained at pH above 10.0 which prevents formation of HCN gas and accidental poisoning of mine workers via inhalation. As cyanide is carbon based, it reacts readily with other carbon-based matter, making it toxic to many living organisms. Hence, cyanide-containing waste must be detoxified before disposal. Conventional methods include alkaline chlorination which is both hazardous and costly. Furthermore, problems arise when the cyanide used in mining does not break down quickly into harmless substances. Even these less toxic substances can persist in the environment for a significant period of time which can pose problems to the aquatic ecosystem.

The electronic waste recycling industry uses chemical processes which pose considerable environmental risks: current processes for recovering precious metals such as gold, and removal of toxic metals such as lead and mercury, include pyrometallurgy (open burning, etc.) and hydrometallurgy (acid leaching and industrial cyanidation or cyanide baths); these methods are energy intensive, require additional electrolysis steps for metal separation, and are extremely pollutive in nature (Korte, F., Spiteller, M. & Coulston, F. (2000) *Ecotoxicology and Environmental Safety* 46, 241-245; Fields, S. (2001) *Environ Health Perspect* 109, A474-481). There have been research efforts in using biotechnological leaching processes to replace the industrial chemical processes so that the metal recovery and remediation is simpler, more cost efficient and environmentally benign, and scientists and engineers such as Brandl (Brandl, H., Lehmann, S., Faramarzi, M. A., and Martinelli, D. (2008), *Hydrometallurgy* 94, 14-17), Watling (Watling, H. R. (2006), *Hydrometallurgy* 84, 81-108) and Rawlings (Rawlings, D. E. (2002), *Annual Review of Microbiology* 56, 65-91) have contributed significantly to the field of biotechnological leaching. Compared to conventional techniques for precious metal recovery via acid solubilisation, current efforts in bioremediating electronic waste to recover precious metals such as gold involve the use of lixiviant-producing microbes (Korte, F., Spiteller, M. & Coulston, F. (2000) *Ecotoxicology and Environmental Safety* 46, 241-245; Pham, V., and Ting, Y. P. (2009), *Advanced Materials Research* 71, 661-664; Liang, G., Mo, Y., and Zhou, Q. (2010), *Enzyme and Microbial Technology* 47, 322-326; Chi, T. D., Lee, J. C., Pandey, B. D., Yoo, K., and Jeong, J. (2011), *Miner Eng* 24, 1219-1222). In such microbes, the lixiviant involved in bioremediation and recovery of metals is usually hydrogen cyanide. Although possible hydrogen cyanide leakage poses a considerable threat to the environment, the use of microbes in the biomining industry limits and minimizes such concerns as the microbes in context are both cyanogenic (capable of generating cyanide equivalents) and cyanolytic (capable of detoxifying cyanide equivalents), virtually ensuring that there will be no bulk release of cyanide into the environment during the bioleaching process.

In contrast to existing processes, bioleaching by naturally-occurring microorganisms, working under mild operating conditions, may allow metal recycling in a process analogous to natural biogeochemical cycles, and hence reduces the demand for resources such as ores, energy or landfill space (Brandl, H., Lehmann, S., Faramarzi, M. A., and Martinelli, D. (2008), *Hydrometallurgy* 94, 14-17). Bioleaching is of interest since it represents "clean technology". As a leaching agent, hydrogen cyanide is formed by a variety of bacteria (e.g. *Chromobacterium violaceum, Pseudomonas fluorescens*, and *P. aeruginosa*) and fungi (e.g. *Marasmius oreades, Clitocybe* sp., *Polysporus* sp.) (Pham, V., and Ting, Y. P. (2009), *Advanced Materials Research* 71, 661-664). Cyanide is formed as a secondary metabolite and for a short duration within the lifetime of the microbe. Although cyanide production by microorganisms is known for many years, quantitative data on cyanide production for many species are lacking (Liang, G., Mo, Y., and Zhou, Q. (2010), *Enzyme and Microbial Technology* 47, 322-326). However, current biorecovery and bioremediation efforts are unable to match industrial expectations of cost efficiency (Faramarzi, M. A., et al., (2004), *Journal of Biotechnology* 113, 321-326; Krebs, W., et al., (1997), *FEMS Microbiology Reviews* 20, 605-617) (efficient metal recovery, short time of bioleaching, and non-reliance on conventional electrolysis for metal separation) of leaching, resulting in the continued use of conventional hydrometallurgical and pyrometallurgical methods for metal remediation. This disparity in expectations is a result of the inherent sub-optimal lixiviant metabolism of microbes, and the absence of a suitable biological reduction route for specific metal recovery after bioleaching.

There is a pressing need to develop sustainable technologies to recycle electronic waste in order to protect our environment and preserve natural resources. The invention focuses on the recovery of precious metals and the removal of toxic metals from electronic waste. Current conventional treatment technologies for electronic waste using strong acids or cyanide are pollutive in nature.

SUMMARY OF THE INVENTION

The present invention generally relates to methods of biological reduction of metal-cyanide complexes after metal-cyanidation and methods of biologically hydrolysing cyanide.

The present invention allows the engineering of an integrated synthetic lixiviant biological system to be housed within a synthetic host (such as the cyanogenic *Chromobacterium violaceum*) for efficient precious metal recovery and toxic metal remediation of electronic waste. There may be up to four main components/modules in the design and engineering of the synthetic host: 1) synthetic cyanogenesis; 2) synthetic metal recovery; 3) synthetic cyanolysis; and 4) synthetic circuits for lixiviant biology. This invention enables synthetic circuits for lixiviant biology to be constructed.

In this invention, the inventors have designed and constructed tools to remove excess cyanide from the environment, providing industry with sustainable gold cyanidation processes. In addition, the inventors have designed and constructed genome editing tools for *Chromobacterium violaceum* for the construction of synthetic *C. violaceum* to recover precious and toxic metals from electronic waste. Further, the inventors have designed and constructed tools to reduce ionic gold ($Au^{3+}$) and/or silver ($Ag^+$) back to the elemental state (Au) and (Ag) as gold and silver nanoparticles, respectively, providing industry with an alternative to conventional recovery steps involving electrolysis.

According to a first aspect, the present invention provides an isolated genetically engineered bacterium, wherein the bacterium has been transformed by at least one polynucleotide molecule; the at least one polynucleotide molecule comprising a heterologous mercury(II) reductase (MerA) gene, operably linked to at least one promoter, and comprising at least one mutation which renders the gene product capable of reducing ionic metal to elemental metal as metal nanoparticles.

Another aspect provides an isolated genetically engineered bacterium, wherein the bacterium has been transformed by at least one polynucleotide molecule; the at least one polynucleotide molecule comprising a heterologous hydrogen cyanide synthase gene and a heterologous 3-phosphoglycerate dehydrogenase mutant gene operably linked to at least one promoter.

In some embodiments the isolated genetically engineered bacterium further comprises at least one polynucleotide molecule comprising, in order from N-terminus to C-terminus of the recombinant DNA molecule;
- (i) a go/S transcriptional activator gene operably linked to a constitutive promoter, and a ph1F repressor gene operably linked to a $P_{goITS}$ or $P_{goIB}$ promoter;
- (ii) a promoter activated by CviR and an operator of PhIF, and
- (iii) one or more of said heterologous hydrogen cyanide synthase gene and said heterologous 3-phosphoglycerate dehydrogenase mutant gene operably linked to the CviR-activated promoter.

Another aspect provides A process for recovering elemental gold or silver, as gold nanoparticles from ionic gold (Au3+) or as silver nanoparticles from ionic silver (Ag+), respectively, said process comprising the steps of:
- a) contacting the isolated genetically engineered bacterium according to any one of claims 1 to 4 with a leachate comprising ionic gold (Au3+) and/or ionic silver (Ag+); and

- b) recovering the elemental gold and/or silver nanoparticles from the leachate.

According to another preferred embodiment, the present invention provides a method for producing an isolated genetically engineered bacterium, wherein the bacterium has been transformed by at least one polynucleotide molecule; the at least one polynucleotide molecule comprising a heterologous mercury(II) reductase (MerA) gene, operably linked to at least one promoter, and comprising one or more mutations which renders the gene product capable of reducing ionic gold ($Au^{3+}$) to elemental gold as gold nanoparticles, or ionic silver (Ag+) which is reduced to elemental silver as silver nanoparticles, said method comprising the steps:
- a) performing error-prone PCR on a gene encoding mercury(II) reductase (MerA);
  - i) transforming at least one bacterium with the products of said PCR;
  - ii) selecting transformants that grow on a media comprising $Au^{3+}$ and/or Ag+; or
- b) performing multiple site-saturated mutagenesis by overlap-extension PCR on a gene encoding mercury(II) reductase (MerA);
  - i) transforming at least one bacterium with the products of said PCR;
  - ii) selecting transformants that grow on a media comprising $Au^{3+}$ and/or $Ag^+$.

It would be understood that other forms of gold could be used on the growth media, such as AuCl.

Another aspect provides an isolated genetically engineered bacterium, wherein the bacterium has been transformed by at least one polynucleotide molecule; the at least one polynucleotide molecule comprising a heterologous nitrilase gene, the product of which causes cyanolysis of hydrogen cyanide, operably linked to at least one promoter.

In some embodiments the at least one polynucleotide molecule further comprises a heterologous formate dehydrogenase gene, a heterologous glutamate dehydrogenase gene and a heterologous phosphoenolpyruvate carboxylase gene operably linked to at least one promoter.

Another aspect provides a process of synthetic cyanide lixiviant production, said process comprising; contacting at least one recombinant cyanogenic bacterium with glycine, wherein the at least one bacterium is engineered to express a heterologous hydrogen cyanide synthase (hcnABC) gene and a heterologous 3-phosphoglycerate dehydrogenase mutant (serA) gene by linkage to at least one promoter. An example is shown in FIG. 2A.

In some embodiments the recombinant cyanogenic bacterium further comprises at least one polynucleotide molecule comprising, in order from N-terminus to C-terminus of the recombinant DNA molecule;
- (i) a go/S transcriptional activator gene operably linked to a constitutive promoter, and a ph1F repressor gene operably linked to a $P_{goITS}$ or $P_{goIB}$ promoter;
- (ii) a promoter activated by CviR and an operator of PhIF, and
- (iii) one or more of said heterologous hydrogen cyanide synthase gene and said heterologous 3-phosphoglycerate dehydrogenase mutant gene operably linked to the CviR-activated promoter.

According to another aspect, the present invention provides at least one isolated recombinant bacterium, capable of synthetic cyanide lixiviant production, as herein defined.

According to another aspect, the present invention provides a process of synthetic cyanolysis, said process comprising; contacting at least one recombinant cyanolytic bacterium with nitriles including cyanide present after bioleaching of electronic waste, wherein the at least one bacterium is engineered to express at least one nitrilase enzyme.

In some embodiments the at least one recombinant cyanolytic bacterium is further engineered to express formate dehydrogenase, glutamate dehydrogenase and phosphoenolpyruvate carboxylase.

According to another aspect, the present invention provides an isolated recombinant DNA molecule comprising, in order from N-terminus to C-terminus of the recombinant DNA molecule;

(i) a go/S transcriptional activator gene operably linked to a constitutive promoter, and a ph1F repressor gene operably linked to a $P_{golTS}$ or $P_{golB}$ promoter;

(ii) a promoter activated by CviR and an operator of PhIF, and (iii) one or more cyanogenic genes operably linked to the CviR-activated promoter.

According to another aspect, the present invention provides use of a deactivated Cas9 comprising mutations H840A and D10A in the HNH endonuclease domain and the RuvC endonuclease domain, respectively, and an sgRNA to inhibit transcription of one or more genes in the *Chromobacterium violaceum* genome by targeting the promoter region of said one or more genes.

In some embodiments the one or more genes encode violacein purple pigment formation.

Another aspect provides an isolated recombinant DNA molecule comprising a golTSB operon, wherein the operon comprises in order from N-terminus to C-terminus of the recombinant DNA molecule; golT operably linked to j23119 promoter, golS, golB operably linked to golB promoter, and a reporter gene, such as GFP. This operon can be used for general screening for MerA gold-reducing engineered bacteria.

BRIEF DESCRIPTION OF THE FIGURES

FIG. 1A; Shows an engineered cyanogenic strain (SynLix 3.1) produces up to 80 mg/L of cyanide. SynLix 3.1 was engineered to express hydrogen cyanide synthase (hcnABC) and a mutant of 3-phosphoglycerate dehydrogenase (serA). FIG. 1B; An overview of the cyanolysis and coupling process. An engineered cyanogenic strain (SynLix 3.1) is tolerant at pH 10.0 (alkaliphilic).

FIG. 5 shows repression of violacein production in *C. violaceum* in dCas9. (A) Schematic of dCas9 circuitry. (B) The targeted region of the violacein operon are indicated by the three dCas9-sgRNA complex, the vioA promoter, vioB promoter and 5' region of vioC. (C) gRNA targeting the vioA promoter requires the lowest amount of dCas9 induction (0.01% arabinose), gRNA targeting vioB promoter requires slightly higher amount of dCas9 induction (0.1% arabinose), while gRNA targeting vioC, further down the transcription start site, has the same effect as both non-targeting gRNA negative controls. (D) Measured OD600 of the corresponding wells in (C).

FIG. 15 shows a schematic of reversible synchronized ON-OFF circuitry in response to absence and presence of gold ions. Circuitry is turned ON by the quorum sensor (middle box) and turned OFF by the gold ion sensor (left box). The reversible circuitry can be turned ON again in the absence of gold ions with dilution of the repressor. Gold ion sensor (left box) consists of the GolS transcriptional activator that is activated by gold ions for the expression of PhlF repressor. The quorum sensor (middle box) makes use of the endogenous CviR activator of the host that is induced by AHL under high cell density. Cyanogenesis output (right box) represented by RFP is thus synchronized at high cell density and inhibited in the presence of gold ions.

Figure 1A:
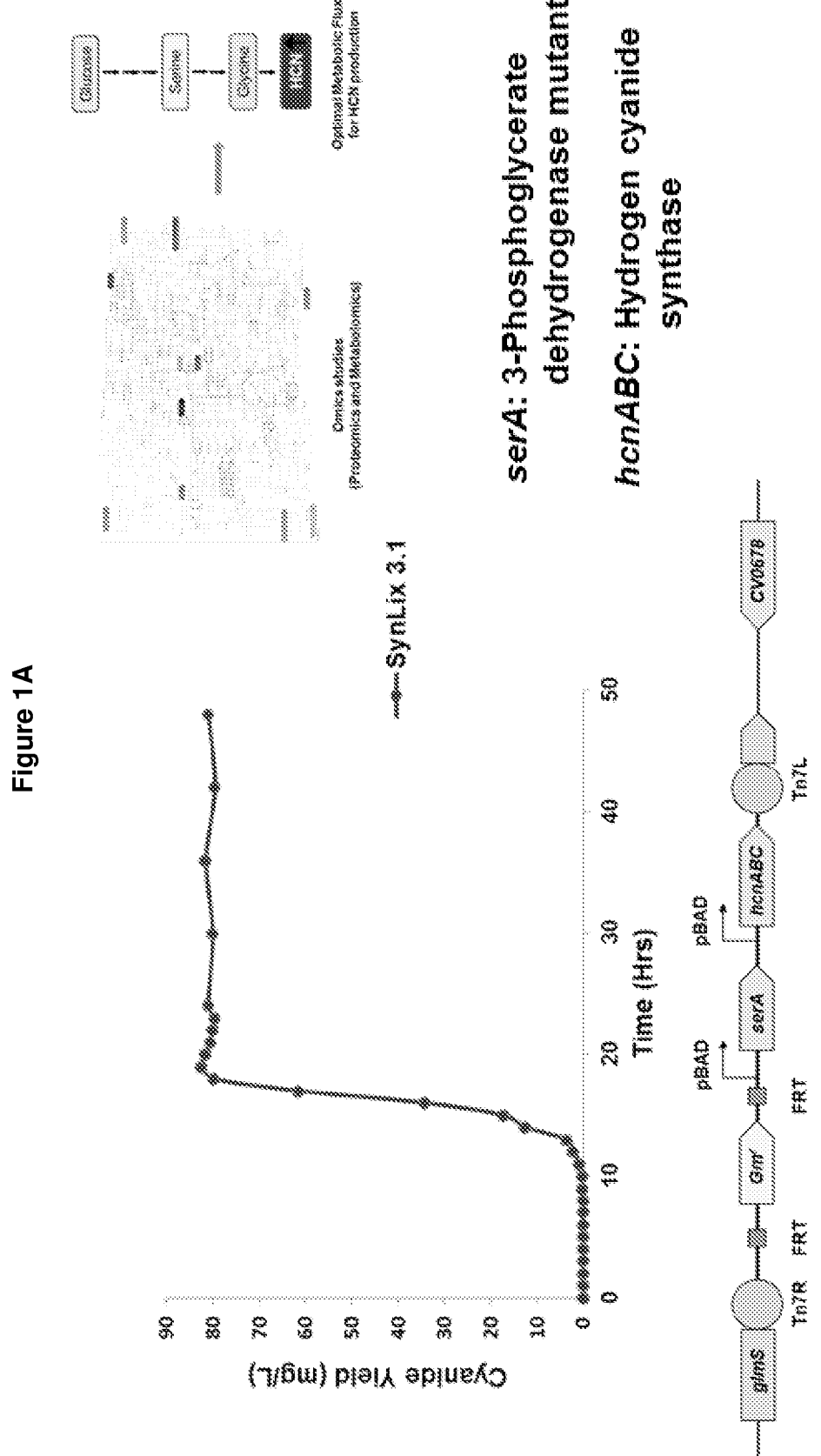
FIGS. 1A-1B.
Figure 1B:
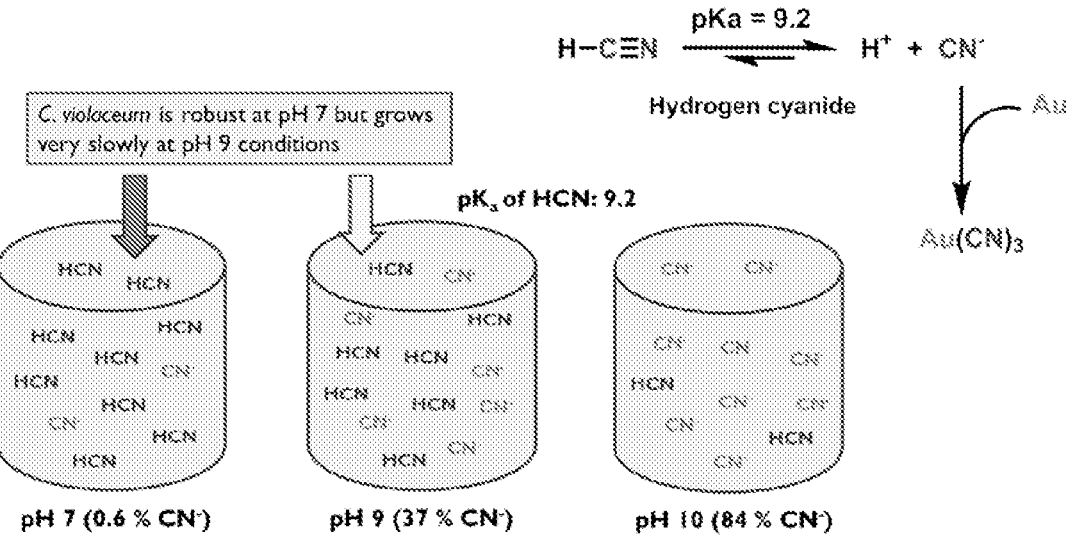

Bibliographic references mentioned in the present specification are for convenience listed in the form of a list of references and added at the end of the examples. The whole content of such bibliographic references is herein incorporated by reference but their mention in the specification does not imply that they form part of the common general knowledge.

DETAILED DESCRIPTION OF THE INVENTION

It is envisioned that the use of engineered bacteria in processes involving cyanogenesis, reduction of leached metal ions, cyanolysis and downstream recycling of cyanide will require the use of separate strains of bacteria, harbouring separate mutant enzymes. Some strains will selectively reduce gold, whilst others will selectively reduce silver. A possible workflow would include: Strains that generate the biolixiviant to oxidise metals; strains will then reduce metals selectively, using gold- and silver-reducing mutants, to recover the metals; and strains will be used to bioremediate the biolixiviant by biodegrading cyanide.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

Certain terms employed in the specification, examples and appended claims are collected here for convenience.

The terms "a" and "an" are used herein to refer to one or to more than one (i.e. at least one) of the grammatical object of the article.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

Ranges can be expressed herein as from "about" one particular value, and/or to "about" another particular value. When such a range is expressed, another embodiment includes-, from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In a first aspect of the invention there is provided an isolated genetically engineered bacterium, wherein the bacterium has been transformed by at least one polynucleotide molecule; the at least one polynucleotide molecule comprising a heterologous mercury(II) reductase (MerA) gene, operably linked to at least one promoter, and comprising one or more mutations which renders the gene product capable of reducing ionic metal to elemental metal as metal nanoparticles.

In some embodiments the MerA gene comprises one or more mutations which encode amino acid substitutions, wherein the amino acid substitutions are at positions selected from the group comprising V317, Y441 and C464. In other embodiments the MerA gene mutation is at one or more sites selected from the group comprising A323D, A323D (delΔ324-365), A414E, G415I, E416C, L417I, I418D and A422N.

In some embodiments said ionic metal is ionic gold (Au$^{3+}$) which is reduced to elemental gold as gold nanoparticles, or ionic silver (Ag$^+$) which is reduced to elemental silver as silver nanoparticles.

In some embodiments said isolated bacterium has reduced reductive capacity for mercury substrate when compared to a bacterium comprising a non-mutated MerA gene.

In some embodiments an isolated genetically engineered bacterium has been transformed by at least one polynucleotide molecule; the at least one polynucleotide molecule comprising a heterologous hydrogen cyanide synthase gene and a heterologous 3-phosphoglycerate dehydrogenase mutant gene operably linked to at least one promoter. In some embodiments the hydrogen cyanide synthase gene is hcnABC (SEQ ID NO: 35) and/or the 3-phosphoglycerate dehydrogenase mutant gene is serA (SEQ ID NO: 36). These genes are present to increase hydrogen cyanide production to leach precious metals from sources such as electronic waste.

In some embodiments the production of hydrogen cyanide is under the control of an on/off switch, comprising a gold ion sensor and a quorum sensor (for example shown in FIG. 15). More particularly, the gold sensor switches off the leaching process once leached gold reaches a critical level. The off circuit responds to gold ions produced by cyanidation and comprises a 'low' constitutive promoter driving a go/S gene and a promoter driving a repressor gene which is downstream. An example of a minimal gold sensor comprises a go/S transcriptional activator gene under the control of a low constitutive promoter (e.g. P$_{Con6}$; SEQ ID NO: 37) and a ph1F repressor gene driven by a P$_{golTS}$ or P$_{golB}$ promoter to produce Ph1F repressor to block an operator of PhIF in the quorum sensor. The ON circuit of the qorum sensor responds to high cell density and comprises a promoter, which is activated by endogenous CviR (induced by AHL at high cell density), and an operator of PhIF downstream of the quorum sensor promoter.

Downstream and under the regulation of the quorum sensor is a cyanogenesis gene or genes, selected from a heterologous hydrogen cyanide synthase gene and a heterologous 3-phosphoglycerate dehydrogenase mutant gene as described above.

In some embodiments, the isolated genetically engineered bacterium comprises a heterologous hydrogen cyanide synthase gene and a heterologous 3-phosphoglycerate dehydrogenase mutant gene operably linked to an on/off circuit, wherein the off circuit is upstream of the on circuit which is upstream of the hydrogen cyanide synthase gene and 3-phosphoglycerate dehydrogenase mutant gene, wherein the off circuit comprises a heterologous go/S gene, operably linked to a promoter, and a downstream heterologous ph1F repressor gene operably linked to a promoter selected from $P_{golTS}$ and $P_{golB}$, wherein the on circuit comprises a promoter, which is activated by endogenous CviR, and an operator of PhlF between the CviR-activated promoter and wherein said hydrogen cyanide synthase gene and 3-phosphoglycerate dehydrogenase mutant genes are operably linked to said CviR-activated promoter.

Figure 12:
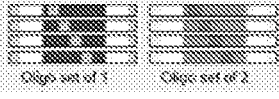
FIG. 12 shows an experimental workflow for mutagenesis and selection of gold sensor mutants in *C. violaceum*. Templates of mutant libraries of go/S transcriptional activator were created by deep scanning mutagenesis where each amino acid is replaced by 19 other amino acids. Mutant libraries were subsequently cloned and transformed into *C. violaceum*. Mutants with higher fluorescence output and sensitivity to gold ions were chosen.
Figure 12:
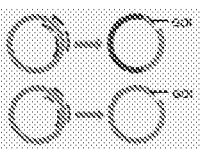
Figure 12:
Figure 12:
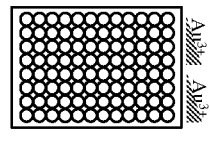
Figure 12:
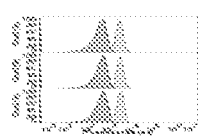

Preferably the go/S gene is codon optimized for *C. violaceum* and the dynamic range and sensitivity is optimized by mutagenesis (for example shown in FIG. 12). In some embodiments the go/S gene is a mutant selected from GolSmt1_A38I, GolSmt2_A38Q&N97D, GolSmt3_A38K&V60L and GolSmt4_D33P.

Figure 19:
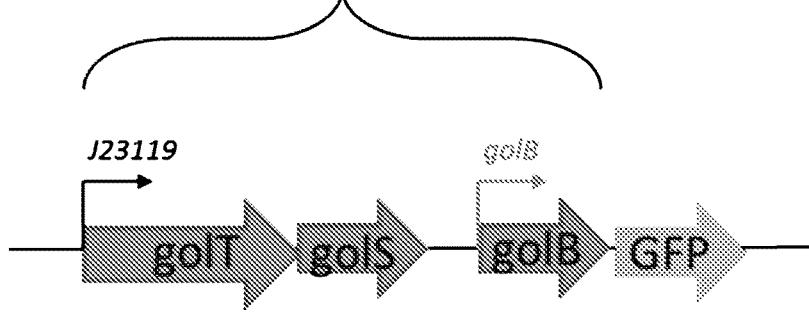
FIG. 19 shows schematic of construction of biosensor. The *Salmonella* gol operon is comprised of golT, golS and golB, coding for P-type ATPase, Au sensor and metal binding chaperone respectively. Constitutive *E. coli* promoter J23119 ensures expression of Au sensor for binding of $Au^{3+}$ ions which then binds Au-sensing promoter golB and drives expression of GFP.

A useful gold ion sensor comprises a golTSB operon, shown in FIG. 19.

Another aspect provides an isolated recombinant DNA molecule comprising a golTSB operon, wherein the operon comprises in order from N-terminus to C-terminus of the recombinant DNA molecule; golT operably linked to j23119 promoter, golS, golB operably linked to golB promoter, and a reporter gene, such as GFP. This operon can be used for general screening for MerA gold-reducing engineered bacteria.

Nitrilases are a group of enzymes which hydrolyze nitriles to ammonia and corresponding carboxylic acid. There are two types of such cyanide-degrading enzymes.

$$R\!-\!C\!\equiv\!N \;+\; 2H_2O \;\rightleftharpoons\; R\!-\!C{\overset{\displaystyle O}{\underset{\displaystyle OH}{}}} \;+\; NH_3$$

$$R\!-\!C\!\equiv\!N \;+\; H_2O \;\rightleftharpoons\; R\!-\!C{\overset{\displaystyle O}{\underset{\displaystyle NH_2}{}}}$$

The first, cyanide dihydratases, comprise a group of bacterial enzymes. These enzymes behave as true nitrilases, converting cyanide directly to formate and ammonia (upper scheme). On the other hand, cyanide hydratases which are of fungal origin hydrolyze cyanide to formamide (lower scheme). These hydrolytic enzymes do not require additional cofactors or substrates and catalyze over a wide substrate concentration, making them good candidates for bioremediation of cyanide.

In some embodiments an isolated genetically engineered bacterium may comprise a heterologous nitrilase gene operably linked to at least one promoter. The nitrilase gene causes cyanolysis of hydrogen cyanide. In some embodiments the heterologous nitrilase gene encodes an enzyme selected from the group comprising cyanide dehydratase and cyanide hydratase. In some embodiments the at least one nitrilase enzyme is derived from at least one bacterial species selected from the group comprising *Pseudomonas pseudoalcaligenes* (nit), *Synechocystis* sp. PCC 6803 chromosome (SC-nit), cyanide dihydratase from *Bacillus pumilus* (BP-cynD) and *Pseudomonas stutzeri* (PS-cynD). Apart from being part of an integrated workflow, the cyanolytic strains for bioremediation may be used by themselves, or as containment for cyanide-heavy industries.

Figure 3:
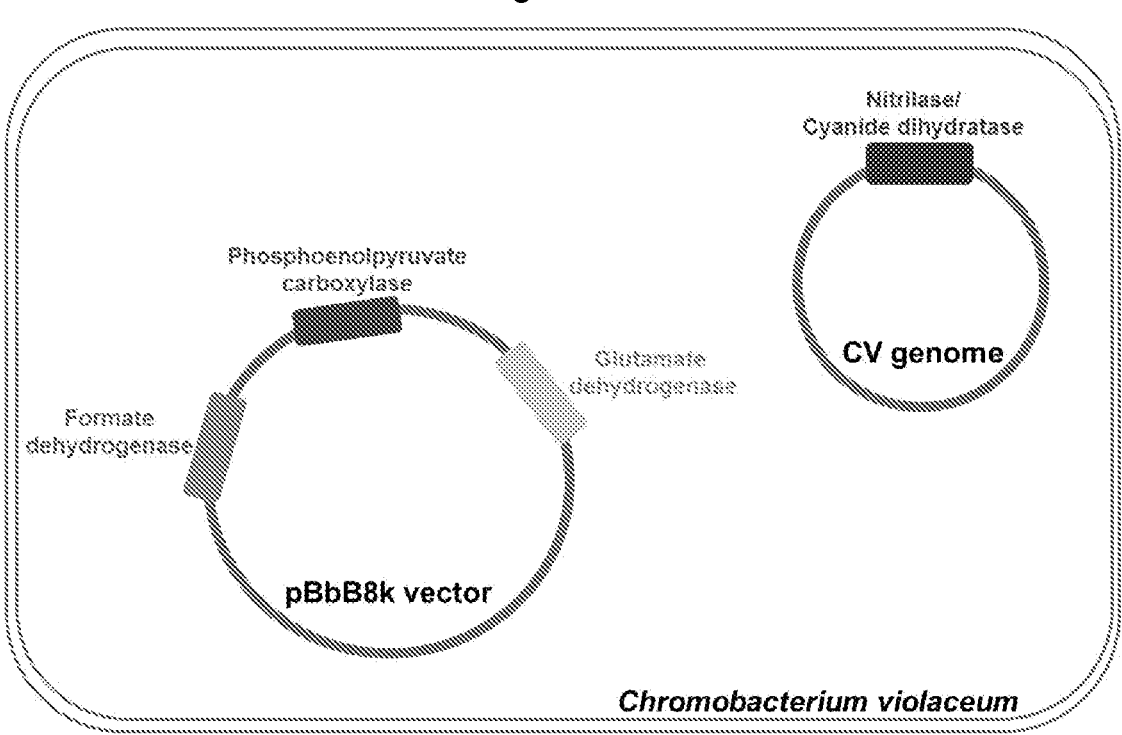
FIG. 3 shows a schematic of a recombinant *Chromobacterium violaceum* host cell. Coupling enzymes include formate dehydrogenase, glutamate dehydrogenase and phosphoenolpyruvate carboxylase. These enzymes were cloned in pBbB8k-RFP (Broad Host range) vector and subsequently expressed in *Chromobacterium violaceum*. By coupling cyanolysis process to downstream enzymes, the by-products, carbon and nitrogen, can be recycled, making it a self-sustaining system

In some embodiments the isolated genetically engineered bacterium further comprises a heterologous formate dehydrogenase gene, a heterologous glutamate dehydrogenase gene and a heterologous phosphoenolpyruvate carboxylase gene operably linked to at least one promoter. By coupling the cyanolysis process to downstream enzymes, formate dehydrogenase, glutamate dehydrogenase and phosphoenolpyruvate carboxylase, the by-products, carbon and nitrogen, can be recycled, making it a self-sustaining system (FIG. 3).

In some embodiments the isolated genetically engineered bacterium comprises a heterologous nitrilase gene, a heterologous formate dehydrogenase gene, a heterologous glutamate dehydrogenase gene and a heterologous phosphoenolpyruvate carboxylase gene operably linked to at least one promoter.

In some embodiments the bacterium is selected from the group comprising *Chromobacterium violaceum, Pseudomonas fluorescens, P. aeruginosa* and *Escherichia coli.*

In some embodiments the bacterium is stable at pH 10.

A second aspect of the invention provides a process for recovering elemental gold or silver, as gold nanoparticles from ionic gold ($Au^{3+}$) or as silver nanoparticles from ionic silver ($Ag^+$), respectively, said process comprising the steps of:

a) contacting the isolated genetically engineered bacterium according to any aspect of the invention with a leachate comprising ionic gold ($Au^{3+}$) and/or ionic silver ($Ag^+$); and b) recovering the elemental gold and/or silver nanoparticles from the leachate.

In some embodiments the said contact is performed in alkaline conditions.

In some embodiments the contacting is performed at a pH of at least about 10.

A third aspect of the invention provides a method for producing an isolated bacterium comprising at least one polynucleotide molecule; the at least one polynucleotide molecule comprising a heterologous mercury(II) reductase (MerA) gene, operably linked to at least one promoter, and comprising one or more mutations which renders the gene product capable of reducing ionic metal to elemental metal as metal nanoparticles, said method comprising the steps:

a) performing error-prone PCR on a gene encoding mercury(II) reductase (MerA);

i) transforming at least one bacterium with the products of said PCR;

ii) selecting transformants that grow on a media comprising ionic metal; or b) performing multiple site-saturated mutagenesis by overlap-extension PCR on a gene encoding mercury(II) reductase (MerA);

i) transforming at least one bacterium with the products of said PCR;

ii) selecting transformants that grow on a media comprising ionic metal.

In some embodiments the gene product is capable of reducing ionic gold ($Au^{3+}$) and/or ionic silver ($Ag^+$) to elemental gold as gold nanoparticles and/or to elemental silver as silver nanoparticles, respectively, In some embodiments in part ii) the ionic metal is selected from $AuCl_3$ and/or $AgNO_3$. In some embodiments in part a) the PCR is performed with forward and reverse primers, wherein the forward primer comprises the nucleotide sequence 5'-GTGGTGGTGGTGGTGCTCGAGTTA-3' (SEQ ID NO: 1) and the reverse primer comprises the nucleotide sequence 5'-GATATACATATGCACCACCATCACCATCAT-3' (SEQ ID NO: 2).

In some embodiments in part b) the PCR is performed with primers containing NNK and/or MNN at the target sites are V317, Y441 and C464 of the MerA protein.

In some embodiments said selection involves at least 2 forms of selection, wherein one form comprises selection on agar plates comprising $Au^{3+}$ and/or $Ag^+$ and another form comprises selection in liquid culture comprising $Au^{3+}$ and/or $Ag^+$.

A fourth aspect of the invention provides a process of synthetic cyanide lixiviant production, said process comprising:

contacting a recombinant cyanogenic bacterium with glycine, wherein the bacterium comprises a heterologous hydrogen cyanide synthase gene and a heterologous 3-phosphoglycerate dehydrogenase mutant gene operably linked to at least one promoter.

In some embodiments the hydrogen cyanide synthase gene is hcnABC and/or the 3-phosphoglycerate dehydrogenase mutant gene is serA. An example is shown in FIG. 1A, where a mutant called SynLix 3.1 was grown in LB, and cyanide production was monitored over 48 hours. Cyanide production was detected using a cyanide sensitive ion selective electrode (ISE).

In some embodiments the hcnABC and serA genes are under the control of inducible promoters. In some embodiments the isolated genetically engineered bacterium comprises a heterologous hydrogen cyanide synthase gene and a heterologous 3-phosphoglycerate dehydrogenase mutant gene operably linked to an on/off circuit, wherein the off circuit is upstream of the on circuit which is upstream of the hydrogen cyanide synthase gene and 3-phosphoglycerate dehydrogenase mutant gene, wherein the off circuit comprises a heterologous go/S gene, operably linked to a promoter, and a downstream heterologous ph1F repressor gene operably linked to a promoter selected from $P_{golTS}$ and $P_{golB}$, wherein the on circuit comprises a promoter, which is activated by endogenous CviR, and an operator of PhIF between the CviR-activated promoter and wherein said hydrogen cyanide synthase gene and 3-phosphoglycerate dehydrogenase mutant genes are operably linked to said CviR-activated promoter.

In some embodiments the recombinant cyanogenic bacterium is tolerant to a pH of at least about 10.

In some embodiments the synthetic cyanide lixiviant production is performed in a single reactor together with metal for bioleaching.

Another aspect of the invention provides at least one isolated recombinant bacterium, capable of synthetic cyanide lixiviant production, as defined in any aspect of the invention.

In some embodiments the recombinant cyanogenic bacterium is selected from the group comprising *Chromobacterium violaceum, Pseudomonas fluorescens, P. aeruginosa* and *Escherichia coli.*

Another aspect of the invention provides a process of synthetic cyanolysis, said process comprising:

a) contacting at least one recombinant cyanolytic bacterium with nitriles including cyanide present after bioleaching of electronic waste, wherein the at least one bacterium is engineered to express at least one nitrilase enzyme.

In some embodiments the at least one nitrilase enzyme is selected from the group comprising cyanide dehydratase and cyanide hydratase.

In some embodiments the at least one recombinant cyanolytic bacterium is further engineered to express formate dehydrogenase, glutamate dehydrogenase and phosphoenolpyruvate carboxylase.

In some embodiments the at least one nitrilase enzyme is derived from at least one bacterial species selected from the group comprising *Pseudomonas pseudoalcaligenes* (nit),

*Synechocystis* sp. PCC 6803 chromosome (SC-nit), cyanide dihydratase from *Bacillus pumilus* (BP-cynD) and *Pseudomonas stutzeri* (PS-cynD).

Another aspect of the invention provides an isolated recombinant DNA molecule comprising, in order from N-terminus to C-terminus of the recombinant DNA molecule;

(i) a go/S transcriptional activator gene operably linked to a constitutive promoter, and a ph1F repressor gene operably linked to a $P_{golTS}$ or $P_{golB}$ promoter;

(ii) a promoter activated by CviR and an operator of PhIF, and (iii) one or more cyanogenic genes operably linked to the CviR-activated promoter.

In some embodiments the go/S transcriptional activator gene is under the control of a low constitutive promoter, such as $P_{Con6}$.

In some embodiments the go/S gene is codon optimized for *C. violaceum* and the dynamic range and sensitivity is optimized by mutagenesis (for example shown in FIG. 12). In some embodiments the go/S gene is a mutant selected from the group comprising or consisting of GolSmt1_A38I, GolSmt2_A38Q&N97D, GolSmt3_A38K&V60L and GolSmt4_D33P.

Another aspect of the invention provides use of a deactivated Cas9 comprising mutations H840A and D10A in the HNH endonuclease domain and the RuvC endonuclease domain, respectively, and an sgRNA to inhibit transcription of one or more genes in the *Chromobacterium violaceum* genome by targeting the promoter region of said one or more genes.

In some embodiments a deactivated Cas9-encoding gene is operably linked to a $P_{araBAD}$ promoter and the RNA guide (sgRNA)-encoding gene is operably linked to a strong constitutive promoter such as J23119.

In some embodiments the deactivated Cas9 targets the violacein operon to prevent violacein purple pigment formation, because the pigment can complicate downstream processing steps. In some embodiments the deactivated Cas9 targets the vioA, vioB and/or vioC promoter, preferably all three promoters. Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Green and Sambrook, Molecular Cloning: A Laboratory Manual, Cold Springs Harbor Laboratory, New York (2012).

Example 1

Integrating Nitrilases into Host Cells for Cyanolysis

Four variants of nitrilases from different bacteria were selected; their sequences were synthesized and subsequently cloned into their respective host cells. Nitrilase from *Pseudomonas pseudoalcaligenes* (nit) (SEQ ID NO: 11) and *Synechocystis* sp. PCC 6803 chromosome (SC-nit) (SEQ ID NO: 12), cyanide dihydratase from *Bacillus pumilus* (BP-cynD) (SEQ ID NO: 13) and *Pseudomonas stutzeri* (PS-cynD) (SEQ ID NO: 14). Nit contained 2 different subunits, namely nitB (SEQ ID NO: 15) and nitC (SEQ ID NO: 16), were cloned into pRSF-Duet vector and expressed in *E. coli*

Figure 2:
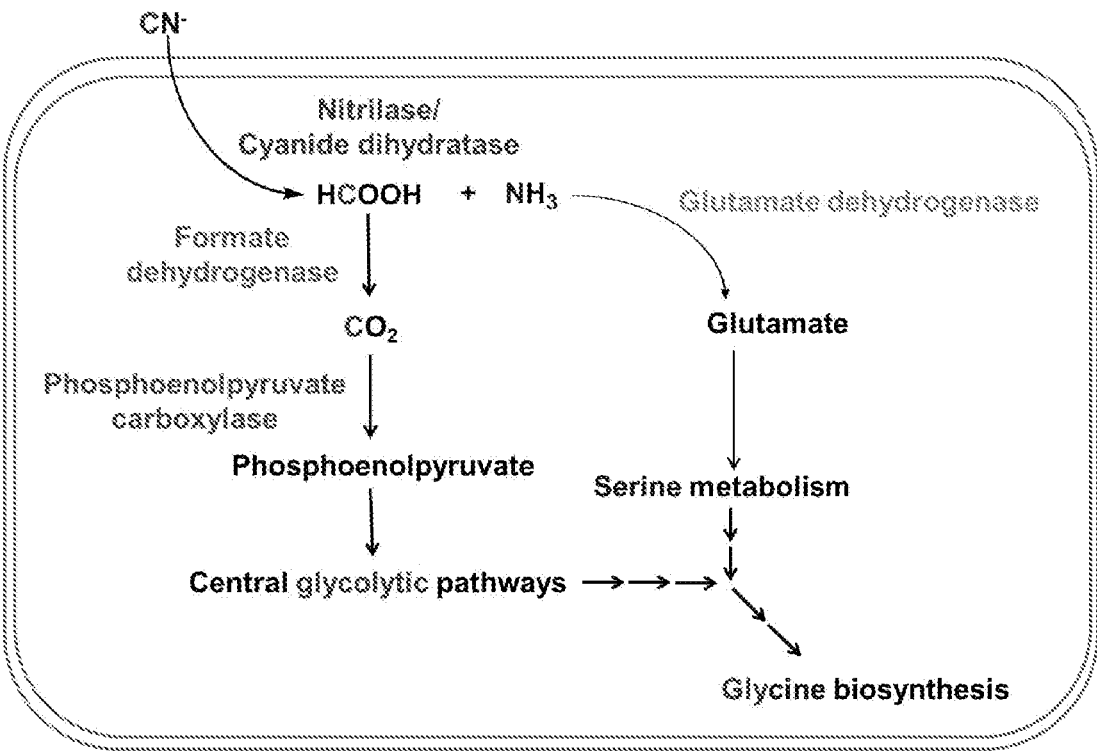
FIG. 2 shows an overview of the cyanolysis and coupling process. Four variants of nitrilases from different bacteria were selected; their sequences were synthesized and subsequently cloned into their respective host cells. Nitrilase from *Pseudomonas pseudoalcaligenes* (nit) and *Synechocystis* sp. PCC 6803 chromosome (SC-nit), cyanide dihydratase from *Bacillus pumilus* (BP-cynD) and *Pseudomonas stutzeri* (PS-cynD). Nit contained 2 different subunit, namely nitB and nitC, were cloned into pRSF-Duet vector and expressed in *E. coli* (DE3) BL21 host cell. For the remaining three variants, they were cloned into pGM vector and subsequently integrated into *Chromobacterium violaceum* genome via Tn7 transposition system

(DE3) BL21 host cell. For the remaining three variants, they were cloned into pGEM vector and subsequently integrated into *Chromobacterium violaceum* genome via Tn7 transposition system (FIGS. 2 and 3).

Coupling enzymes include formate dehydrogenase, glutamate dehydrogenase and phosphoenolpyruvate carboxylase. These enzymes were cloned in pBbB8k-RFP (Broad Host range) vector and subsequently expressed in *Chromobacterium violaceum*. By coupling cyanolysis process to downstream enzymes, the by-products, carbon and nitrogen, can be recycled, making it a self-sustaining system (FIG. 3).

Cyanolytic strains of *Chromobacterium violaceum* were tested for their ability to remove cyanide from the extracellular environment. In the presence of 100 mg/L of potassium cyanide, the engineered cyanolytic *C. violaceum* strains were able to completely remove the exogenous cyanide within 24 hours.

Example 2

Development of Genomic Transcriptional Control Tool with dCas9 in *Chromobacterium violaceum*.

CRISPR-Cas9 is widely adopted as a genome editing tool in many organisms. It has been used in mainly eukaryotes including mammalian, insect and yeast cells. The CRISPR-Cas system originates from the bacterial adaptive immune system where it inserts small fragments of invaded bacteriophages DNA into its host genome as memory for surveillance of possible future invasions of bacteriophages consisting of the same DNA fragments. CRISPR-Cas9 system from *Streptomyces pyogenes* consists of a Cas9 endonuclease that together with an RNA guide, binds to DNA sequence homologous to the RNA guide and brings Cas9 endonuclease to cleave the double stranded DNA of invading bacteriophages. When used as a genome editing tool, the Cas9 endonuclease is expressed with a RNA guide consisting of a 20 nucleotide spacer complementary to target DNA followed by a 76 bp scaffold that contacts the Cas9 endonuclease. Upon guided to the target DNA by the 20 bp spacer of the RNA guide, Cas9 endonuclease causes double stranded breaks in the host chromosome. The host activates DNA repair mechanisms to the cleaved chromosome, resulting in insertions, deletions or homologous recombination of introduced DNA fragments into the DNA target site. With the ease and modularity of the RNA guided mechanism, the CRISPR-Cas9 genome editing method quickly became adopted in many organisms.

Figure 4:
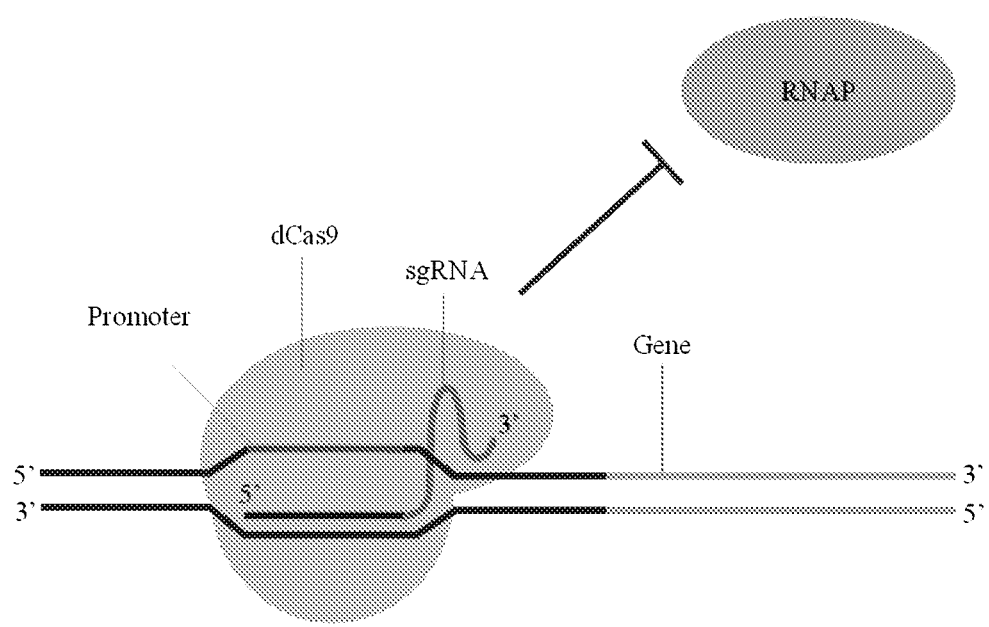
FIG. 4 shows a schematic representation of a deactivated Cas9 mechanism of transcriptional repression. The catalytically inactivated Cas9 is guided by sgRNA (blue) to the promoter sequence and physically inhibits RNAP from initiating transcription. The targeted 20 nucleotide protospacer (purple) in the promoter region is immediately adjacent to the protospacer adjacent motif (PAM) sequence NGG (red) which is required for Cas9 binding to DNA.

CRISPR-Cas has been adapted for many other applications. Due to the ease and specificity of DNA sequence recognition by RNA, many applications and variations of Cas9 have been applied for targeting of specific genomic locus. CRISPRi (CRISPR-interference) and CRISPRa (CRISPR-activation) that target gene transcription are two additions to the CRISPR/Cas genetic tools. CRISPRi (FIG. 4) is mediated by a deactivated Cas9 (dCas) (SEQ ID NO: 17), which has mutations H840A and D10A in the HNH endonuclease domain and the RuvC endonuclease domain respectively, that inhibits the transcription of the gene via steric hindrance of RNA polymerase binding to the promoter region. CRISPRa is achieved via a fusion protein between the dCas and an activator that recruits the RNA polymerase, enhancing the transcription of the gene. Although CRISPRa has been shown to increase expression of target genes by 3-fold [Bikard, D. et al., *Nucleic Acids Res*, 41(15), 7429-7437 (2013)], CRISPRi has been applied more widely in genus belonging to *Escherichia, Pseudomonas, Mycobacterium, Corynebacterium, Clostridium* and *Bacillus*, inhibiting gene expression up to 300-fold [Cho, S. et al., *Int J Mol Sci*, 19(4). doi:10.3390/ijms19041089 (2018); Qi et al., 2013). CRISPRi tool will be explored in *C. violaceum* for transcriptional inhibition of chromosomal gene expression.

The CRISPR/Cas genome editing tool has been a powerful tool for eukaryotic cells, however, the use of CRISPR/Cas is more limited in prokaryotes due to the lethality of double stranded DNA cuts in prokaryotes. The DNA repair mechanism in prokaryotes is not sufficient to rescue the cells, resulting in lethality of bacteria when CRISPR/Cas is employed.

Figure 5:
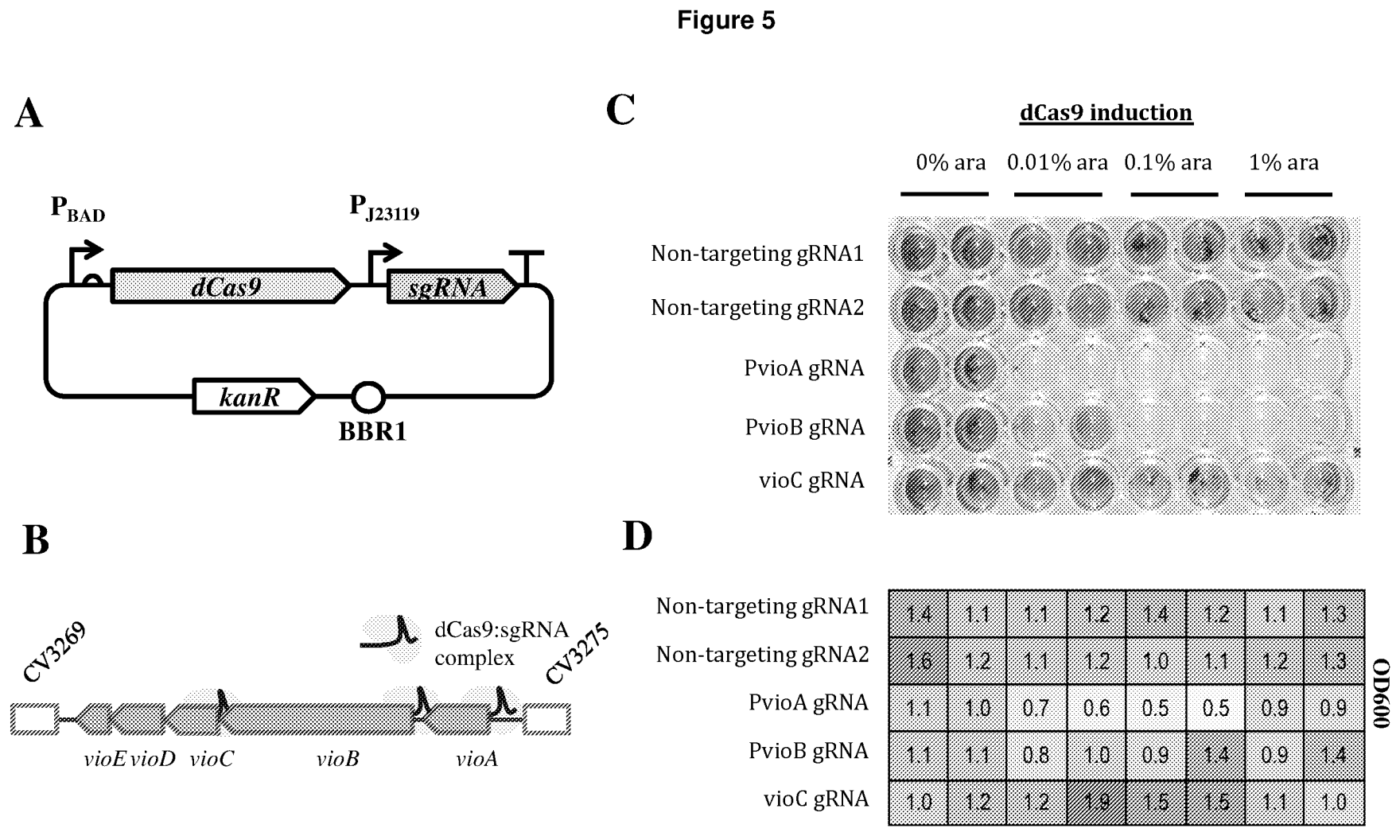

However, the use of the deactivated Cas9 (dCas9), with D10A mutation and H840A mutation in the catalytic domain, has been adapted to block transcription of target genes (FIG. 5). In this study, dCas9 is used to target the promoter region of the violacein operon, preventing the formation of the violacein purple pigment (FIG. 5B). The repression is the most effective when the first gene (vioA) promoter (SEQ ID NO: 18) is targeted, requiring only 0.01% of arabinose. This is followed by vioB promoter (SEQ ID NO: 19), which requires a higher amount of 0.1% arabinose induction of dCas9 expression for violacein repression. Inhibition at further downstream of the operon, vioC (SEQ ID NO: 20), exerts almost no effect on violacein transcription repression. The slight drop in OD should not be due to metabolic burden of expression of dCas. One of the main reasons could be due to overlap of the absorbance spectra of violacein, with its maximum absorbance at $OD_{570}$ [Swem, L. R. et al., *Mol Cell*, 35(2), 143-153 (2009)]. Another reason in the slight drop of optical density could be due to the clumping of cells when violacein pigment is not fully repressed (FIG. 5C).

Chromosomal transcriptional control of *C. violaceum* has not been reported to date. The control of endogenous genes will be useful for metabolic engineering, especially in the control of metabolic flux, providing fast and efficient knockdown of gene expression. As multiplexing is straightforward, many genes can be knocked down at once efficiently and quickly [Cobb, R. E. et al., *ACS Synth Biol*, 4(6), 723-728 (2014); Cress et al., 2015). Furthermore, dCas9 can be fused to other proteins including cytidine deaminases or adenine deaminases for single nucleotide mutations [Arazoe, T. et al., *Biotechnology journal*, 13(9): e1700596 (2018); Komor, Kim, Packer, Zuris, & Liu, 2016), providing tremendous opportunity for the expansion of the *C. violaceum* genetic toolbox.

Cloning and Expression of dCas for *Chromobacterium violaceum*

The two catalytic mutations D10A and H840A were introduced in Cas9 via mutational primers and Gibson assembly. dCas was subsequently cloned under the control of the $P_{araBAD}$ (SEQ ID NO: 21). A strong constitutive promoter, J23119 (SEQ ID NO: 22), was used to drive expression of sgRNA targeting vioA promoter, vioB promoter, 5' end of vioC and two non-targeting sequences (FIG. 5A). Overnight cultures of *C. violaceum* were diluted 1:100 into 96-deep well block (Nunc, Denmark) and dCas was induced by adding 0.01% arabinose, 0.1% arabinose, or 1 arabinose or no induction as control. Cultures were grown at 37° C., 280 rpm overnight before the cultures were transferred to 96-deep well plate for visualization of violacein production and OD600 measurement.

Example 3

Construction of a Gold Sensor in *Chromobacterium violaceum* from a Natural Gold Operon An important sensor for a gold bioleaching circuitry is the gold sensor. The amount of gold leached will be able to provide dynamic feedback to the circuitry and stop the leaching process whenever the gold ions concentration reaches a critical level. The only gold biosensor demonstrated so far is the golTSB operon (SEQ ID NO: 23) from *Salmonella enterica* serovar *Typhimurium* str. LT2. It contains GolS (SEQ ID NO: 24), shown to be the only MerR family transcriptional regulator reported to be able to distinguish gold ion from copper and silver ions [Cerminati, S. et al., *Biotechnol Bioeng*, 108(11), 2553-2560 (2011)]. While this gold biosensor has only been demonstrated in *E. coli* and *S. enterica* previously, it is optimized in *C. violaceum* for the first time in this report to achieve a large dynamic range.

Figure 6:
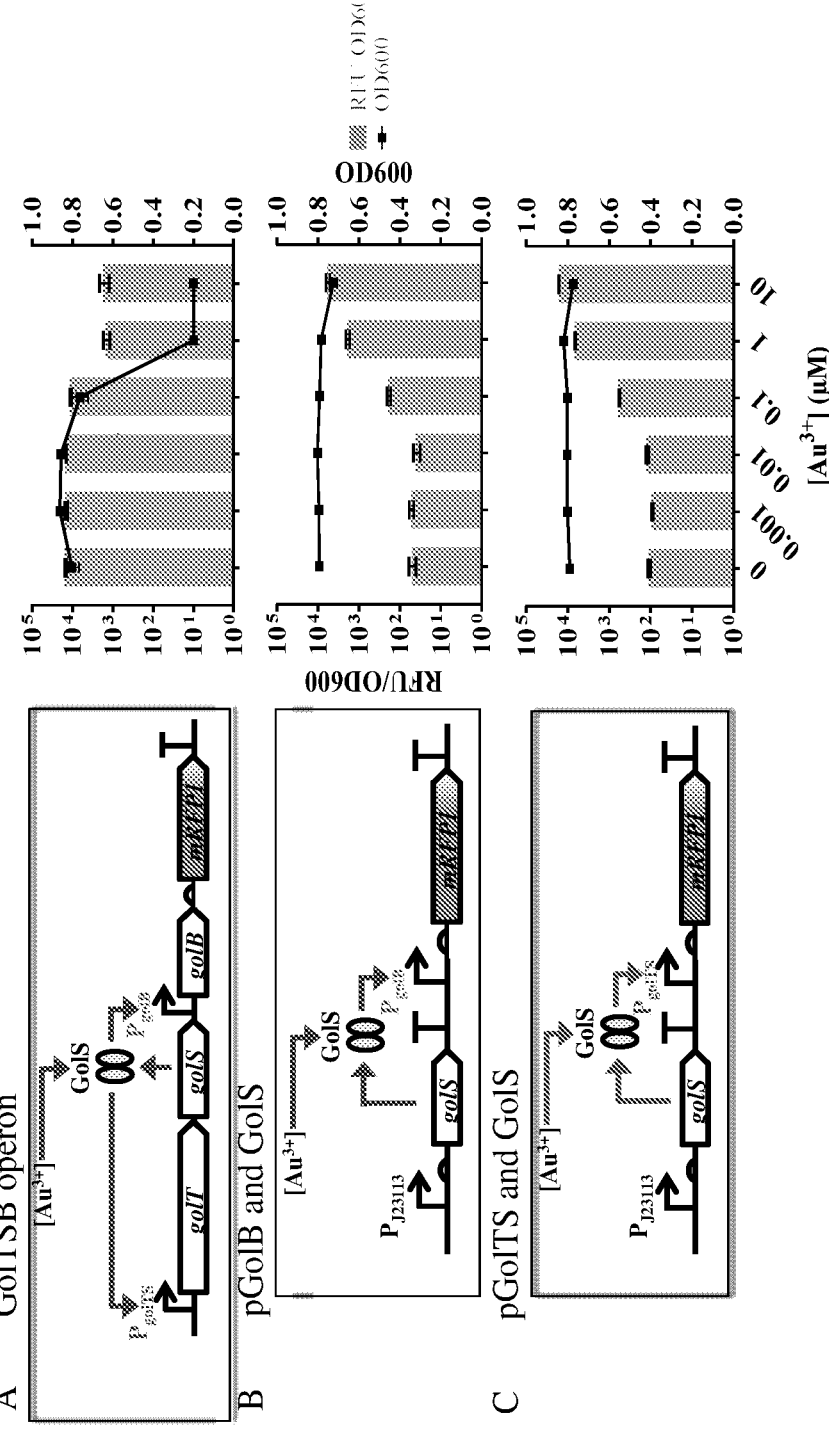
FIG. 6 shows gold sensor circuitry optimization. Gold ions dose response and circuitry schematic with (A) original GolTSB operon or minimal gold sensor consisting of GolS transcriptional activator and (B) $P_{golTS}$ or (C) $P_{golB}$.

The entire golTSB operon is first cloned upstream of the fluorescent protein output for the characterization of the gold sensor. However, the fluorescence output has a low dynamic range of output across the concentrations of $Au^{3+}$ from 0.001 µM to 10 µM (FIG. 6A). This low dynamic range is due to the high leaky expression of 14842 RFU in the absence of $Au^{3+}$ (FIG. 6A). In addition, there is a huge drop in cell

Figure 7:
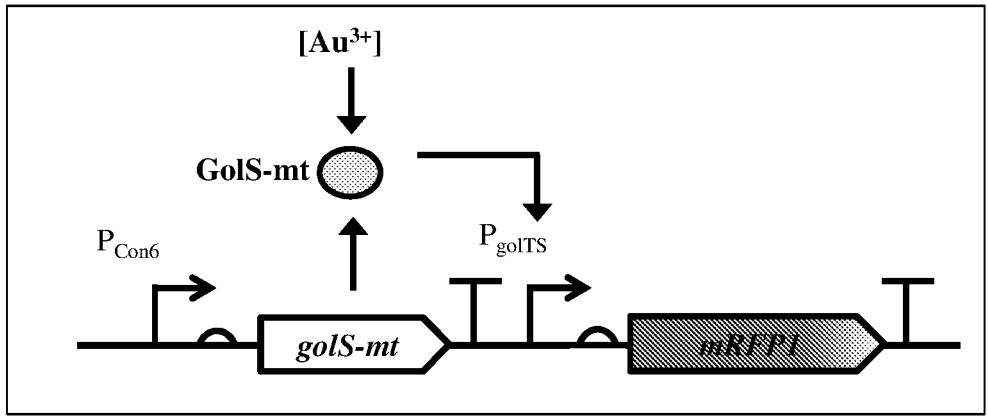
FIG. 7 shows a circuitry schematic of the gold mutant sensor.
Figure 8:
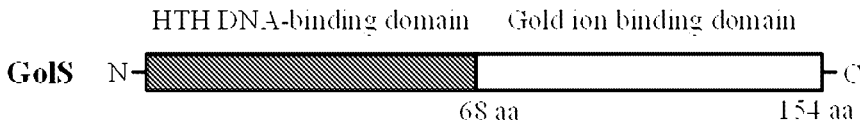
FIG. 8 shows the structure of GolS. (A) N-terminal and C-terminal domain of GolS consists of a helix-turn-helix (HTH) DNA-binding domain and a gold ion binding domain, respectively. (B) Predicted structure of GolS homodimer bound to DNA using Phyre2 (Kelley, Mezulis, Yates, Wass, & Sternberg, 2015). The residue (right arrows) at the DNA binding domain is mutated in GolSmt1, GolSmt2 and GolSmt3. GolSmt2 has an additional mutation (residue on top, up arrow) at gold ion binding domain. GolSmt3 has an additional mutation (left arrow residue) at the DNA binding domain.
Figure 8:
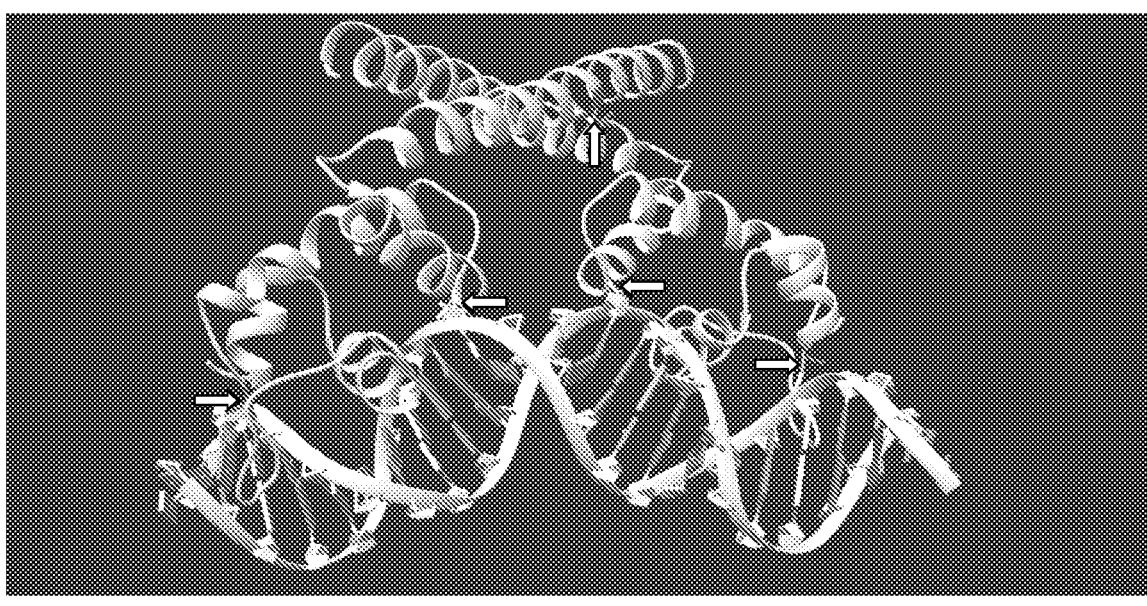
Figure 9:
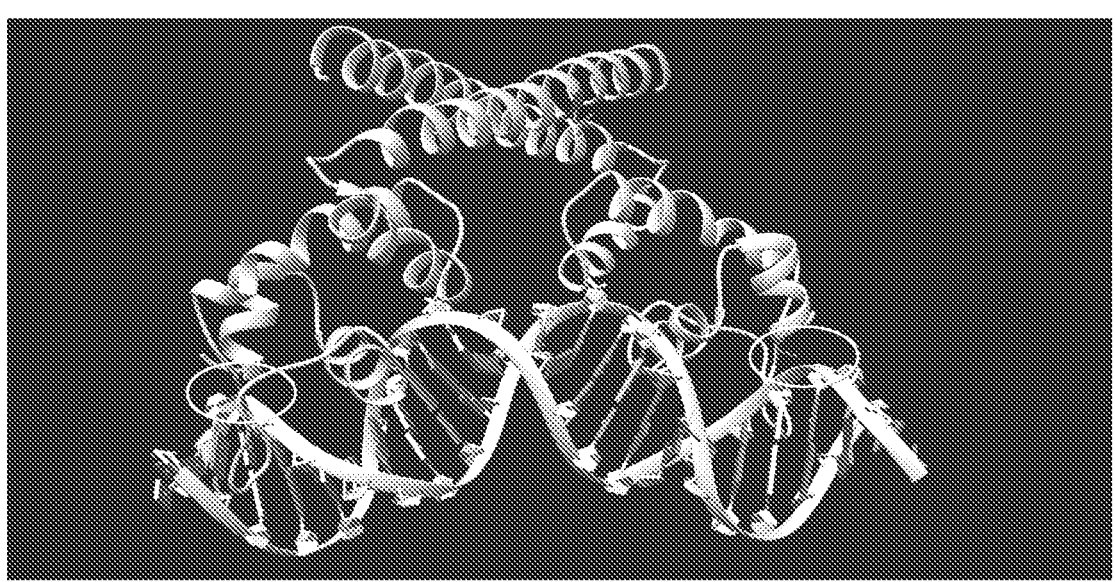
FIG. 9 shows the site of mutation of GolSmt1A38I. Single mutant at residue 38 from alanine to isoleucine (circled). Both residues are hydrophobic, isoleucine has 3 more carbons in the hydrophobic side chain than alanine. This may increase hydrophobicity and aggregation into the hydrophobic core and allow stronger binding with DNA.
Figure 10:
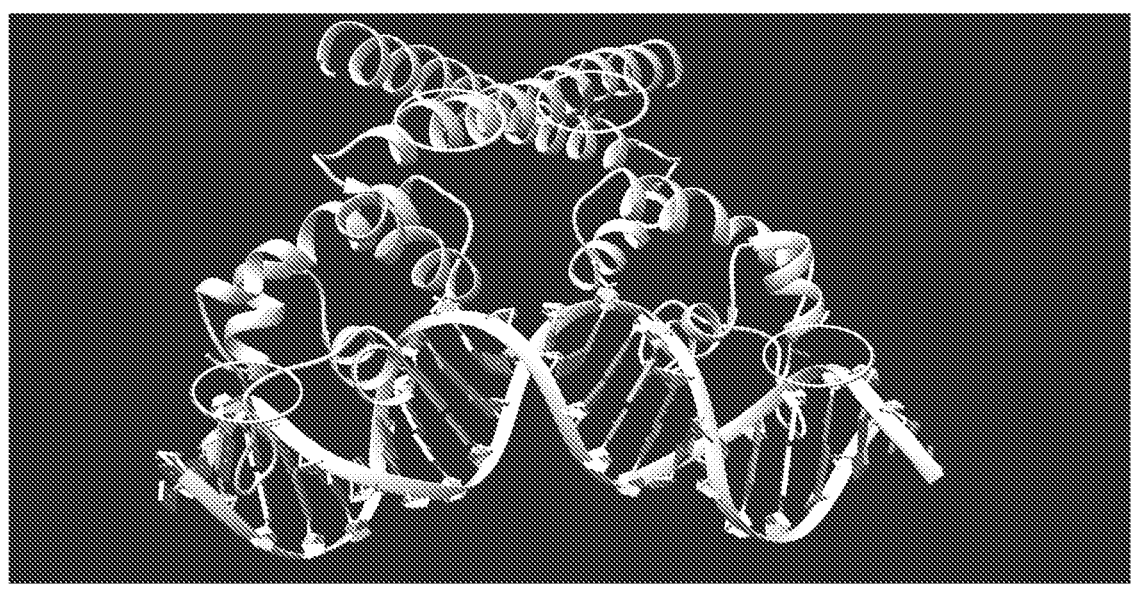
FIG. 10 shows the mutation of GolSmt2_A38Q N97D. Double mutant at residue 38 from alanine to glutamine (circles at DNA binding domain) and at residue 97 from asparagine to aspartic acid (circles at ion binding domain). For the first mutation. alanine is a nonpolar neutral amino acid while glutamine is polar neutral with an amide side chain, the longer polar side chain of glutamine may have better binding to DNA. For the second mutation, asparagine is polar neutral while aspartic acid is polar acidic, the negatively charged side chain of aspartic acid may have a higher affinity to positively charged gold ion or improve dimerization.
Figure 11:
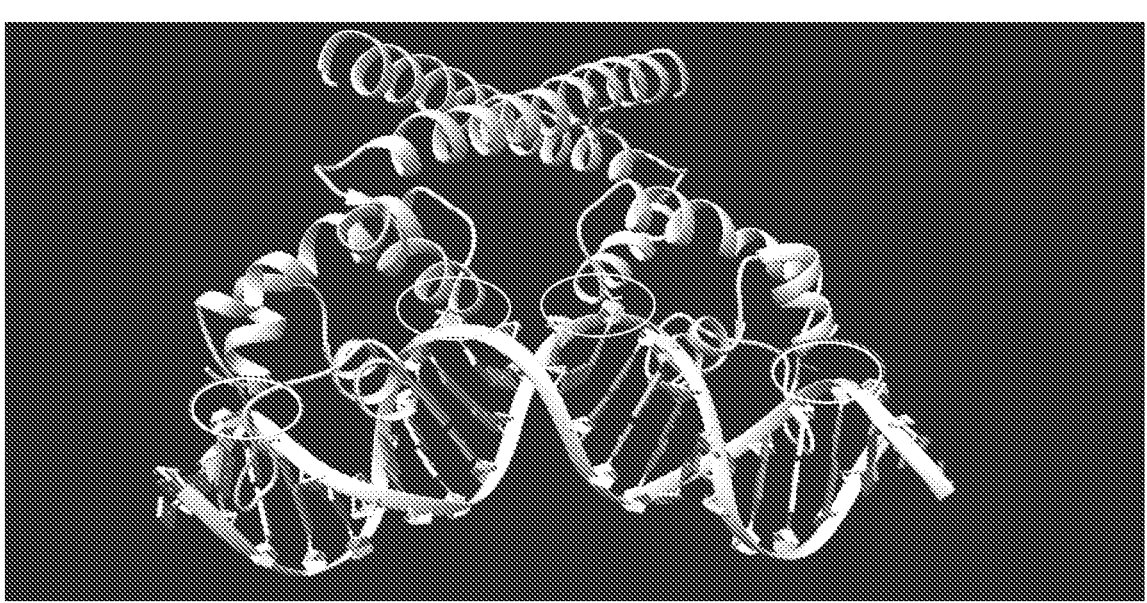
FIG. 11 shows mutation of GolSmt3_A38K V60L. Double mutant at residue 38 from alanine to lysine (outer circles) and at residue 60 from valine to leucine (inner circles). For the first mutation, alanine is nonpolar neutral while lysine is polar basic, lysine may allow better binding to the backbone phosphate groups. For the second mutation, both valine and leucine are nonpolar neutral and leucine has one more carbon in its side chain, this may increase overall hydrophobicity of the DNA binding domain.

Improving Dynamic Range and Sensitivity of Gold Sensor in *Chromobacterium violaceum* Via Mutagenesis After optimizing the circuitry and regulation machinery for the gold sensor, deep-scanning mutagenesis is next carried out on the GolS transcriptional activator to further increase the sensitivity and dynamic range of the gold sensor. Although the GolS protein structure has not been solved, GolS belongs to the MerR protein family with a helix-turn-helix DNA binding domain and a gold ion binding domain (FIG. 8A) [Checa, S. K. et al., *Mol Microbiol*, 63(5), 1307-1318 (2007)]. Using the optimized circuitry consisting of the low constitutively expressed GolS and $P_{golTS}$ driving RFP (FIG. 7), GolS mutants with wide dynamic range and high sensitivity compared to GolS wild type were screened and selected (FIG. 12). Four mutants were selected and characterized; GolSmt1 (A38I); GolSmt2 (A38Q and N97D); GolSmt3 (A38K and V60L); and GolSmt4 (D33P). The structure of wild type GolS and mutants GolSmt1, GolSmt2 and GolSmt3 are shown in FIGS. 8 to 11, respectively.

The gold sensor mutants have increased sensitivity and dynamic range than the wild type gold sensors reported so far (Table 1). The $B_{max}$, values increased with the largest fold change of 3.5-fold of the wild type $B_{max}$ value. The other parameters including K, n and C did not vary more than 2-fold, indicating that the other characteristics remain relatively similar.

TABLE 1

Parameter values from fitted response curves of gold sensor mutants.

|  | K (µM) | N | $B_{max}$ | C | $R^2$ | SEQ ID |
|---|---|---|---|---|---|---|
| GolS-mt1 | 2.25 ± 0.19 | 1.07 ± 0.07 | 45088 ± 1672 | 51 ± 225 | 0.998 | 27 |
| GolS-mt2 | 1.36 ± 0.15 | 1.12 ± 0.10 | 36074 ± 1611 | 54 ± 370 | 0.996 | 28 |
| GolS-mt3 | 1.48 ± 0.14 | 1.23 ± 0.11 | 41388 ± 1646 | 97 ± 392 | 0.996 | 29 |
| GolS-mt4 | 4.05 ± 0.87 | 1.15 ± 0.13 | 43451 ± 4356 | 78 ± 234 | 0.998 | 30 |
| GolS-WT | 5.51 ± 3.33 | 1.15 ± 0.29 | 12811 ± 3825 | 47 ± 111 | 0.994 | 24 | density at high concentrations of $Au^{3+}$ from 1 µM onwards. The toxicity to the cell could be due to the overexpression of GolT, a transmembrane efflux P-type ATPase, which may disrupt the integrity of the cell membrane if overexpressed. This low dynamic range and cell toxicity of the gold sensor in *C. violaceum* led to subsequent optimizations being carried out in the golTSB operon.

In order to reduce the leaky activation due to GolS, $P_{golTS}$ was replaced with a weak constitutive promoter to drive GolS expression, reducing the promoter strength and abolishing the positive feedback loop (FIG. 6B). Furthermore, GolT and GolB were removed to construct a minimal gold sensor and minimize possible detrimental effects on cell growth. The construct was subsequently tested with either $P_{golTS}$ (SEQ ID NO: 25) or $P_{golB}$ (SEQ ID NO: 26) driving the output fluorescent protein (FIGS. 6B and C). The maximum dynamic range is 151-fold for pGolTS (min 110 RFU max 16416 RFU) and 113-fold change (min 50 RFU max 1648 RFU) for pGolB between 0 and 10 µM $Au^{3+}$.

There is also a higher fold change of pGolTS compared to pGolB between 0 and 1 µM $Au^{3+}$ in which there are no observed toxicity to *C. violaceum*. There is a 38-fold change in dynamic range of gene expression for PgolB (min 50 max 1887 RFU) (FIG. 6B) and a 62-fold change in dynamic range of gene expression for PgolTS (min 110 max 6737 RFU) (FIG. 6C) from 0 to 1 µM $Au^{3+}$. The PgolTS construct was subsequently chosen as the gold sensor due to its higher dynamic range.

Sensitivity is a key parameter of sensors that determines its functionality in the system. The results obtained indicate that the gold sensor mutants are at least twice as sensitive to gold ions as the wild type gold sensor. There is a detectable fold change of at least three-fold induction at 8 nM gold ions for the gold sensor mutants while there was no detectable fold change for the wild type gold sensor (Table 2).

TABLE 2

Fold changes in output between ON and OFF state with increasing concentrations of $Au^{3+}$ for the wild type and the top three gold sensor mutants.

| Induction | Fold change | | | |
|---|---|---|---|---|
| ($Au^{3+}$) [µM] | GolSmt1 | GolSmt2 | GolSmt3 | WT |
| 0 | 1 | 1 | 1 | 1 |
| 0.0032 | 1 | 1 | 1 | 1 |
| 0.016 | 3 | 5 | 4 | 1 |
| 0.08 | 11 | 29 | 26 | 3 |
| 0.4 | 53 | 132 | 128 | 11 |
| 2 | 212 | 398 | 453 | 53 |
| 10 | 648 | 591 | 697 | 148 |

This value is more sensitive than the reported 33 nM gold ions with 2.3-fold induction as threshold for detection in an *E. coli* biosensor [Cerminati, S. et al., *Biotechnol Bioeng*, 108(11), 2553-2560 (2011)]. Gold sensor mutants achieved more than 10-fold change in output at just 80 nM $Au^{3+}$ while the wild type gold sensor has only 3-fold induction at that concentration of gold ions with sensitivity of gold ions at 4.5 RFU nM$^{-1}$. There are also low leaky expression of the OFF state in both wild type and mutant gold sensors. The OFF states are low with all outputs below 100 RFU. (GolSmt1— 51 RFU, GolSmt2—54 RFU, GolSmt3—97 RFU, WT—47 RFU). The gold sensor mutants are also able to produce higher maximum outputs than wild type gold sensor before toxic levels of gold ions are reached with more than 100-fold change (GolSmt1—45 088 RFU, GolSmt2—36 074 RFU, GolSmt3—41 388 RFU, WT—12 811 RFU).

Figure 13:
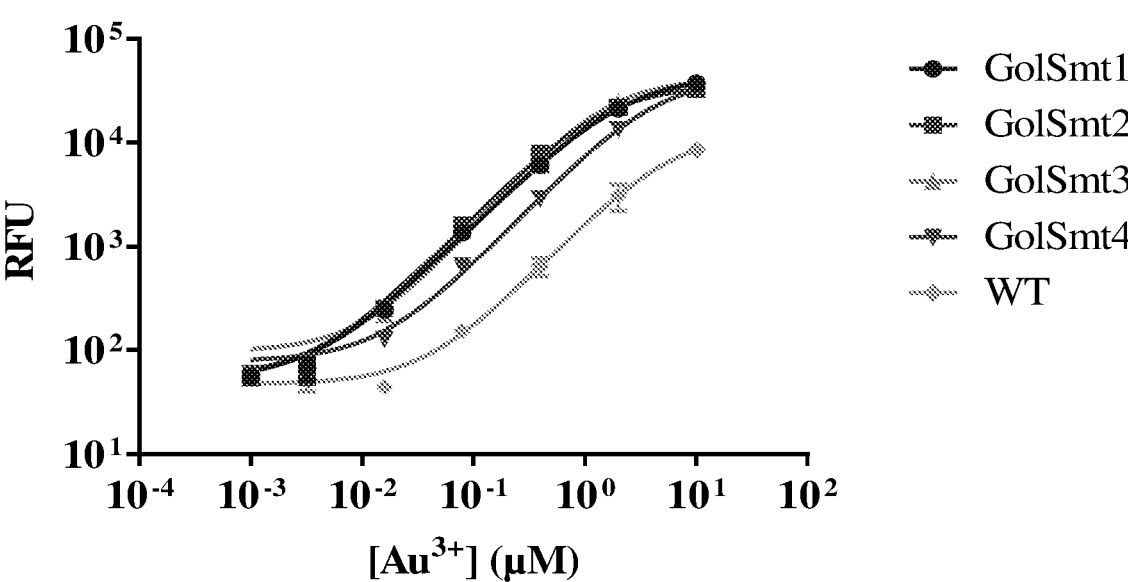
FIG. 13 shows response of wild type and top four gold sensor mutants to gold ions. The response curves are plotted and fitted to the Hill equation $Y=(B_{max}X^n)/(K^n+X^n)+C$. K: Activation $[Au^{3+}]$ threshold at half maximal RFU, n: Hill coefficient, C: Baseline RFU, $B_{max}$: Maximum RFU.

All the mutants are mutated in the helix-turn-helix DNA binding domain (left and right arrows, FIG. 8B), suggesting that the increased output of the transcriptional activator could be due to better binding to the promoter region and the subsequent activation of the promoter region, thereby leading to the higher maximum output of the gold sensor mutants (FIG. 13). The activator mutants also have increased affinity to gold ion binding, which is supported by the shift of the gold response function to the left (FIG. 13). At the same time, no leaky basal expression was found, suggesting that the mutations did not increase activation of the non-induced activator. In conclusion, the increased transcriptional output, increased affinity to gold ions, and tight expression of the gold sensing transcriptional activator mutants could serve as useful tools for future gold ion sensing applications.

Mutagenesis of Gold Sensor

Libraries of go/S mutants were created by QuikScan-19 and built using the QUIKCHANGE®-HT kit (Agilent Technologies, Santa Clara). Each amino acid is iteratively replaced with all 19 other amino acids, resulting in 19 mutagenic custom oligos for each amino acid in GolS to be used in the QUIKCHANGE® reaction. For the 154 aa GolS, excluding the first amino acid methionine, there is a total of 153×19=2907 possible single amino acid mutants to be generated. A total of 6 libraries spanning approximately 25 amino acids mutational regions each were generated across the protein according to manufacturer's protocol. Each library was subsequently transformed into competent *C. violaceum* and plated onto Tris minimal media 1.5% bacteriological agar with 30 µg/mL kanamycin and 2 µM AuCl.sub.3. Colonies were selected for higher RFP output compared to wild type GolS by observation under blue light and inoculated into 96-well plates for growth and subsequent fluorescence quantification with BioTek Synergy H1 microplate reader.

Fluorescence Measurement for Quorum and Gold Sensor Characterization

For gold sensor characterization, cells were grown in 96 deep well block (Nunc, Denmark) at 37° C. overnight from frozen stocks in LB media. Cells were diluted 1:200 in 96-well plates (Costar, Kennebunk) with 0.001 µM to 10 µM gold (III) chloride (Sigma Aldrich) in Tris minimal media (pH 7.5) containing 80 mM NaCl, 50 mM Tris, 22 mM glucose, 20 mM KCl, 20 mM NH$_4$Cl, 3 mM Na$_2$SO$_4$, 1 mM thiamine hydrochloride, 0.5 g/L yeast extract, 1 mM MgCl$_2$, 0.65 mM Na$_2$HPO$_4$ and 0.1 mM CaCl$_2$.

Diluted cells were subsequently grown in BioTek Synergy H1 microplate reader at 37° C. overnight. Red fluorescence was measured with excitation at 530 nm, emission at 600 nm (gain 50) every 10 minutes for 14-20 hours. Optical density was measured by absorbance at 600 nm. OD$_{600}$ and fluorescence values were blanked with media only without cells.

Example 4

Figure 14:
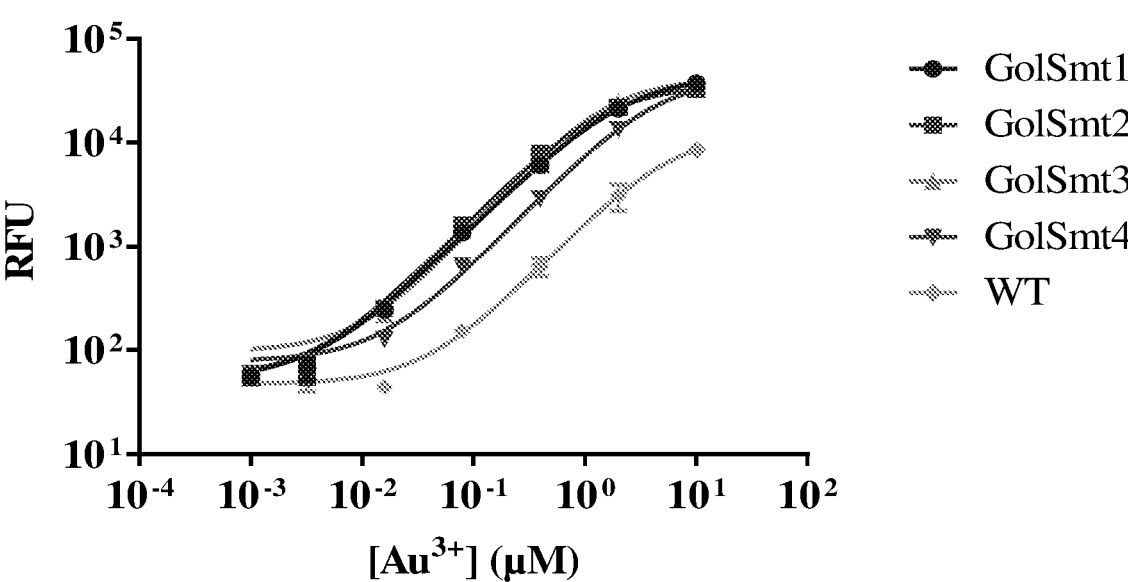
FIG. 14 shows a schematic of a synthetic circuitry providing a way to incorporate dynamic regulation into a new system. The quorum molecules allow autonomous switching ON of circuit while the gold sensor informs the circuitry to turn OFF when gold ions have been leached from the electronic waste.

Incorporation of Dynamic Regulation and Biosensors Via Synthetic Circuitry for a Robust Microbial Cell Factory In a gold bioleaching microbial cell factory, the two main constituents are, gold, which is the element of interest, and cyanide, which is the leachant needed to oxidize the solid gold into aqueous gold ions. This can pose a challenge to the living microbial cell factory as both gold ions and cyanide are highly toxic to microorganisms. Gold ions toxicity arise from the accumulation of Au(I)-S complexes which induces oxidative stress [Reith, F. et al., *Proc Natl Acad Sci USA*, 106(42), 17757-17762 (2009)] while cyanide inhibits the respiration process by binding to metals in the cytochrome oxidase [Knowles, C. J. *Bacteriol Rev*, 40(3), 652-680 (1976); Knowles, C. J. & Bunch, A. W. *Adv Microb Physiol*, 27, 73-111 (1986)]. Gold ions are shown to be toxic to bacteria at concentration as low as 0.35 µM [Shareena Dasari, T. P. et al., *Biochem Pharmacol* (*Los Angel*), 4(6), 199 (2015)] while cyanide toxicity to bacteria is as low as 0.4 µM [Liu, W. et al., *Chinese Journal of Chemistry*, 25(2), 203-207 (2007)]. Although many cyanide detoxifying mechanisms [Brysk, M. M. et al., *J Bacteriol*, 97(1), 322-327 (1969); Brysk, M. M. & Ressler, *Journal of Biological Chemistry*, 245(5), 1156-1160 (1970); Ressler, C. et al., *Biochemistry*, 12(26), 5369-5377 (1973)] in *C. violaceum* are present to protect itself from its own cyanide production, gold ions toxicity will be a new pressing challenge for the uninitiated *C. violaceum* during the gold bioleaching process. Hence, a dynamic ON-OFF circuit to switch ON the production of cyanide only at high cell density and to switch OFF the circuit upon sensing of toxic gold ions was constructed (FIG. 14).

The addition of the endogenous quorum sensing system into the circuitry will ensure that there is activation of the output only when the cell density is sufficiently high (FIG. 15). As the gold sensor which initiates the synthetic circuitry's negative feedback loop is an activator, a repressor has to be introduced downstream to mediate the repression. A characterized strong repressor of the TetR family that mediates up to 193-fold change in gene expression, PhlF (SEQ ID NO: 31) [Stanton, B. C. et al., *Nat Chem Biol*, 10(2), 99-105 (2014)], is added downstream of the gold sensor for transcriptional repression of the output. The operator of PhlF (SEQ ID NO: 32) is added downstream of the quorum sensing promoter for physical inhibition of RNAP in the transcription process (FIG. 15). The negative feedback loop provided by the gold sensor will grant real-time feedback on the bioleaching process and inhibit it when the cyanogenesis process has resulted in a high concentration of gold ions through cyanidation. Once it is expressed, the repressor will subsequently bind to the promoter region of the cyanogenesis gene. This means that no further expression of the bioleaching enzymes will occur when high concentration of gold ions is detected.

The circuitry is tested in continuous batch cultures with 1:600 dilution from the previous passage. The cultures are either grown in the presence of 2 µM Au$^{3+}$ to turn OFF the circuitry or in the absence of gold ions to turn ON the circuitry (FIG. 16). 2 µM of gold ions is used to induce the OFF state as it had resulted in the highest repression before gold ion toxicity was observed at 10 µM in our study. However, turning OFF the circuitry means that there should be low or no leaky expression at all. The basal expression level of the circuitry containing the wild type gold sensor in the OFF state increases over the cycles. OFF output increased from 245 RFU in the first cycle to 765 RFU and 1047 RFU for the second and third cycle respectively (FIG. 17). This is in contrast to the circuitry with the gold sensor mutants that have OFF state outputs consistently maintained below 250 RFU for all three cycles (FIG. 17).

The reduced basal expression of the GolS mutants resulted in increased dynamic range of expression through continuous cell cultures. While the dynamic range for WT gold sensor dropped from 15-fold in the first cycle to only 5-fold and 4-fold dynamic range in the second and third cycle respectively, the circuitry containing GolS mutants maintained dynamic range above 10-fold for all three cycles (FIG. 17). This maintenance of high dynamic range in the circuitry containing the GolS mutants will give robustness and increased functionality of the gold leaching microbial cell factor to undergo multiple ON-OFF cycles.

The increased robustness of the GolS mutant circuitry is further supported by the distinct ON-OFF populations maintained through continuous cycles as seen from the representative flow cytometer histograms (FIG. 18), where (A) is WT; (B) GolSmt1; (C) GolSmt2 and (D) GolS mt3. The observed spreading of the OFF cell population in the WT gold sensor (FIG. 18A) suggests that the increased heterogeneity in the cell population expression is the main cause of the decrease in dynamic range of the circuitry. The stronger OFF state maintenance of the circuitry containing the gold sensor mutants can be attributed to the increased sensitivity to gold ions and the increased dynamic range of the gold sensor. The higher expression of the PhIF repressor under the same induction of 2 $\mu$M Au$^{3+}$ can lead to better repression of the quorum sensing promoter even as the cell passages increase.

Another observation is that two of the GolS mutants (GolSmt2, FIG. 18C and GolSmt3, FIG. 18D) have increasing population remaining in the OFF state over the three cycles, leading to slight reductions in the dynamic ranges. This could be due to the insufficient dilution of the PhIF repressor over the cycles, which results in a small population of the cells remaining in the OFF state. Although the GolS mutants allowed increased expression of the PhIF repressor for better maintenance of the OFF state output, it may have been too strong such that the cell dilutions of the PhIF repressor are inadequate to switch back the circuitry to the ON state. This suggests that GolSmt2 and GolSmt3 may not be as suitable as gold sensors for robust continuous ON-OFF cycles in the gold bioleaching synthetic circuitry.

Figure 16:
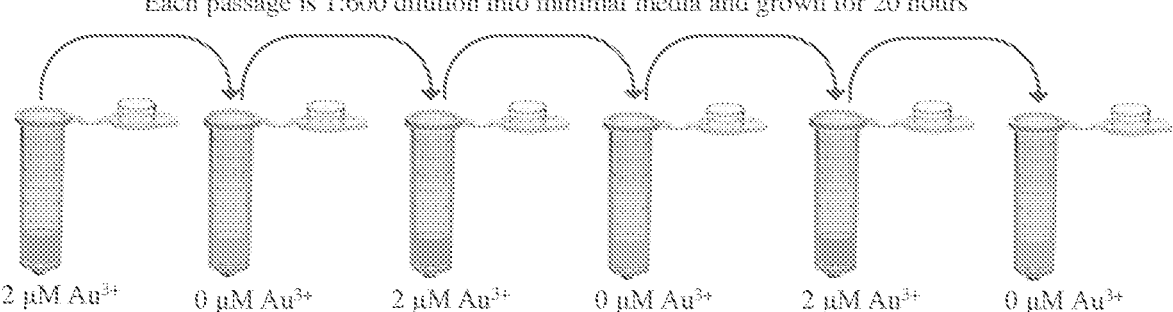
FIG. 16 shows schematic of batch culture of *Chromobacterium violaceum* for ON-OFF output in response to gold ions. To investigate the ON-OFF output of the circuit, small-scale batch cultures of *C. violaceum* were cultured in 300 μL of Tris minimal media supplemented with 30 μg/mL kanamycin in 2 mL eppendorf tubes for 24 hours at 37° C. 1:600 dilution of the stationary phase culture was carried out for each passage with addition of 2 μM AuCl.sub.3 on alternate passages. End-point single cell fluorescence output was measured using BD ACCURI™ C6 Flow cytometer (BD Biosciences, Singapore) with a flow rate of 14 μL/min and a core size of 10 μm, collecting 10000 events for each sample. Fluorescence excitation at 561 nm and detection at 610/620 nm was taken. Cells were gated with forward scatter and side scatter. Background fluorescence of control cells without RFP was subtracted from mean fluorescence values.
Figure 17:
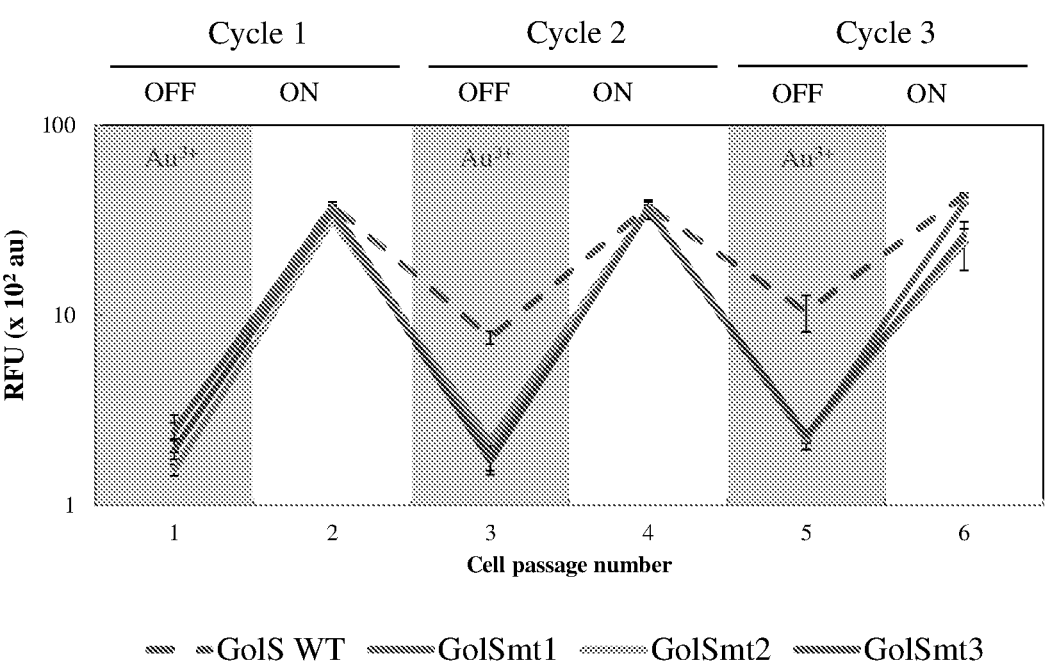
FIG. 17 shows a graph of reduced basal leaky expression of circuitry with mutant gold sensors compared to wild type gold sensors through continuous cell passages in the presence or absence of gold ions. Each passage is 1:600 dilution of the previous passage in either minimal media without $Au^{3+}$ to turn ON the circuitry or with 2 μM $Au^{3+}$ to turn OFF the circuitry.
Figure 18:
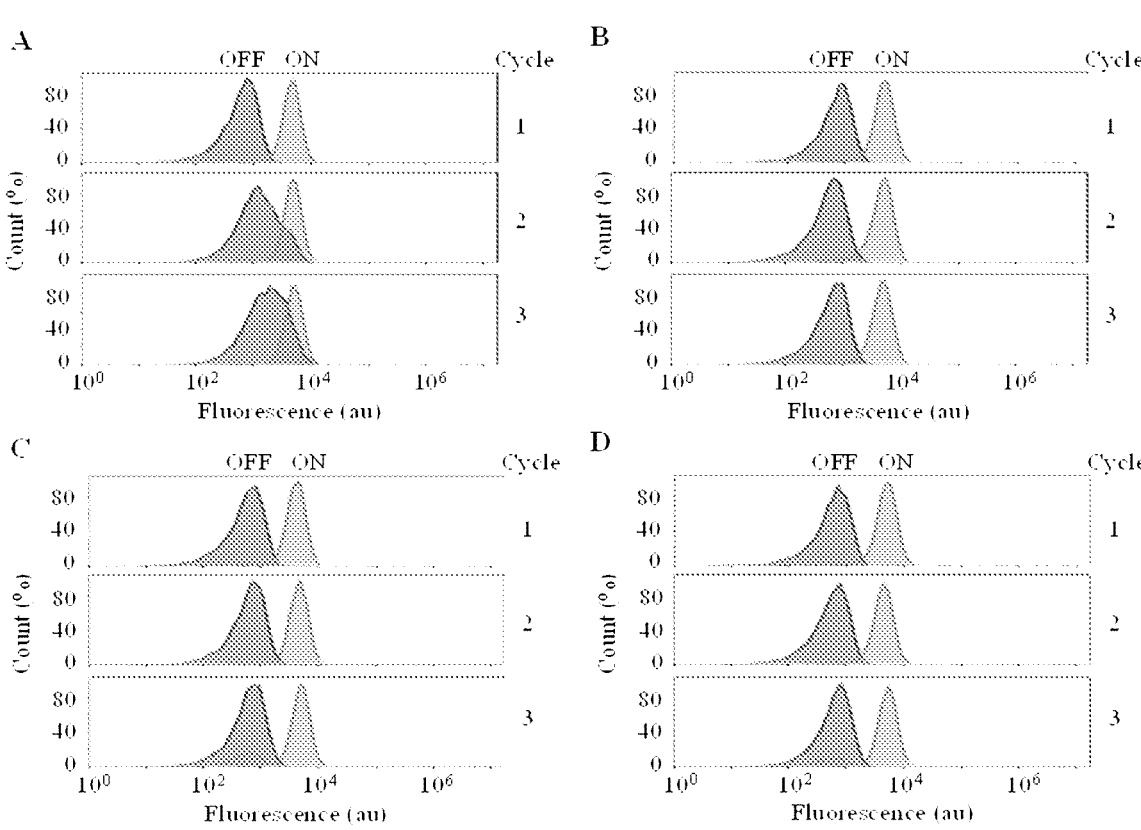
FIG. 18 shows graphs representing distinct ON and OFF populations through three cycles of ON-OFF with GolS mutants (B-GolSmt1, C-GolSmt2, D-GolS mt3) while ON-OFF populations merged in circuitry containing wild type gold sensor (A).

The gold sensor mutants increased the robustness of the circuitry over three cycles of ON-OFF, consisting of six cell passages (FIGS. 16 to 18). This contributes significantly to the development of a robust gold bioleaching microbial cell factory as the gold ions toxicity to the cells will mean that many cycles of gold leaching are needed.

Example 5

Directed Evolution of Mercury(II) Reductase Toward Gold Reduction
Determination of Minimal Inhibitory Concentration of Au(III)

Au(III) is known to be toxic to many bacterial cells due to its high affinity for thiol groups (—SH) and thus can affect many metabolically important enzymes and membrane-bound proteins. E. coli cells expressing MerA mutant enzyme with improved gold reduction activity could potentially exhibit more resistance to a toxic level of Au(III) supplemented in the culture media.

Figure 23:
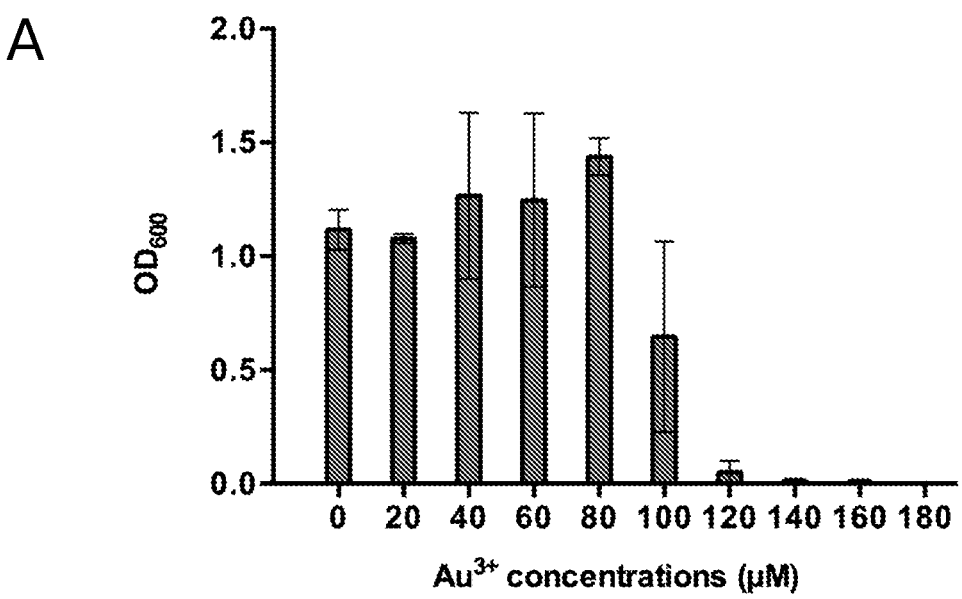
FIG. 23 shows the effect of $Au^{3+}$ on *E. coli* Rosetta (DE3) pLysS cell growth in (A) liquid broth and (B) agar plates.
Figure 23:
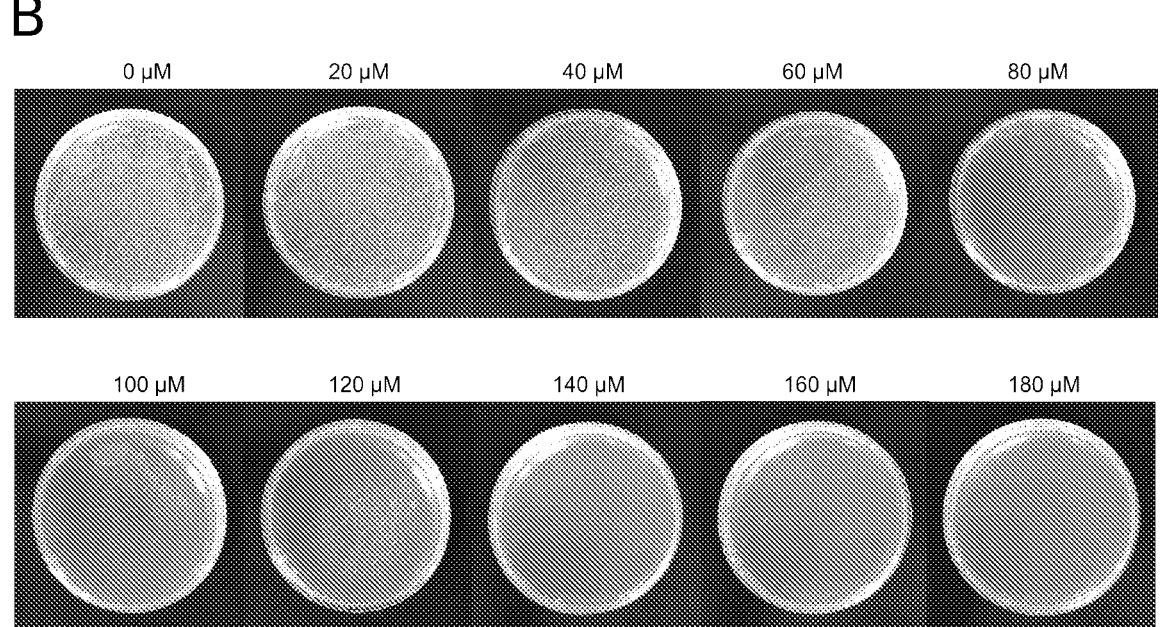

For the broth method, ligation mixture was transformed into E. coli Rosetta(DE3) pLysS competent cells, which were plated on normal LB agar plates. For broth medium, a 5 mL of Tris-buffered low-phosphate medium supplemented with the same antibiotics and different concentrations of AuCl$_3$ was inoculated with a single colony at 37° C. for 24 h. OD$_{600}$ was then measured to compare cell growth. The lowest concentration of heavy metals that completely prevents growth was defined as MIC. It is shown in FIG. 23A that cells were unable to grow at Au$^{3+}$ concentration greater than 140 $\mu$M.

For the plate method E. coli cells expressing wild-type MerA, cells were cultured, diluted and plated on Tris-buffered low-phosphate agar medium (Tris 6.06 g/L, NaCl 4.68 g/L, KCl 1.49 g/L, NH$_4$Cl 1.07 g/L, Na$_2$SO$_4$ 0.43 g/L, MgCl$_2$.6H$_2$O 0.2 g/L, CaCl$_2$.2H$_2$O 0.03 g/L, Na$_2$HPO$_4$.12H$_2$O 0.23 g/L, glucose 5.0 g/L, yeast extract 0.5 g/L and agar 15 g/L) supplemented with 100 $\mu$g/mL of ampicillin, 34 $\mu$g/mL of chloramphenicol, 0.1 mM of IPTG and different concentrations of AuCl$_3$, and grown at 37° C. for 24 h. Results show that as Au$^{3+}$ concentration increased, fewer colonies were observed on the plates. Cell growth was completely inhibited as Au$^{3+}$ concentration reached 160 $\mu$M (FIG. 23B).

The toxicity of gold is probably due to its high affinity for thiol groups (—SH) that exist in many metabolically important enzymes and membrane-bound proteins. When bound to gold ions, these proteins are no longer accessible to their native biologically relevant metal ions. The broth method exhibited a slightly lower minimal inhibitory concentration compared to the plate method. This difference could come from the different distribution pattern of Au$^{3+}$ ions between plates and liquid broth.

Directed Evolution Library Construction

The synthetic codon-optimized gene encoding mercury (II) reductase (MerA) was cloned in-frame with an N-terminal 6× His tag into the expression vector pET20b (Novagen) using restriction enzymes NdeI and XhoI. To evolve MerA with improved gold reducing activity, mutant libraries were constructed using error-prone PCR and site-saturation mutagenesis.

Error-prone PCR of MerA gene was carried out on the MerA gene (SEQ ID NO: 33; SEQ ID NO: 34) with the GeneMorph II Random Mutagenesis kit (Agilent Technologies) according to the manufacturers' protocol, with 50-100 ng of target DNA in the PCR reaction to achieve a medium mutation frequency (4.5-9 mutations/kb), which was confirmed by sequencing a few randomly picked colonies. The following primers were used: epPCR-fw: 5'-GTGGTGGTGGTGGTGCTCGAGTTA-3' (SEQ ID NO: 1) and epPCR-rv: 5'-GATATACATATGCACCACCAT-CACCATCAT-3' (SEQ ID NO: 2). The thermocycling program consisted of an initial denaturation at 95° C. for 2 min, 30 cycles of denaturation at 95° C. for 30 s, annealing at 55° C. for 30 s, and extension at 72° C. for 1.5 min, with the last cycle followed by a 10-min extension at 72° C. The PCR product was then treated with DpnI for template degradation and purified using the QIAquick PCR purification kit (Qiagen). The purified DNA fragment was double digested with NdeI and XhoI, purified and ligated into the pET20b vector.

Figure 22:
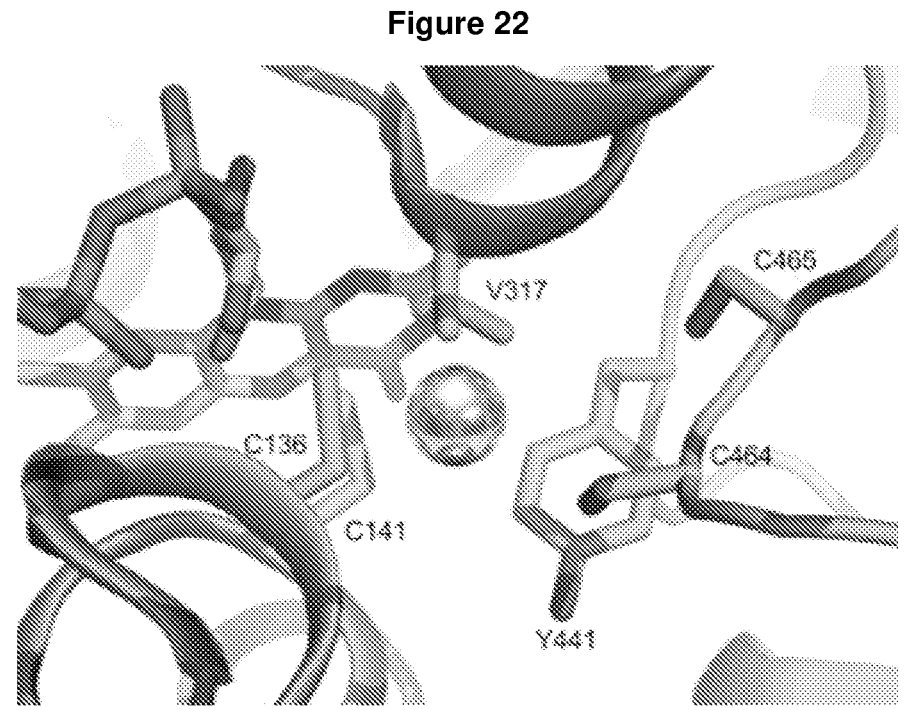
FIG. 22 shows target sites in MerA protein for sequence modification to alter metal binding affinity and/or specificity.

Multiple site-saturation mutagenesis was done by overlap-extension PCR using degenerate primers containing NNK at the target sites V317, Y441, C464 and C465'. These positions are in close contact with the potential gold binding site within the active site of MerA (FIG. 22). The redox active cysteines C136 and C141 were kept unchanged to prevent possible redox activity loss. The primers used are listed in Table 3.

TABLE 3

Sequences of the primers used for
site-saturation mutagenesis

| Primer | Sequence [a] | SEQ ID |
|---|---|---|
| T7-fw | 5'-TAATACGACTCACTATAGGG-3' | 3 |
| T7-rv | 5'-GCTAGTTATTGCTCAGCGGTG-3' | 4 |
| V317NNK-fw | 5'-GATCAACCGCAGTTC*NNK*TATGT TGCGGCTGCC-3' | 5 |
| V317NNK-rv | 5'-GGCAGCCGCAACATA*MNN*GAACT GCGGTTGATC-3' | 6 |
| Y441NNK-fw | 5'-CGGATCAGCTGTTTCCG*NNK*CTG ACAATGGTCGAAG-3' | 7 |
| Y441NNK-rv | 5'-CTTCGACCATTGTCAG*MNN*CGGA AACAGCTGATCCG-3' | 8 |
| C464NNK-fw | 5'-GATGTCAAACAATTGTCG*NNK*NN* KGCAGGCTAACTCGAGCACC-3' | 9 |
| C464NNK-rv | 5'-GGTGCTCGAGTTAGCCTGC*MNN*M *NN*CGACAATTGTTTGACATC-3' | 10 |

[a] Degeneracy alphabet: N = (A, T, C, G); K = (T, G); M = (A, C)

PCR reactions were performed with primer pairs T7-fw/ V317NNK-rv, V317NNK-fw/Y441NNK-rv, Y441 NNK-fw/C464NNK-rv and C464NNK-fw/T7-rv, to generate partially overlapping DNA fragments. The reaction mixture in a total volume of 50 µL containing 50 ng of the pET20bMerA plasmid, 500 nM of each primer and 1× PrimeSTAR Max Premix (Clontech), was incubated with 30 cycles of 98° C. for 10 s, 55° C. for 5 s and 72° C. for 10 s. The PCR products were purified and equimolar amount of each fragment was mixed in 1× PrimeSTAR Max Premix for a short overlap extension reaction (5 cycles of 98° C. for 10 s, 55° C. for 5 s, 72° C. for 10 s), and 1 µL of the reaction mixture was used as the template to amplify the full length MerA mutant gene using primers epPCR-fw and epPCR-rv. The PCR product was purified, digested with NdeI and XhoI, and ligated into the pET20b vector.

Selection for Gold Tolerant Mutants

Figure 24:
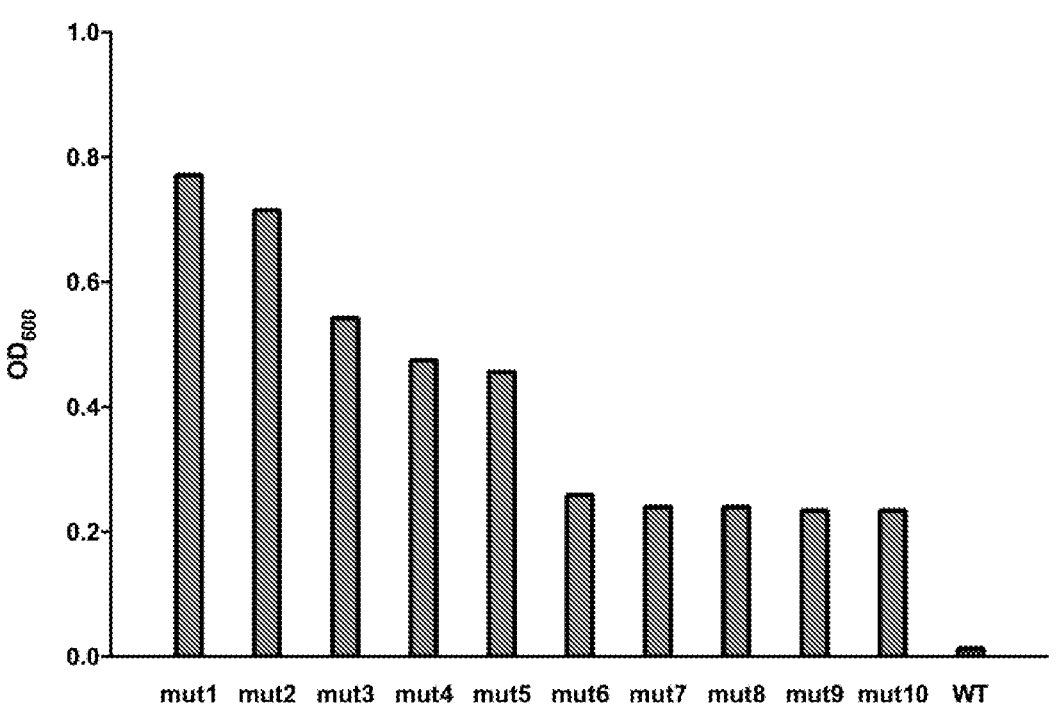
FIG. 24 shows the $OD_{600}$ of the wild-type MerA-expressing *E. coli* cells and all the mutants from $Au^{3+}$ containing agar plate

The ligation mixture from either error-prone PCR or site-saturation mutagenesis was used to transform *E. coli* Rosetta(DE3)pLysS competent cells, and the transformants were plated on Tris-buffered low-phosphate agar medium (Tris 6.06 g/L, NaCl 4.68 g/L, KCl 1.49 g/L, NH$_4$Cl 1.07 g/L, Na$_2$SO$_4$ 0.43 g/L, MgCl$_2$.6H$_2$O 0.2 g/L, CaCl$_2$.2H$_2$O 0.03 g/L, Na$_2$HPO$_4$.12H$_2$O 0.23 g/L, glucose 5.0 g/L, yeast extract 0.5 g/L and agar 15 g/L) supplemented with 100 µg/mL of ampicillin, 34 µg/mL of chloramphenicol, 0.1 mM of IPTG and 250 µM of AuCl$_3$, and grown at 37° C. for 24 h. Colonies were then picked and grown in liquid Tris-buffered low-phosphate media supplemented with 100 µg/mL of ampicillin, 34 µg/mL of chloramphenicol, 0.1 mM of IPTG and 300 µM of AuCl$_3$. After a few rounds of selection, 10 mutants were obtained that showed substantially better cell growth at toxic level of Au$^{3+}$ (300 µM), where cells expressing wild-type MerA could barely grow (FIG. 24). It is worth mentioning that all the colonies that survived two selections were from the site-saturation library, indicating that this semi-rationally designed library, rather than the one generated by random mutagenesis, may contain functionally improved variants with a better chance. The improved tolerance compared to the wild type may come from two sources: 1) detoxification by MerA that enzymatically reduce Au$^{3+}$ ions, and 2) sequestering of Au$^{3+}$ by MerA binding it.

Figure 25:
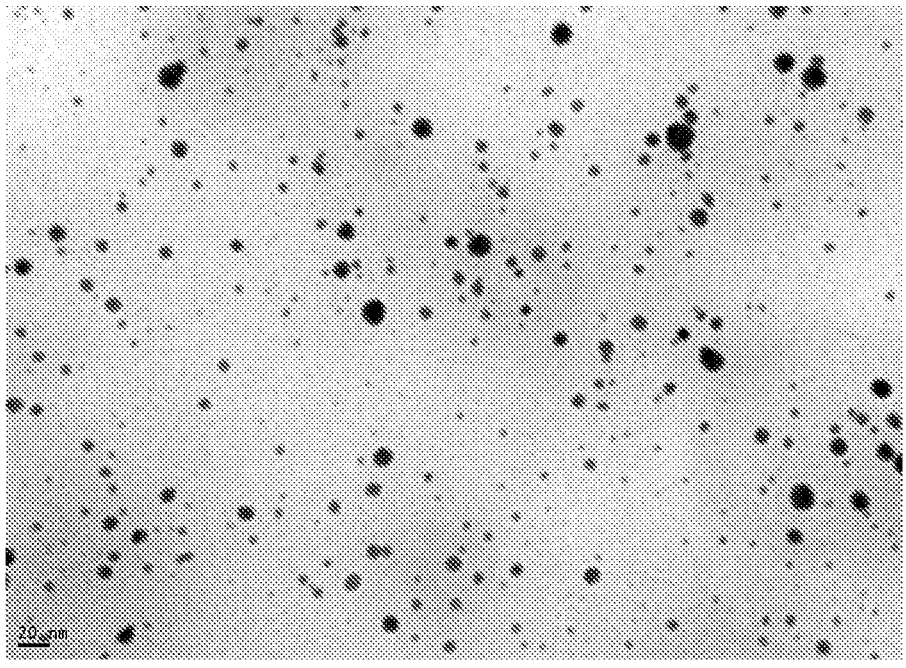
FIG. 25 shows a TEM image of gold nanoparticles synthesized by MerA mutants.

MerA mutants were produced that synthesized gold nanoparticles from AuCl$_3$ as shown in a TEM image (FIG. 25). Through our directed evolution methods, we have identified an enhanced gold-reductase, a MerA mutant V317S. This mutant has kinetic parameters listed in Table 5. The enhanced gold reductase has an increase of 67-fold in catalytic efficiency in reducing Au$^{3+}$ to elemental gold (Au$^0$).

TABLE 5

Kinetic parameters of enhanced gold-reductase

| | Au$^{3+}$ Substrate | | |
|---|---|---|---|
| Parameter | Wild-type MerA | V317S Mutant MerA | Fold-increase |
| $K_M$ (µM) | 380 ± 140 | 50 ± 8 | — |
| $k_{cat}$ (s$^{-1}$) | 6.8 ± 1.9 × 10$^{-3}$ | 58 ± 2.0 × 10$^{-3}$ | 8.5 |
| $k_{cat}/K_M$ (M$^{-1}$ s$^{-1}$) | 1.8 ± 1.3 × 10$^1$ | 1.2 ± 0.25 × 10$^3$ | 67 |

Further Improved Mutants

Figure 26:
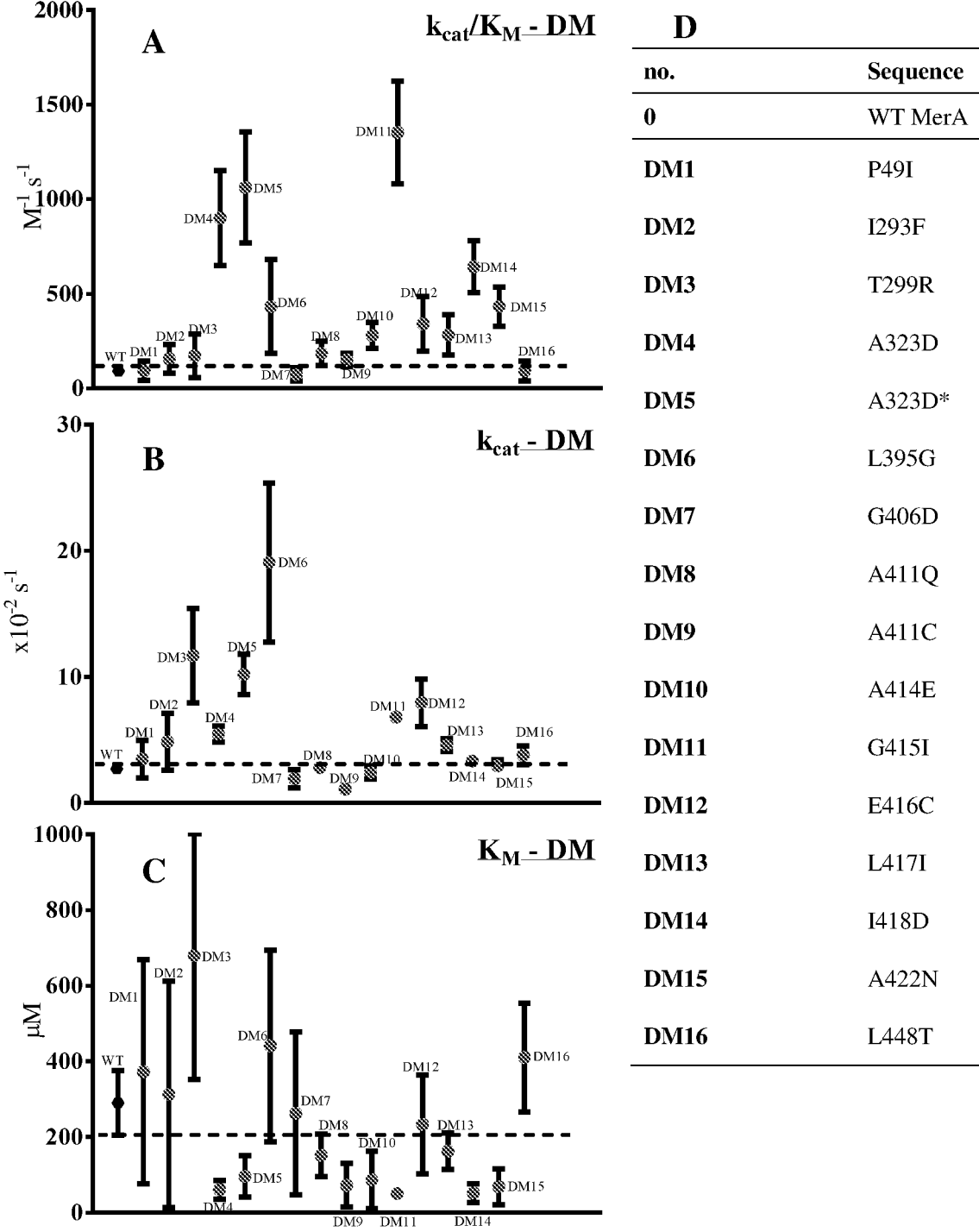
FIG. 26 shows a comparison of $Au^{3+}$ reduction kinetic parameters for mutants identified through DM selection. ●—DM mutant, ◆—WT MerA. For (A) & (B) Mutants above the dotted line show improvement in $k_{cat}/K_M$ or $k_{cat}$ over WT MerA (A) Comparison of $k_{cat}/K_M$ values for DM mutants (B) Comparison of $k_{cat}$ values for DM mutants (C) Comparison of $K_M$ values for DM mutants. Mutants below the dotted line show improvement in $K_M$ over WT MerA (D)—Table of mutants and associated sequences.

MerA's gold reduction capability has been established previously with a catalytic efficiency of 9.1±3.2× 10$^1$ M$^{-1}$ s$^{-1}$. A combination of directed evolution and rational design approaches was used to generate a library of improved Au$^{3+}$ reducing MerA mutants. Over 50% of the mutants isolated showed improved activity with the highest improving mutant displaying up to 15-fold improvement in catalytic efficiency (FIG. 26). Mutant DM11 (G415I) (SEQ ID NO: 48) displayed the greatest improvement in catalytic efficiency (15-fold increase) as a result of improvement in both turnover ($k_{cat}$) and binding affinity ($K_M$). The kinetic parameters of all mutants can be found in Table 6.

Figure 27:
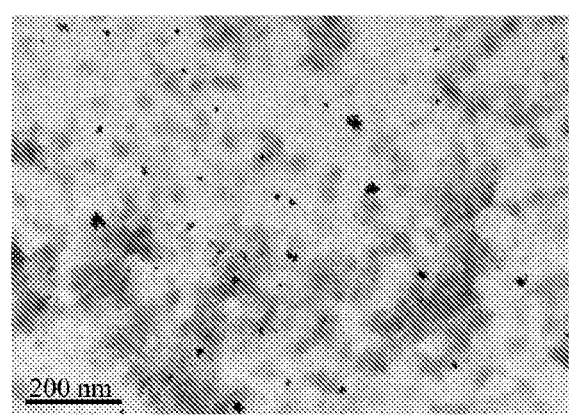
FIG. 27 shows TEM images of AuNP recovered through reduction of $AuCl_3$ via (A) WT MerA (B) DM11.
Figure 27:
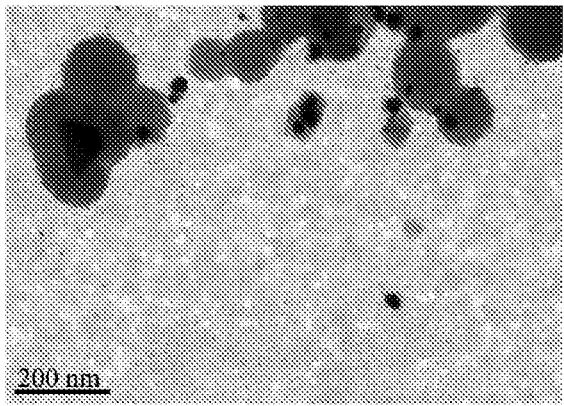
Figure 28:
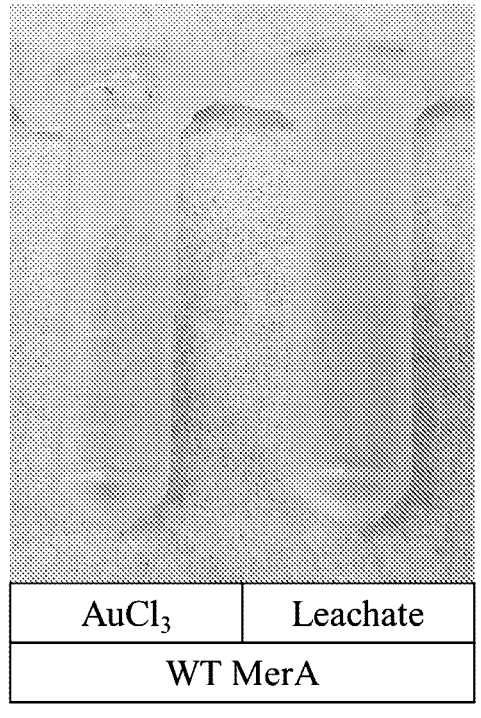
FIG. 28 shows in vivo reduction of $Au^{3+}$ from $AuCl_3$ and leachate via (A) WT MerA (B) DM11.
Figure 28:
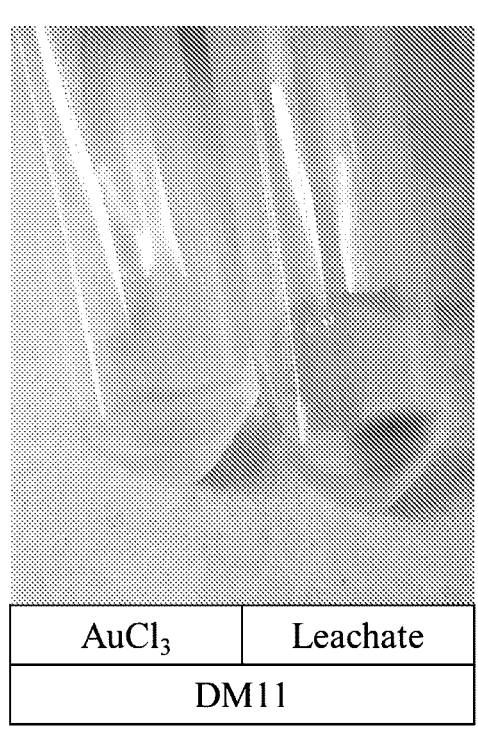
Figure 29:
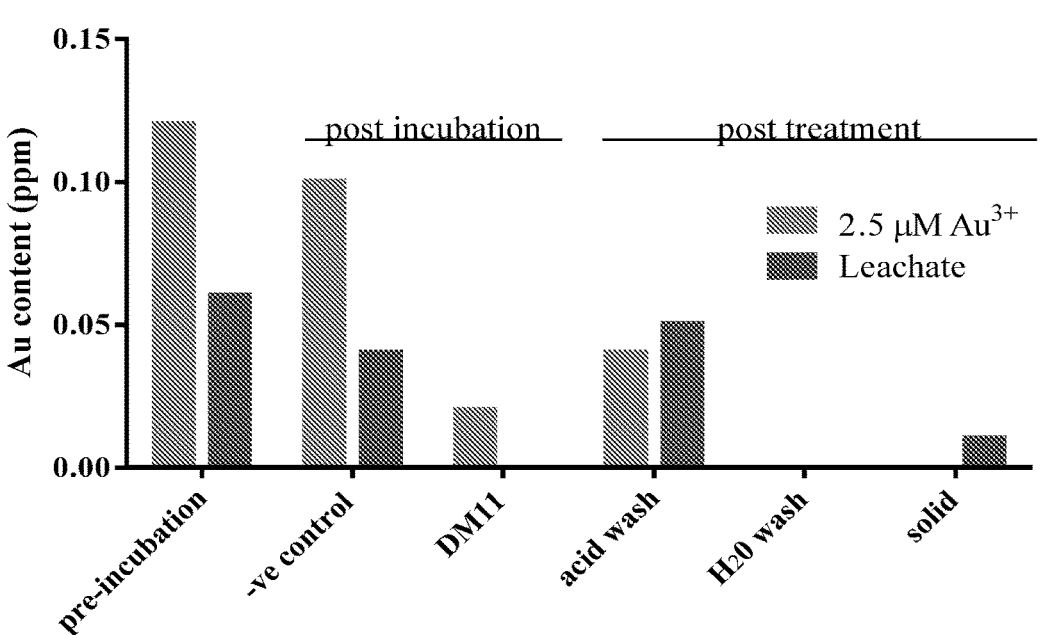
FIG. 29 shows a comparison of Au content before and after recovery by DM11, and at downstream processing stages.

This improvement in catalytic efficiency is also reflected in the complexity of gold nanoparticles (AuNPs) formed after reduction has occurred. DM11 produces AuNPs of greater size and complexity as compared to MerA (FIG. 27). This improvement in catalytic efficiency is also reflected in the improved reduction and recovery of gold by DM11 from electronic waste leachate as compared to WT MerA (FIG. 28). DM11 is equally effective at recovering Au$^{3+}$ from a solution of AuCl$_3$ (67%) and electronic waste leachate (67%) (FIG. 29).

TABLE 6

Kinetic parameters for mutants identified through DM selection. Mutants
in the dimerization region (DM10-15) and residue position 323 (DM4
and DM5) show the greatest increases in catalytic efficiency.

| no. | Sequence | $k_{cat}$ (×10$^{-2}$ s$^{-1}$) | | $K_M$ (µM) | | $k_{cat}/K_M$ (×10$^1$ M$^{-1}$ s$^{-1}$) | | SEQ ID NO |
|---|---|---|---|---|---|---|---|---|
| 0 | WT MerA | 2.7 ± 0.3 | — | 290 ± 85 | — | 9.1 ± 3.2 | — | |
| DM1 | P49I | 3.5 ± 1.5 | +29% | 370 ± 300 | −29% | 9.3 ± 5.0 | +3% | 38 |

TABLE 6-continued

Kinetic parameters for mutants identified through DM selection. Mutants
in the dimerization region (DM10-15) and residue position 323 (DM4
and DM5) show the greatest increases in catalytic efficiency.

| no. | Sequence | $k_{cat}$ $(\times 10^{-2}\,s^{-1})$ | | $K_M$ ($\mu$M) | | $k_{cat}/K_M$ $(\times 10^1\,M^{-1}\,s^{-1})$ | | SEQ ID NO |
|---|---|---|---|---|---|---|---|---|
| DM2 | I293F | 4.9 ± 2.3 | +80% | 310 ± 300 | −8% | 16 ± 8 | +71% | 39 |
| DM3 | T299R | 11.7 ± 3.7 | +333% | 680 ± 330 | −134% | 17 ± 11 | +89% | 40 |
| DM4 | A323D | 5.4 ± 0.6 | +102% | 61 ± 25 | +79% | 90 ± 25 | +889% | 41 |
| DM5 | A323D* | 10.2 ± 1.6 | +277% | 96 ± 55 | +67% | 106 ± 29 | +1068% | 42 |
| DM6 | L395G | 19.1 ± 6.3 | +607% | 440 ± 250 | −52% | 43 ± 25 | +375% | 43 |
| DM7 | G406D | 1.9 ± 0.7 | −29% | 260 ± 210 | +10% | 7.3 ± 3.4 | −20% | 44 |
| DM8 | A411Q | 2.8 ± 0.4 | +4% | 150 ± 57 | +48% | 18 ± 6.3 | +102% | 45 |
| DM9 | A411C | 1.1 ± 0.2 | −60% | 72 ± 58 | +75% | 15 ± 3.5 | +65% | 46 |
| DM10 | A414E | 2.4 ± 0.5 | −10% | 87 ± 76 | +70% | 28 ± 6.9 | +207% | 47 |
| DM11 | G415I | 6.8 ± 0.3 | +152% | 50 ± 11 | +83% | 135 ± 27 | +1386% | 48 |
| DM12 | E416C | 8.0 ± 1.9 | +195% | 230 ± 130 | +19% | 34 ± 14 | +274% | 49 |
| DM13 | L417I | 4.6 ± 0.5 | +70% | 160 ± 49 | +44% | 28 ± 11 | +211% | 50 |
| DM14 | I418D | 3.3 ± 0.3 | +23% | 52 ± 25 | +82% | 64 ± 14 | +606% | 51 |
| DM15 | A422N | 3.0 ± 0.5 | +9% | 69 ± 47 | +76% | 43 ± 10 | +375% | 52 |
| DM16 | L448T | 3.8 ± 0.7 | +40% | 410 ± 140 | −42% | 9.2 ± 5.2 | +1% | 53 |

*(delΔ324-365)

Figure 30:
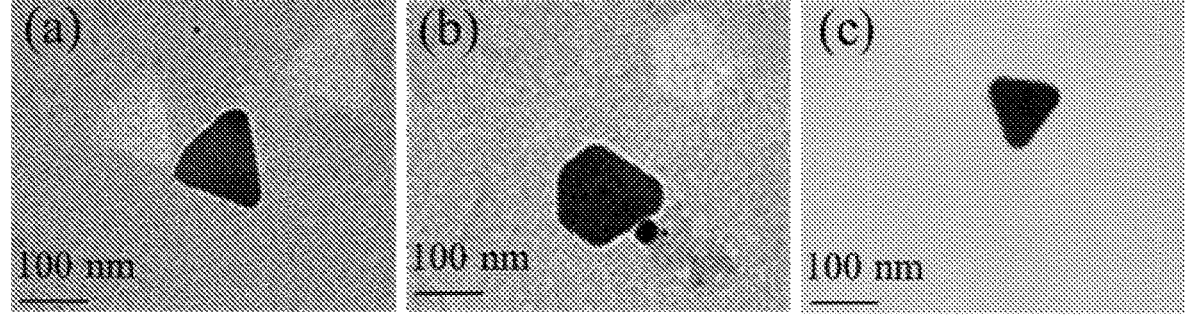
FIG. 30 shows TEM images of AuNP recovered by DM11 from $AuCl_3$ and electronic waste leachate. (A) Truncated tetrahedron AuNP recovered from $AuCl_3$ (B) Truncated bi-tetrahedron AuNP recovered from $AuCl_3$ (C) Truncated tetrahedron AuNP recovered from leachate.

However, with reduction from $AuCl_3$, AuNPs of increasing complexity can be observed, while with reduction from leachate, AuNPs of limited complexity can be observed (FIG. 30). This is likely due to the overall lower quantity of $Au^{3+}$ in leachate. It is believed that if this limitation can be overcome, a greater improvement in gold recovery can be observed. MerA is an essential enzyme in bacterial mercury resistant system. Based on its reaction mechanism and available crystal structure, we envisioned that it could also be engineered for efficient gold reduction. To this end, a high-throughput selection procedure was established that involves toxic agar plate selection followed by a more stringent liquid culture selection. Mutant libraries were constructed by both error-prone PCR and multiple site-saturation mutagenesis, and were subjected to this two-step selection. As a result, we have identified mutants of MerA with enhanced gold-reduction/gold-recovery properties. This constitutes the Synthetic Metal Recovery portion of Synthetic Lixiviant Biology.

Protein Expression and Purification

Recombinant proteins were expressed using the T7 expression system. Rosetta(DE3)pLysS cells were transformed with the plasmids and selected on LB agar plates containing 100 µg/mL ampicillin and 34 µg/mL chloramphenicol. A single colony was picked into 5 mL of LB medium containing the two antibiotics and grown overnight at 37° C. A 100-fold dilution was made, and the culture was grown at 37° C. until $OD_{600}$ reaches 0.6. Protein expression was then induced by adding isopropyl β-D-thiogalactoside (IPTG) at a final concentration of 0.1 mM. After induction the cells were grown at 16° C. for a further 18 h. The cells were lysed by sonication, and the His-tagged proteins were purified from the cleared lysates on nickel-chelate columns (Qiagen). The protein samples in the eluates (500 mM imidazole, 50 mM Tris-Cl pH 7.5, 300 mM NaCl) were concentrated and dialysed against 20 mM sodium phosphate (pH 7.4) by Amicon Ultra centrifugal filters (Millipore).

Gold Reduction Assay

The enzyme assays were carried out at 25° C. in 20 mM sodium phosphate, pH 7.4, 200 µM NADPH, 100 µM $AuCl_3$. The oxidation of NADPH was followed spectrophotometrically at 340 nm. Units of enzyme activity are defined as the amount of enzyme that catalyzes the Au-dependent oxidation of 1.0 µmol of NADPH per min.

Example 6

Kinetic Parameters for Gold Reduction by MerA

The kinetic parameters of the purified mercuric reductase enzyme (MerA) were determined for substrate $AuCl_3$ using a continuous spectrophotometric assay (Scheme 1).

Scheme 1:
Assay monitoring activity of MerA via change in absorbance at 340 nm.

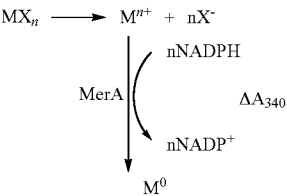

M refers to either $Hg^{2+}$ or $Au^{3+}$ with X then corresponding to $GSH^-$ or Cl.

The reduction of $Au^{3+}$, the native substrate, to $Au^0$ is coupled to the oxidation of NADPH to $NADP^+$. The oxidation of NADPH was observed by measuring the change of absorbance at 340 nm. A 50-µL reaction mixture contained 100 mM PIPES (pH7.0), 400 µM NADPH, 17.9 µM MerA, and varying amounts of $Au^{3+}$. The assay was also used to observe the reduction of $Hg^{2+}$, MerA's native substrate, to $Hg^0$ using substrate $Hg(GSH)_2$.

The kinetic parameters of MerA using $Hg(GSH)_2$ and $AuCl_3$ were determined (Table 4).

TABLE 4

Kinetic parameters of purified MerA

| Parameter | Substrate | |
|---|---|---|
| | $Hg^{2+}$ | $Au^{3+}$ |
| $K_M$ (µM) | 96 ± 58 | 380 ± 140 |
| $k_{cat}$ ($s^{-1}$) | 15 ± 5.1 | 6.8 ± 1.9 × $10^{-3}$ |
| $k_{cat}/K_M$ ($M^{-1}\,s^{-1}$) | 1.5 ± 0.7 × $10^5$ | 1.8 ± 1.3 × $10^1$ |

With respect to mercury substrate, MerA shows a higher $K_M$ of 96.3±57.6 µM as compared to reported literature of 10.7 µM. The $k_{cat}$ value of 14.6±5.1 s$^{-1}$ is slightly faster as compared to reported findings of 9.43 s$^{-1}$ though, the difference is not significant. Overall catalytic efficiency ($k_{cat}$/ $K_M$) value of 1.5±0.7×10$^5$ M$^{-1}$ s$^{-1}$, is six times lower than expected when compared to literature findings of 8.8×10$^5$ M$^{-1}$ s$^{-1}$ (Moore, M. J., Miller, S. M., Walsh, C. T. C-Terminal Cysteines of Tn501 Mecuric Ion Reductase (1992) *Biochemistry* 31(6):1677-85). With respect to AuCl$_3$, no published data is available. When compared to the native substrate, Hg(GSH)$_2$, the $k_{cat}$/$K_M$ using AuCl$_3$ is four magnitudes lower. Thus, the assay is able to be used to determine MerA's reductive capabilities with regards to different substrates.

Improved gold reducing MerA mutants were identified via screening with a gold-sensing biosensor. The golTSB operon isolated from *Salmonella enterica* serovar *typhimurium* functions as a biosensor (Zammit et al., 2013) together with green fluorescent protein (GFP) as a reporter (FIG. 19). This biosensor is under the control of the GolS regulator which is induced in the presence of Au$^+$/Au$^{3+}$ complexes. When Au$^+$/Au$^{3+}$ ions interact with the GolS regulator, the GolS regulator binds to its target promoter sequence, golB. This induces a conformational change in the GolS/golB complex which promotes transcription of GFP reporter. We propose to integrate this circuit into the *E. coli* chromosome as previously shown [Cerminati, S. et al., *Biotechnol Bioeng,* 108(11), 2553-2560 (2011)], and use this *E. coli* strain for endogenous reporting of gold reducing capabilities Biosensor was cloned into the pRSFDuet-1 vector and responsiveness to gold substrate tested. Fluorescence measurements were taken using 485_20 and 528_20 nm filters for excitation and emission wavelengths respectively. The final optical density at 600 nm (OD$_{600}$) of each sample was also measured. Fluorescence measurements (F$_s$) were normalized following the formula (Formula 1).

$$F_x = \frac{RFU^{sample}}{OD_{600}^{sample}} - \frac{RFU^{PRSF}}{OD_{600}^{PRSF}}$$

$$IC = F_{Au^{3+}} / F_{H_2O}$$

Where RFU$^{sample}$ is the fluorescence (measured in instrument's arbitrary relative fluorescence units) and OD$_{600}^{sample}$, the final optic density determined for each sample obtained from the sensor bacteria, and RFU$^{PRSF}$ and ODE$_{600}^{PRSF}$, the same parameters determined for the strain carrying the pPRSFDuet-1 vector. Induction coefficients (IC) were calculated where F$_{Au^{3+}}$ is the normalized fluorescence value of the sensor bacteria exposed to the metal, and F$_{H_2O}$ is the normalized fluorescence of the biosensor cultured without metal added (background fluorescence).

Figures 20, 21:
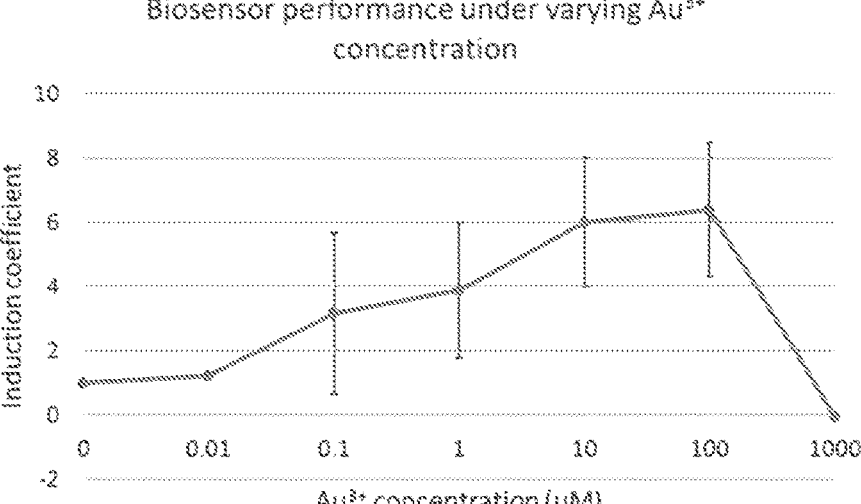
FIG. 20 shows a graph of the biosensitivity of go/GFP with respect to increasing concentration of $Au^{3+}$ (μM).
FIG. 21 shows schematic of screen to identify gold-reducing mutants.

Fluorescence increased with increasing concentration of Au$^{3+}$ concentration up to 100 µM (FIG. 20). At higher concentrations, fluorescence decreased sharply presumably due to susceptibility of *E. coli* to metal toxicity. The limits for Au$^{3+}$ detection, i.e., the lowest and highest gold concentrations that produce a detectable increase in fluorescence compared to the background were determined to be 100 nm to 100 µM for the sensor. Thus, the sensor has proven to be capable of distinguishing different concentrations of Au$^{3+}$ and will be utilized in the screen for an optimal gold reducing MerA mutant.

The screen for an optimal gold reducing MerA mutant is based on observing for a drop in fluorescence, which corresponds to a drop in Au$^{3+}$ ions present intracellularly, hence acting as an indirect reporter for gold reducing activity (FIG. 21). In the presence of gold ions and a control plasmid, the biosensor will be induced, producing a strong fluorescence signal, but in the presence of a gold reducing MerA mutant, gold ions will be reduced, resulting in lack of fluorescence.

Example 7

Gold Biosensor in *Chromobacterium violaceum* is Sensitive to Silver Ions.

Figure 31:
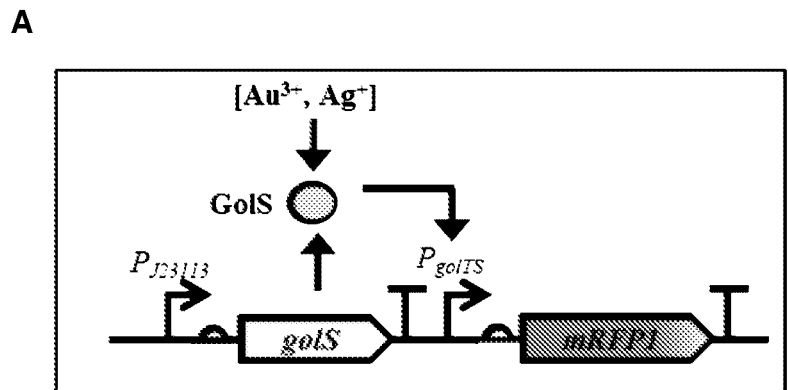
FIG. 31 shows (A) Gold and silver biosensor schematic in *C. violaceum* and (B) a graph of mutant gold sensor sensitivity to different metal ions, $AuCl_3$ (40 μM), $AgNO_3$ (10 μM), $CdCl_2$ (80 μM), $ZnCl_2$ (100 μM), $HgCl_2$ (5 μM), $NiSO_4$ (50 μM), $CoCl_2$ (120 μM), $FeSO_4$ (25 μM) and $CuSO_4$ (35 μM), in minimal media.
Figure 31:
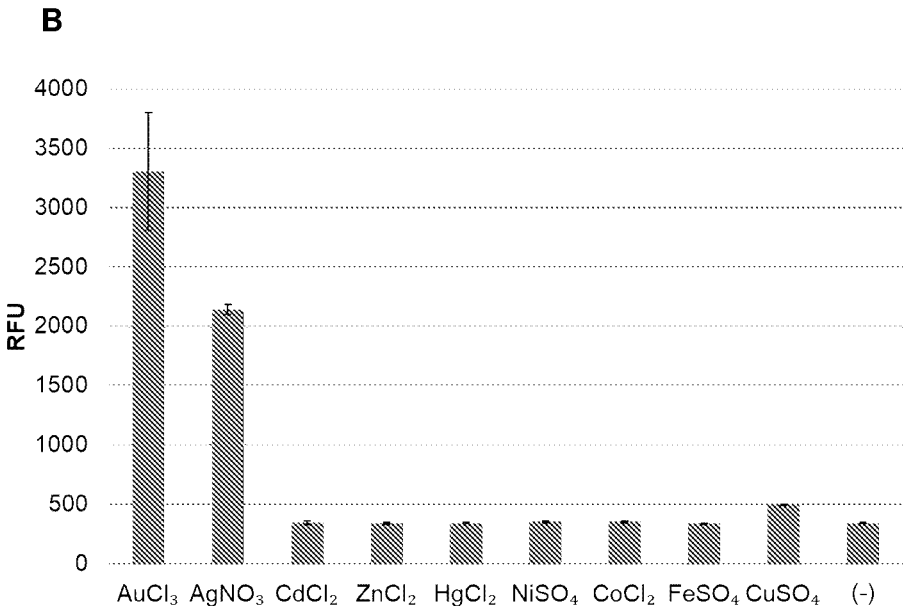
Figure 32:
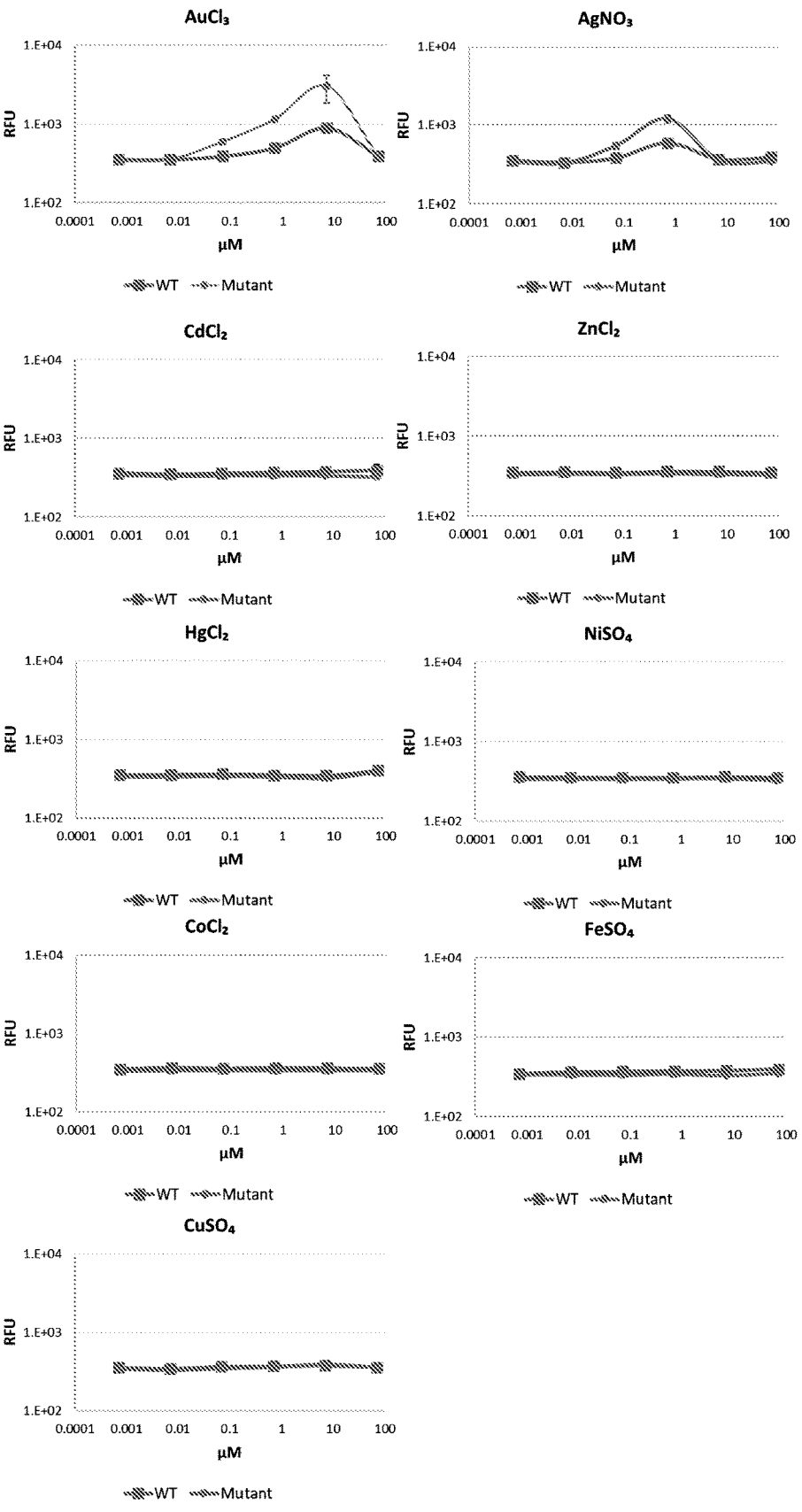
FIG. 32 shows dose-response curves of wild type and mutant biosensor to different metal ions in minimal media.

The biosensor shown in FIG. 31A was tested for its sensitivity to different metal ions in minimal media. The biosensor senses the gold and silver ions but did not have high response to other metals including cadmium, zinc, mercury, nickel, cobalt, iron and copper ions (FIG. 31B). The dose response shows that the mutant biosensor is more sensitive with a larger dynamic range than the wild type biosensor to gold and silver ions (FIG. 32).

Example 8

Sensing of Leached Precious Metal Ions from Electronic Waste by *C. violaceum*

Figure 33:
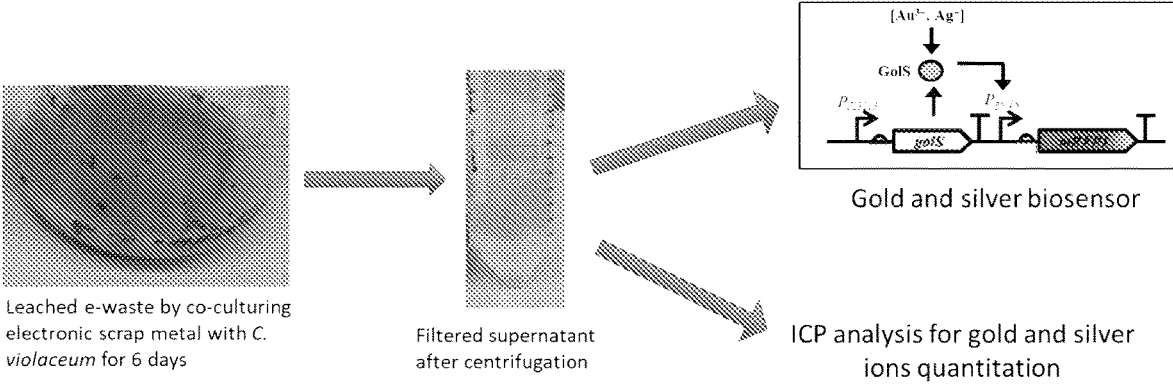
FIG. 33 shows an outline of a process for gold and silver biosensing in *C. violaceum* using leached metals from electronic scrap metal.
Figure 34:
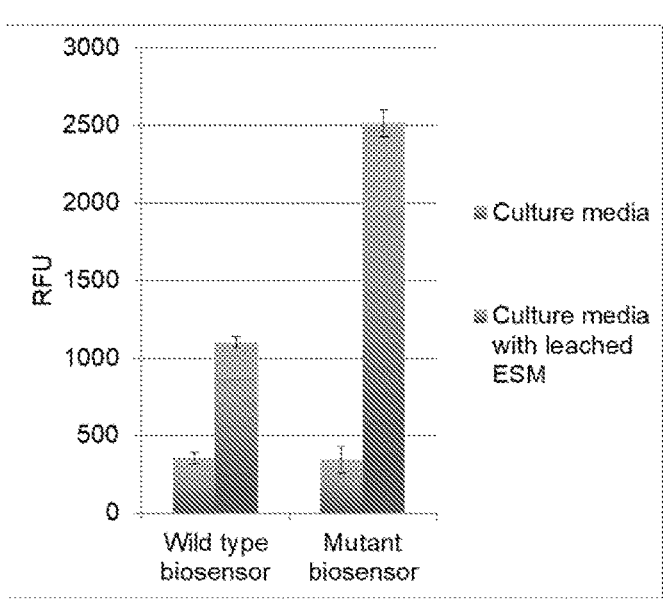
FIG. 34 shows a graph of the ability of wild type and mutant biosensor to sense precious metal ions in a mixture of metal ions leached from electronic scrap metal (ESM).

*C. violaceum* was incubated with electronic waste and cultured for 6 days to leach precious metals from electronic waste into the aqueous culture. After culturing for 6 days, the *C. violaceum* cells were centrifuged down and spent media was added to *C. violaceum* containing the biosensor used in Example 7 (FIG. 33). The transcriptional factor biosensor was activated in the spent culture media with leached ESM but not the control culture media (FIG. 34). The mutant biosensor fluorescence output was 2515 RFU while the wild type biosensor was 1101 RFU in response to the day 6th spent culture with leached ESM. ICP analysis shows that in the 6 days spent culture, there are 1.1 ppm (5.6 µM) gold ions, 0.34 ppm (3.2 µM) silver ions and 12.3 ppm (193.2 µM) copper ions in the spent media. This shows that the biosensor in *C. violaceum* was activated in the presence of gold ions and silver ions from the leached electronic waste media. This will be useful when activating further synthetic circuitries module in *C. violaceum.*

Summary

1. Specific to this invention, we have achieved biological reduction of metal-cyanide complexes after metal cyanidation, using the mercury reductase (Mer) system.
2. Specific to this invention, the tools will allow synthetic circuits for lixiviant biology to be constructed, and refer to the sequential and appropriate expression and activation of respective biological systems for efficient metal recovery, and include the following features:
   a. Regulated, inducible expression of synthetic cyanogenesis modules upon addition of electronic waste to bioreactor. This enables the timely production of cyanide lixiviant for metal bioleaching.
   b. Specific, temporal expression of synthetic metal recovery modules upon detection of respective metallo-cyanide complexes. Due to the heterogeneity of electronic waste, differing concentrations of metals (and the associated metallic ions) necessitate the temporal removal of respective metals; this will be achieved through the selective expression of engineered Mer systems specific towards metal ion valency and identity.

c. Regulated, inducible expression of synthetic cyanolysis modules after metal recovery to metabolize excess cyanide lixiviant, channeling the carbon and nitrogen atoms of cyanide back into central metabolic pathways.

REFERENCES

Arazoe, T., Kondo, A., & Nishida, K. (2018). Targeted nucleotide editing technologies for microbial metabolic engineering. *Biotechnology journal,* 1700596.

Bikard, D., Jiang, W., Samai, P., Hochschild, A., Zhang, F., & Marraffini, L. A. (2013). Programmable repression and activation of bacterial gene expression using an engineered CRISPR-Cas system. *Nucleic Acids Res,* 41(15), 7429-7437. doi:10.1093/nar/gkt520.

Brandl, H., Lehmann, S., Faramarzi, M. A., and Martinelli, D. (2008), Biomobilization of silver, gold, and platinum from solid waste materials by HCN forming microorganisms, *Hydrometallurgy* 94, 14-17.

Brysk, M. M., Corpe, W. A., & Hankes, L. V. (1969). Beta-cyanoalanine formation by *Chromobacterium violaceum. J Bacteriol,* 97(1), 322-327.

Brysk, M. M., & Ressler, C. (1970). γ-Cyano-α-I-aminobutyric acid a new product of cyanide fixation in *Chromobacterium violaceum. Journal of Biological Chemistry,* 245(5), 1156-1160.

Cerminati, S., Soncini, F. C., & Checa, S. K. (2011). Selective detection of gold using genetically engineered bacterial reporters. *Biotechnol Bioeng,* 108(11), 2553-2560.

Checa, S. K., Espariz, M., Audero, M. E., Botta, P. E., Spinelli, S. V., & Soncini, F. C. (2007). Bacterial sensing of and resistance to gold salts. *Mol Microbiol,* 63(5), 1307-1318. doi:10.1111/j.1365-2958.2007.05590.x.

Chi, T. D., Lee, J. C., Pandey, B. D., Yoo, K., and Jeong, J. (2011) Bioleaching of gold and copper from waste mobile phone PCBs by using a cyanogenic bacterium, *Miner Eng* 24, 1219-1222.

Cho, S., Shin, J., & Cho, B. K. (2018). Applications of CRISPR/Cas System to Bacterial Metabolic Engineering. *Int J Mol Sci,* 19(4). doi:10.3390/ijms19041089.

Cobb, R. E., Wang, Y., & Zhao, H. (2014). High-efficiency multiplex genome editing of *Streptomyces* species using an engineered CRISPR/Cas system. *ACS Synth Biol,* 4(6), 723-728.

Faramarzi, M. A., Stagars, M., Pensini, E., Krebs, W., and Brandl, H. (2004) Metal solubilization from metal-containing solid materials by cyanogenic *Chromobacterium violaceum, Journal of Biotechnology* 113, 321-326.

Fields, S. (2001) Tarnishing the earth: gold mining's dirty secret. *Environ Health Perspect* 109, A474-481.

Knowles, C. J. (1976). Microorganisms and cyanide. *Bacteriol Rev,* 40(3), 652-680.

Knowles, C. J., & Bunch, A. W. (1986). Microbial cyanide metabolism. *Adv Microb Physiol,* 27, 73-111.

Korte, F., Spiteller, M. & Coulston, F. (2000) The cyanide leaching gold recovery process is a nonsustainable technology with unacceptable impacts on ecosystems and humans: the disaster in Romania. *Ecotoxicology and Environmental Safety* 46, 241-245.

Krebs, W., Brombacher, C., Bosshard, P. P., Bachofen, R., and Brandl, H. (1997) Microbial recovery of metals from solids, *FEMS Microbiology Reviews* 20, 605-617.

Liang, G., Mo, Y., and Zhou, Q. (2010) Novel strategies of bioleaching metals from printed circuit boards (PCBs) in mixed cultivation of two acidophiles, *Enzyme and Microbial Technology* 47, 322-326.

Liu, W., Jiang, J. G., Shi, G. Y., He, Y., Liu, Y., & Jin, L. T. (2007). Toxicity Assessment of Cyanide and Tetramethylene Disulfotetramine (Tetramine) Using Luminescent Bacteria *Vibrio*-qinghaiensis and PbO2 Electrochemical Sensor. *Chinese Journal of Chemistry,* 25(2), 203-207.

Moore, M. J., Miller, S. M., Walsh, C. T. (1992) C-Terminal Cysteines of Tn501 Mecuric Ion Reductase *Biochemistry* 31(6):1677-85).

Pham, V., and Ting, Y. P. (2009) Gold bioleaching of electronic waste by cyanogenic bacteria and its enhancement with bio-oxidation, *Advanced Materials Research* 71, 661-664.

Rawlings, D. E. (2002) Heavy Metal Mining Using Microbes, *Annual Review of Microbiology* 56, 65-91.

Reith, F., Etschmann, B., Grosse, C., Moors, H., Benotmane, M. A., Monsieurs, P., Brugger, J. (2009). Mechanisms of gold biomineralization in the bacterium *Cupriavidus metallidurans. Proc Natl Acad Sci USA,* 106(42), 17757-17762. doi:10.1073/pnas.0904583106.

Ressler, C., Abe, O., Kondo, Y., Cottrell, B., & Abe, K. (1973). Purification and characterization from *Chromobacterium violaceum* of an enzyme catalyzing the synthesis of γ-cyano-α-aminobutyric acid and thiocyanate. *Biochemistry,* 12(26), 5369-5377.

Shareena Dasari, T. P., Zhang, Y., & Yu, H. (2015). Antibacterial Activity and Cytotoxicity of Gold (I) and (III) Ions and Gold Nanoparticles. *Biochem Pharmacol (Los Angel),* 4(6). doi:10.4172/2167-0501.1000199.

Stanton, B. C., Nielsen, A. A., Tamsir, A., Clancy, K., Peterson, T., & Voigt, C. A. (2014). Genomic mining of prokaryotic repressors for orthogonal logic gates. *Nat Chem Biol,* 10(2), 99-105. doi:10.1038/nchembio.1411.

Swem, L. R., Swem, D. L., O'Loughlin, C. T., Gatmaitan, R., Zhao, B., Ulrich, S. M., & Bassler, B. L. (2009). A quorum-sensing antagonist targets both membrane-bound and cytoplasmic receptors and controls bacterial pathogenicity. *Mol Cell,* 35(2), 143-153. doi:10.1016/j.molcel.2009.05.029.

Watling, H. R. (2006) The bioleaching of sulphide minerals with emphasis on copper sulphides—A review, *Hydrometallurgy* 84, 81-108.

The invention claimed is:

1. An isolated genetically engineered bacterium, wherein the bacterium has been transformed by at least one polynucleotide molecule; the at least one polynucleotide molecule comprising a heterologous mercury (II) reductase (MerA) gene, operably linked to at least one promoter, and comprising at least one mutation which confers the gene product improved catalytic efficiency of reducing ionic gold to elemental gold as gold nanoparticles when compared with a wild type MerA, wherein the at least one mutation encodes amino acid substitutions at positions selected from the group consisting of V317S, A323D, A323D (delΔ324-365), A414E, G415I, E416C, L417I, I418D and A422N of MerA with reference to the amino acid sequence set forth in SEQ ID NO: 34.

2. The isolated bacterium of claim 1, wherein the bacterium is selected from the group consisting of *Chromobacterium violaceum, Pseudomonas fluorescens, P. aeruginosa* and *Escherichia coli* and/or wherein the bacterium is stable at pH 10.

3. A process for recovering elemental gold as gold nanoparticles from ionic gold (Au3+), said process comprising the steps of: a) contacting the isolated genetically engineered bacterium according to claim 1 with a leachate comprising ionic gold (Au3+); and b) recovering the elemental gold nanoparticles from the leachate.

4. The process according to claim 3, wherein the said contact is performed in alkaline conditions.

* * * * *